US011975036B2

(12) United States Patent
Capano et al.

(10) Patent No.: US 11,975,036 B2
(45) Date of Patent: May 7, 2024

(54) METHODS OF TREATING OVARIAN CANCER WITH HEMP EXTRACT

(71) Applicants: Ecofibre USA Inc., Georgetown, KY (US); The University of Newcastle, Callaghan (AU)

(72) Inventors: Alexandra M. Capano, Philadelphia, PA (US); Pradeep Singh Tanwar, Fletcher (AU); Alex Nance, Georgetown, KY (US)

(73) Assignees: Ecofibre USA Inc., Georgetown, KY (US); The University of Newcastle, Callaghan (AU)

( * ) Notice: Subject to any disclaimer, the term of this patent is extended or adjusted under 35 U.S.C. 154(b) by 0 days.

(21) Appl. No.: 18/299,784

(22) Filed: Apr. 13, 2023

(65) Prior Publication Data

US 2023/0405066 A1  Dec. 21, 2023

Related U.S. Application Data

(62) Division of application No. 18/049,961, filed on Oct. 26, 2022, now Pat. No. 11,654,171.

(60) Provisional application No. 63/263,026, filed on Oct. 26, 2021, provisional application No. 63/263,020, filed on Oct. 26, 2021, provisional application No. 63/263,018, filed on Oct. 26, 2021.

(51) Int. Cl.

| | |
|---|---|
| A61K 36/00 | (2006.01) |
| A61K 31/01 | (2006.01) |
| A61K 31/015 | (2006.01) |
| A61K 31/045 | (2006.01) |
| A61K 31/05 | (2006.01) |
| A61K 31/198 | (2006.01) |
| A61K 31/216 | (2006.01) |
| A61K 31/282 | (2006.01) |
| A61K 31/337 | (2006.01) |
| A61K 31/352 | (2006.01) |
| A61K 31/355 | (2006.01) |
| A61K 31/395 | (2006.01) |
| A61K 31/4745 | (2006.01) |
| A61K 31/513 | (2006.01) |
| A61K 31/519 | (2006.01) |
| A61K 31/675 | (2006.01) |
| A61K 31/704 | (2006.01) |
| A61K 31/7048 | (2006.01) |
| A61K 31/7068 | (2006.01) |
| A61K 33/243 | (2019.01) |
| A61K 36/185 | (2006.01) |
| A61K 39/395 | (2006.01) |
| A61P 35/00 | (2006.01) |

(52) U.S. Cl.
CPC ........... *A61K 36/185* (2013.01); *A61K 31/01* (2013.01); *A61K 31/015* (2013.01); *A61K 31/045* (2013.01); *A61K 31/05* (2013.01); *A61K 31/198* (2013.01); *A61K 31/216* (2013.01); *A61K 31/282* (2013.01); *A61K 31/337* (2013.01); *A61K 31/352* (2013.01); *A61K 31/355* (2013.01); *A61K 31/4745* (2013.01); *A61K 31/513* (2013.01); *A61K 31/519* (2013.01); *A61K 31/5545* (2017.08); *A61K 31/675* (2013.01); *A61K 31/704* (2013.01); *A61K 31/7048* (2013.01); *A61K 31/7068* (2013.01); *A61K 33/243* (2019.01); *A61K 39/3955* (2013.01); *A61P 35/00* (2018.01)

(58) Field of Classification Search
CPC ........................................................ A61P 35/00
See application file for complete search history.

(56) References Cited

U.S. PATENT DOCUMENTS

| | | |
|---|---|---|
| 10,098,867 B2 | 10/2018 | Javid et al. |
| 11,123,308 B2 | 9/2021 | Yu et al. |
| 2010/0273895 A1 | 10/2010 | Stinchcomb et al. |
| 2011/0086113 A1 | 4/2011 | Velasco Diez et al. |
| 2015/0086653 A1 | 3/2015 | Parolaro et al. |
| 2016/0136128 A1 | 5/2016 | Javid et al. |
| 2019/0282513 A1 | 9/2019 | Yerike |
| 2020/0253919 A1 | 8/2020 | Raz et al. |
| 2020/0408740 A1 | 12/2020 | Ballan et al. |
| 2021/0052512 A1 | 2/2021 | Guy et al. |
| 2021/0068444 A1 | 3/2021 | Alarcon et al. |
| 2021/0069608 A1 | 3/2021 | Galyuk |
| 2021/0085638 A1 | 3/2021 | Hospodor |
| 2021/0128521 A1 | 5/2021 | Palaio |
| 2021/0145764 A1 | 5/2021 | Lephart |
| 2022/0000774 A1 | 1/2022 | Dely |

(Continued)

FOREIGN PATENT DOCUMENTS

| | | |
|---|---|---|
| CN | 108433880 A | 8/2018 |
| CN | 110063953 A | 7/2019 |

(Continued)

OTHER PUBLICATIONS

Griffiths et al, Cannabidiol suppresses 3-dimensional ovarian cancer growth and may enhance potency of classic and epigenetic therapies. Gynecologic Oncology, (Aug. 2021) vol. 162, Supp. Supplement 1, pp. S102-S103 (Year: 2021).*

(Continued)

*Primary Examiner* — Qiuwen Mi
(74) *Attorney, Agent, or Firm* — Vos-IP, LLC

(57) ABSTRACT

Methods for treating ovarian cancer comprising: administering to a patient and effective amount of a cannabis extract comprising CBD wherein preferably the cannabis extract is administered via a mucosal formulation.

16 Claims, 21 Drawing Sheets

(56) References Cited

U.S. PATENT DOCUMENTS

| | | |
|---|---|---|
| 2022/0054429 A1 | 2/2022 | Nathan et al. |
| 2022/0062224 A1 | 3/2022 | Gubler et al. |
| 2022/0202765 A1 | 6/2022 | Altman et al. |
| 2022/0253919 A1 | 8/2022 | Denner |
| 2022/0331287 A1 | 10/2022 | Morgan et al. |
| 2023/0015268 A1 | 1/2023 | Altman et al. |
| 2023/0127098 A1 | 4/2023 | Capano et al. |
| 2023/0132189 A1 | 4/2023 | Capano et al. |
| 2023/0248747 A1 | 8/2023 | Altman et al. |
| 2023/0355645 A1 | 11/2023 | Storch et al. |

FOREIGN PATENT DOCUMENTS

| | | | |
|---|---|---|---|
| EP | 3368024 A1 | 9/2018 | |
| EP | 3449992 A1 | 3/2019 | |
| EP | 3544598 A1 | 10/2019 | |
| EP | 3915550 A1 | 12/2021 | |
| EP | 3937914 A1 | 1/2022 | |
| GB | 2516335 A | 1/2015 | |
| RU | 2745687 C1 | 3/2021 | |
| WO | WO/2013/165251 A1 | 11/2013 | |
| WO | WO/2014/057067 A1 | 4/2014 | |
| WO | WO/2016/187679 A1 | 12/2016 | |
| WO | WO/2018/167038 A1 | 9/2018 | |
| WO | WO/2019/003163 A2 | 1/2019 | |
| WO | WO/2019/034113 A1 | 2/2019 | |
| WO | WO/2019/106652 A1 | 6/2019 | |
| WO | WO/2019/145552 A1 | 8/2019 | |
| WO | WO/2019/195943 A1 | 10/2019 | |
| WO | WO/2019/222459 A1 | 11/2019 | |
| WO | WO/2020/036655 A9 | 2/2020 | |
| WO | WO/2020/163775 A1 | 8/2020 | |
| WO | WO/2020/165878 A1 | 8/2020 | |
| WO | WO/2020/183455 A1 | 9/2020 | |
| WO | WO/2020/194237 A1 | 10/2020 | |
| WO | WO/2020/209902 A1 | 10/2020 | |
| WO | WO-2020194237 A1 * | 10/2020 | ............. A61K 31/05 |
| WO | WO/2021/011790 A1 | 1/2021 | |
| WO | WO/2021/016718 A1 | 2/2021 | |
| WO | WO/2021/028646 A1 | 2/2021 | |
| WO | WO/2021/099792 A1 | 5/2021 | |
| WO | WO/2021/130728 A1 | 7/2021 | |
| WO | WO/2021/158251 A1 | 8/2021 | |
| WO | WO/2021/235977 A1 | 11/2021 | |
| WO | WO/2021/240510 A1 | 12/2021 | |
| WO | WO/2021/245522 A1 | 12/2021 | |
| WO | WO/2022/013854 A1 | 1/2022 | |
| WO | WO/2022/016160 A1 | 1/2022 | |
| WO | WO/2022/018708 A1 | 1/2022 | |
| WO | WO/2022/105952 A1 | 5/2022 | |
| WO | WO/2022/118303 A1 | 6/2022 | |
| WO | WO/2022/144878 A1 | 7/2022 | |
| WO | WO/2022/165349 A1 | 8/2022 | |
| WO | WO/2022/165439 A1 | 8/2022 | |
| WO | WO/2022/215071 A1 | 10/2022 | |
| WO | WO/2022/225658 A1 | 10/2022 | |
| WO | WO/2023/287742 A1 | 1/2023 | |
| WO | WO/2023/014818 A2 | 2/2023 | |
| WO | WO/2023/062634 A1 | 4/2023 | |

OTHER PUBLICATIONS

Sumanasekera et al, Hemp Extract with Specific Anti-Cancer Properties against Ovarian Cancer. FASEB Journal, (May 2021) vol. 35, No. Suppl. 1, Sp. Iss (Year: 2021).*

Jin et al, Identification of Chemotypic Markers in Three Chemotype Categories of Cannabis Using Secondary Metabolites Profiled in Inflorescences, Leaves, Stem Bark, and Roots. Frontiers in plant science, (2021) vol. 12, pp. 699530 (Year: 2021).*

Rais et al, Phytochemicals in the treatment of ovarian cancer. Frontiers in Bioscience—Elite, (Jan. 1, 2017) vol. 9, No. 1, pp. 67-75 (Year: 2017).*

Marinotti et al, Differentiating Full-Spectrum Hemp Extracts from CBD Isolates: Implications for Policy, Safety and Science. ournal of dietary supplements, (2020) vol. 17, No. 5, pp. 517-526 (Year: 2020).*

International Search Report issued in International Application No. PCT/US2022/078698 dated Dec. 14, 2022, Dec. 14, 2022.

International Search Report issued in International Application No. PCT/US2022/078701 dated Feb. 15, 2023, Feb. 15, 2023.

International Search Report issued in International Application No. PCT/US2022/078691 dated Jan. 30, 2023, Jan. 30, 2023.

International Search Report issued in International Application No. PCT/US2022/078693 dated Jan. 30, 2023, Jan. 30, 2023.

Armour, et al., "Self-Management Strategies Amongst Australian Women With Endometriosis: A National Online Survey", BMC Complementary and Alternative Medicine, vol. 19, No. 1, art. 17, Jan. 15, 2019, 1-8.

Escudero-Lara, et al., "Disease-Modifying Effects of Natural $\Delta^9$—Tetrahydrocannabinol in Endometriosis-Associated Pain", eLife, vol. 9, art. e50356, Jan. 14, 2020, https://elifesciences.org/articles/50356.

Fonseca, et al., "Cannabinoid-Induced Cell Death in Endometrial Cancer Cells: Involvement of TRPV1 Receptors in Apoptosis", Journal of Physiology and Biochemistry, vol. 74, No. 2, Feb. 13, 2018, 261-272.

Fraguas-Sånchez, et al., "Enhancing Ovarian Cancer Conventional Chemotherapy Through the Combination With Cannabidiol Loaded Microparticles", European Journal of Pharmaceutics and Biopharmaceutics, vol. 154, Jul. 17, 2020, 246-258.

Go, et al., "Cannabidiol Enhances Cytotoxicity of Anti-Cancer Drugs in Human Head and Neck Squamous Cell Carcinoma", Scientific Reports, vol. 10, No. 1, art. 20622, Nov. 26, 2020, 1-11.

Griffiths, et al., "Cannabidiol Suppresses 3-Dimensional Ovarian Cancer Growth and May Enhance Potency of Classic and Epigenetic Therapies", Gynecologic Oncology, vol. 162, suppl. 1, Abstracts for the 2021 Society of Gynecologic Oncology 52nd Annual Meeting on Women's Cancer, Aug. 18, 2021, S102-S103.

Jaidee, et al., "Kinetics of CBD, $\Delta^9$—THC Degradation and Cannabinol Formation in Cannabis Resin at Various Temperature and pH Conditions", Cannabis and Cannabinoid Research, vol. 7, No. 4, Aug. 9, 2022, 1-11.

Jin, et al., "Identification of Chemotypic Markers in Three Chemotype Categories of Cannabis Using Secondary Metabolites Profiled in Inflorescences, Leaves, Stem Bark, and Roots", Frontiers in Plant Science, vol. 12, art. 699530, Jul. 1, 2021, 1-16.

Kenyon, et al., "Report of Objective Clinical Responses of Cancer Patients to Pharmaceutical-Grade Synthetic Cannabidiol", Anticancer Research, vol. 38, No. 10, Oct. 1, 2018, 5831-5835.

Lazarjani, et al., "Processing and Extraction Methods of Medicinal Cannabis: A Narrative Review", Journal of Cannabis Research, vol. 3, art. 32, Jul. 19, 2021, 1-15.

Marinelli, et al., "The Effects of Cannabidiol and Prognostic Role of TRPV2 in Human Endometrial Cancer", International Journal of Molecular Sciences, vol. 21, No. 15, art. 5409, Jul. 29, 2020, 1-22.

Marinotti, et al., "Differentiating Full-Spectrum Hemp Extracts from CBD Isolates: Implications for Policy, Safety and Science", Journal of Dietary Supplements, vol. 17, No. 5, Jun. 16, 2020, 517-526.

Okten, et al., "Cannabidiol as a Potential Novel Treatment for Endometriosis by Its Anti-Inflammatory and Anti-Oxidative Effects in an Experimental Rat Model", Human Reproduction, vol. 37, issue supp. 1, Jun. 30, 2022, i111.

Rais, et al., "Phytochemicals in the Treatment of Ovarian Cancer", Frontiers in Bioscience-Elite, vol. 9, No. 1, Jan. 1, 2017, 67-75.

Rush, et al., "Cannabidiol: Assessing Activity in Ovarian and Endometrial Carcinoma Cell Lines", Abstracts for the 2021 Society of Gynecologic Oncology 52nd Annual Meeting on Women's Cancer, Featured Posters 188-Poster Session, vol. 162, suppl. 1, Aug. 1, 2021, https://doi.org/10.1016/S0090-8258(21)00839-8.

Sumanasekera, et al., "Hemp Extract With Specific Anti-Cancer Properties Against Ovarian Cancer", The FASEB Journal Special Issue: Experimental Biology 2021 Meeting Abstracts, vol. 35, No. S1, May 14, 2021, https://doi.org/10.1096/fasebj.2021.35.S1.02877.

(56) References Cited

OTHER PUBLICATIONS

Hazekamp, et al., "Preparative Isolation of Cannabinoids from Cannabis sativa by Centrifugal Partition Chromatography", Journal of Liquid Chromatography & Related Technologies, vol. 27, No. 15, 2004, 2421-2439.
Van Weelden, et al., "Anti-Estrogen Treatment in Endometrial Cancer: A Systematic Review", Frontiers in Oncology, vol. 9, art. 359, May 7, 2019, 1-12.

* cited by examiner

Cannabinoid Receptor 2 Protein Expression in Endometrial Cancer Patient Samples

Endometrial Cancer (Endometrioid Type)

Cannabinoid Receptor 1 Protein Expression in Endometrial Cancer Patient Samples

Endometrial Cancer (Endometrioid Type)

Chemosensitive Ovarian Cancer Treated with Different Doses of CBD

Chemoresistent Ovarian Cancer Cells Treated with Different Doses of CBD

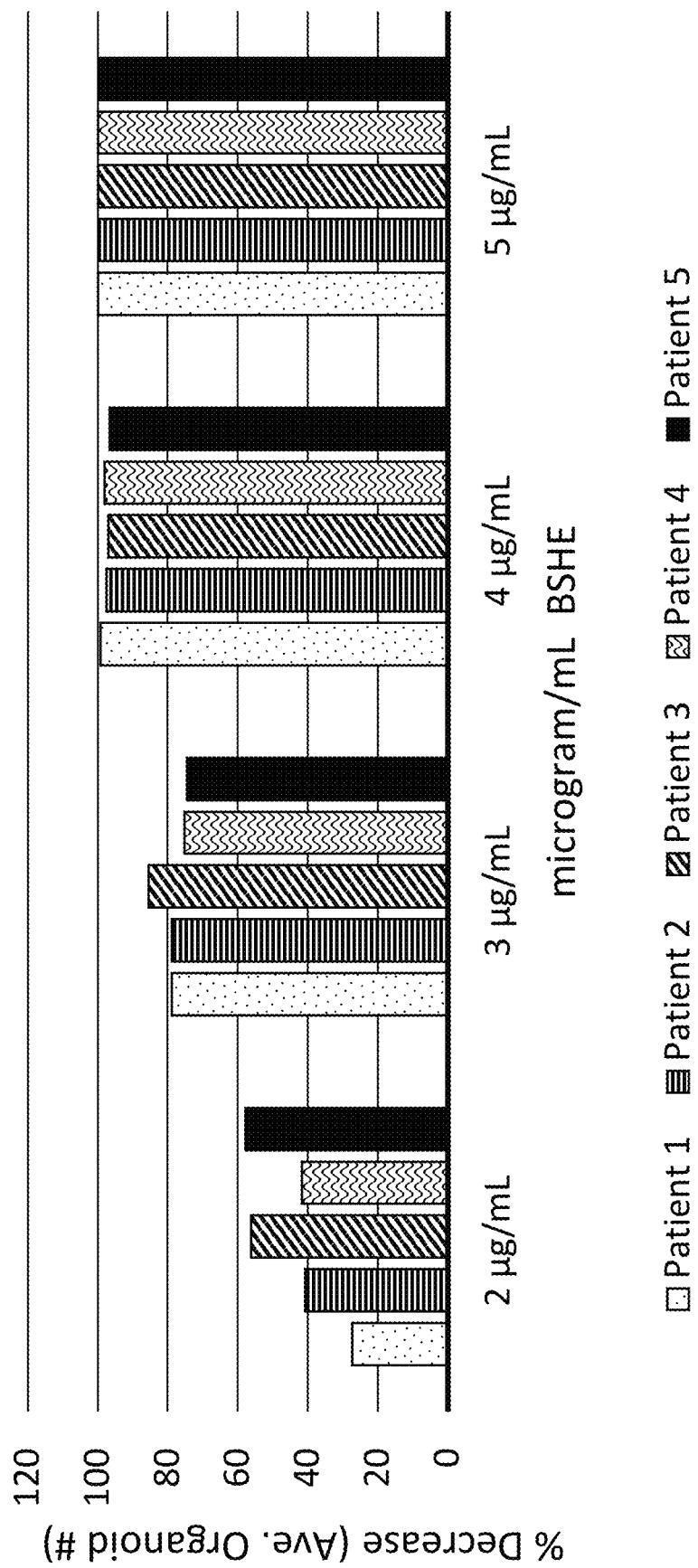

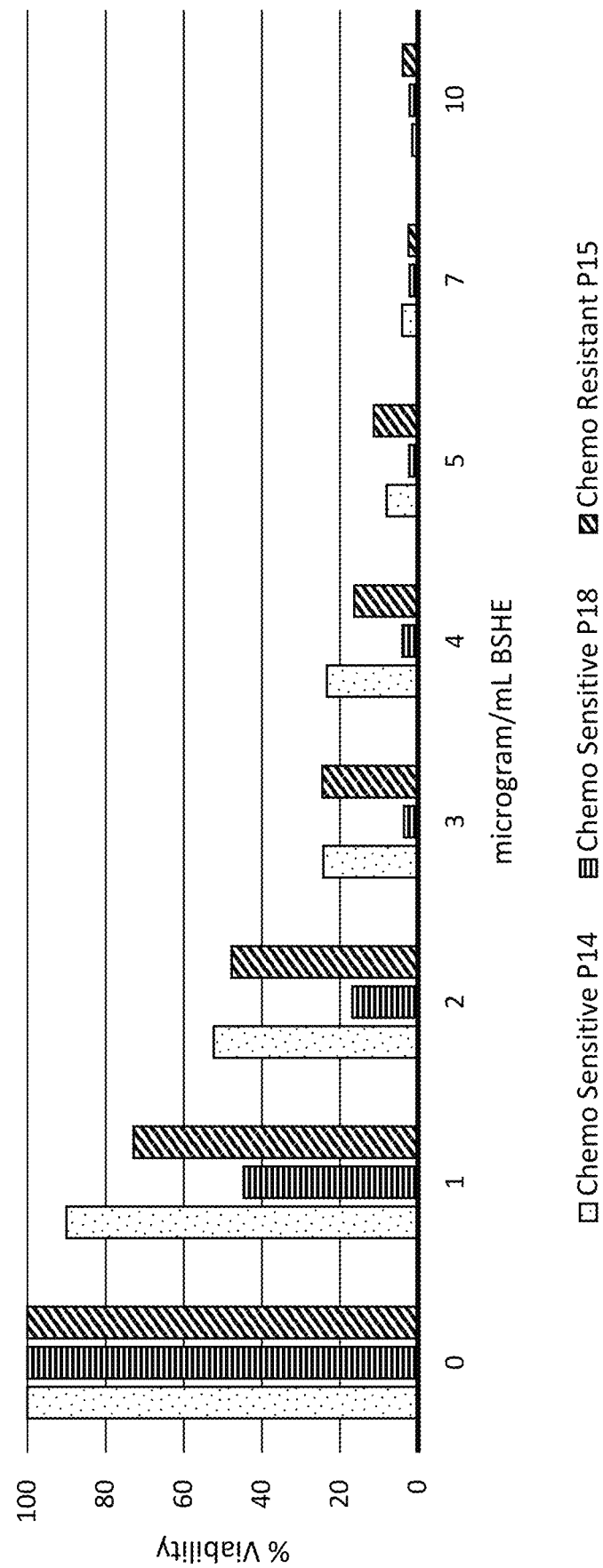

Chemo Sensitive and Chemo Resistant Ovarian Cancer Organoids Response to FSHE

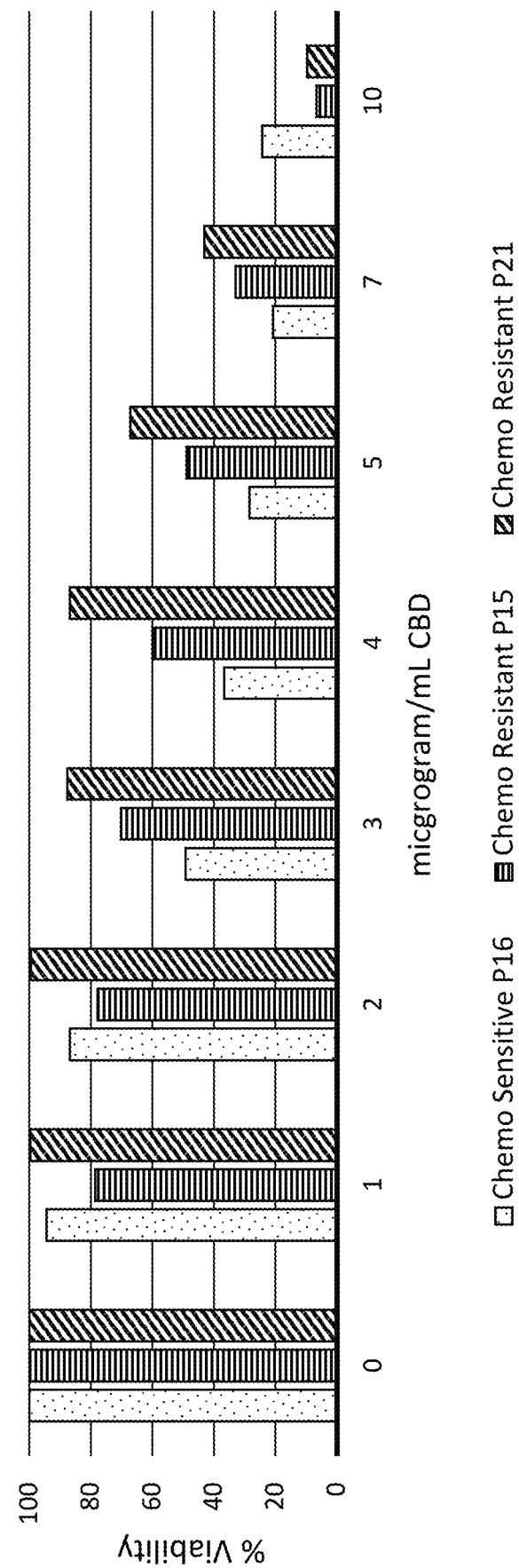

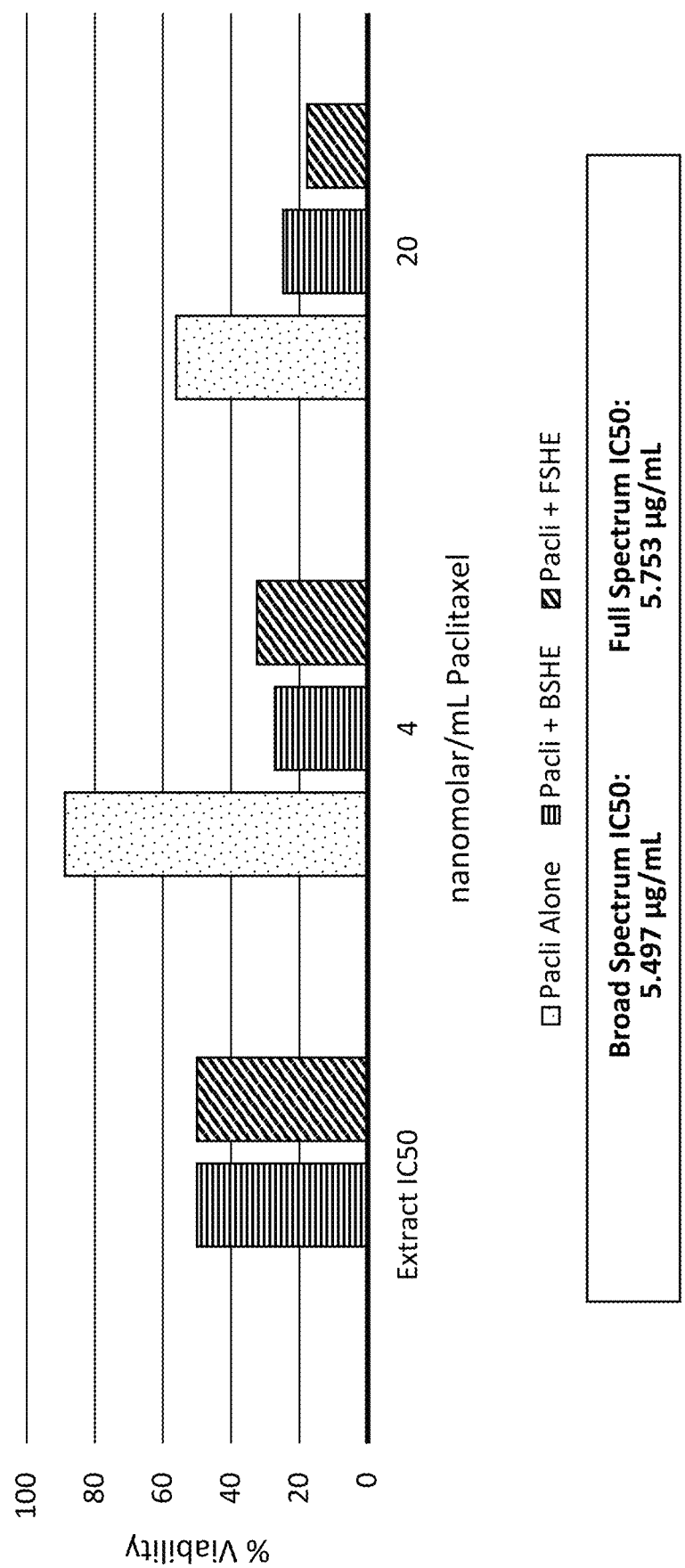

Chemo Resistant Ovarian Cancer Organoid Response to Paclitaxel and Paclitaxel + Cannabinoid Extract

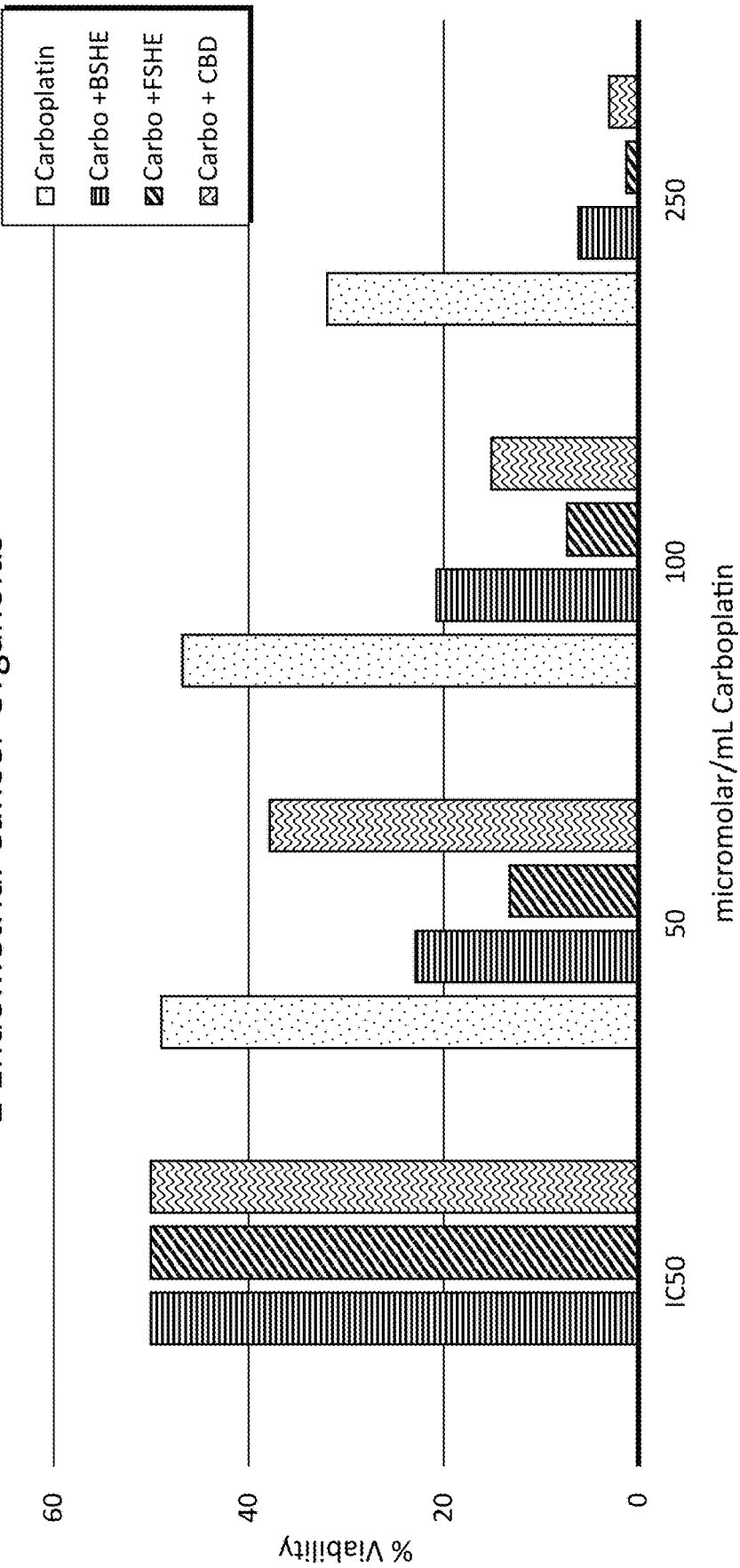

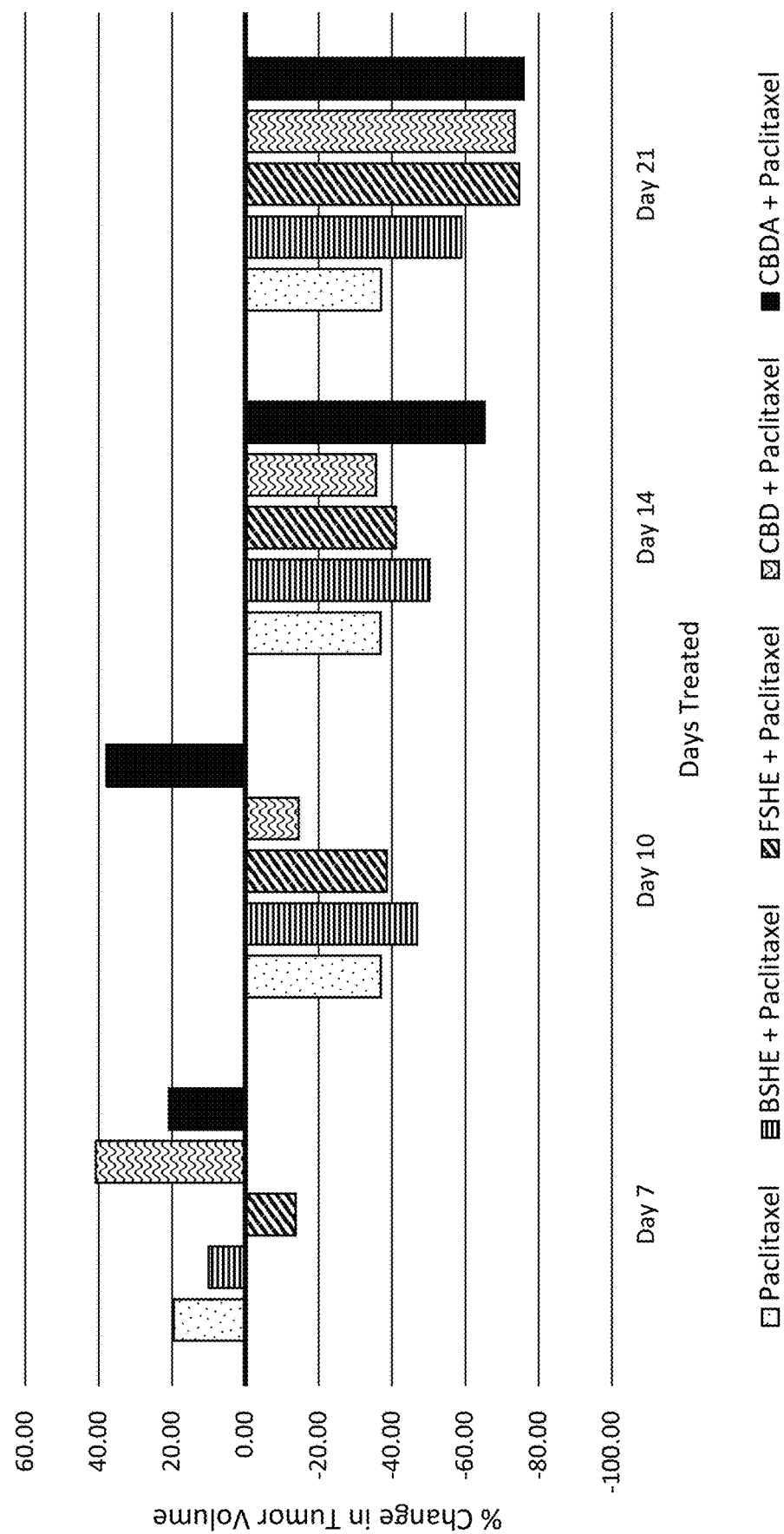

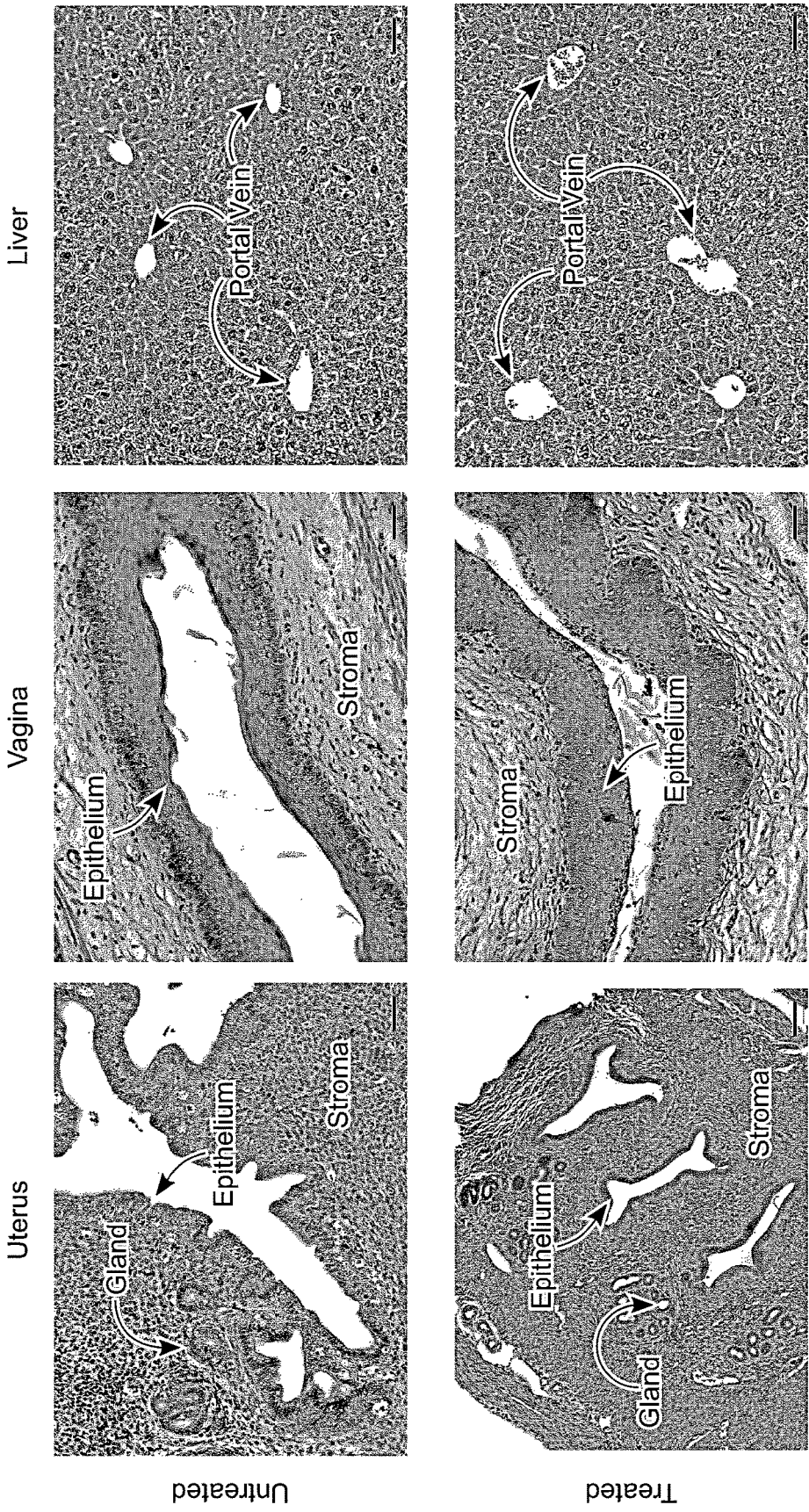

Effects pH and Cannabinoid Extract (10 μg/mL) on Ovarian Cancer Organoid Viability

METHODS OF TREATING OVARIAN CANCER WITH HEMP EXTRACT

CROSS-REFERENCE TO RELATED APPLICATIONS

This application is a divisional of U.S. patent application Ser. No. 18/049,961 filed on Oct. 26, 2022, which claims the benefit of U.S. Provisional Patent Application No. 63/263,018 filed on Oct. 26, 2021, U.S. Provisional Patent Application No. 63/263,026 filed on Oct. 26, 2021, and U.S. Provisional Patent Application No. 63/263,020 filed on Oct. 26, 2021, with the United States Patent and Trademark Office, the contents of which are incorporated herein by reference in their entirety.

FIELD OF THE INVENTION

The inventions disclosed herein are related to compositions and therapeutic treatments of ovarian cancers, through administration of an effective amount of cannabis extracts alone or in combination with a chemotherapeutic agent. The cannabis extracts comprise one or more cannabinoids, and specifically therapeutic amounts of cannabidiol (CBD) and often include one or more additional cannabinoid, terpene, or other molecules within the cannabis extract.

BACKGROUND OF THE INVENTION

Cancer represents the phenotypic end point of multiple genetic lesions that endow cells with a full range of biological properties required for tumorigenesis. Indeed, a hallmark genomic feature of many cancers, including gynecological cancers such as ovarian cancer, is the presence of numerous complex chromosome structural aberrations, including translocations, intra-chromosomal inversions, point mutations, deletions, gene copy number changes, gene expression level changes, and germline mutations, among others. Whether a cancer will respond to a given treatment option may depend on the particular genomic features present in the cancer.

Women face a host of gynecological disorders for which there is currently no adequate method of treatment. These conditions range from non-life-threatening disorders such as polycystic ovarian syndrome and endometriosis to life altering cancers. Cancers may infiltrate any number of cells and organs in the gynecological tract. Unfortunately, many of these cancers are aggressive and have significant risk of metastatic disease, where the migrate from their cellular origin into the rest of the body. Furthermore, many of the gynecological cancers suffer from chemoresistance, wherein despite aggressive treatments, the cancer stops is not responsive to the chemotherapy and continues to advance.

Ovarian cancer is the second most common gynecologic cancer in the United States and causes more deaths than any other cancer of the female reproductive system. Treatment for ovarian cancer usually involves a combination of surgery and chemotherapy. Unfortunately, as there are no screening options for ovarian cancer, the disease is often detected in later stages of cancer progression and patients are most commonly diagnosed in Stage 3 of ovarian cancer. Stage 3 cancer means that the ovarian cancer cells have spread or grown into nearby organs of the pelvis, and thus the disease is not contained within the ovaries or fallopian tubes. Because of the late stage of diagnosis, and the aggressiveness of ovarian cancer, the five-year survival rate is only approximately 39%. Current treatment options remain inadequate.

Applicant has identified methods of treatment of ovarian cancers comprising administration of cannabis extracts comprising CBD. Applicant has identified that one of more cannabis extracts comprising CBD are suitable for chemosensitive, chemoresistance, and chemonaive cancers, whether administered as a monotherapy or when combined with one or more chemotherapy agents. Furthermore, we advocate for the therapeutic dosing via mucosal administration of the cannabis extract, including the vaginal mucosa, oral mucosa, rectal mucosa, or nasal mucosa, in addition to other routes of administration. These and other embodiments are detailed with more particularity herein.

SUMMARY OF THE INVENTION

The embodiments herein are related to methods of treatment of ovarian cancer comprising administering to a patient in need thereof an effective amount of a cannabis extract.

In preferred embodiments, the process of administering to a patient comprises an oral and/or an intravaginal application of the cannabis extract. In a further preferred embodiment, the method comprises a concomitant therapeutic application of an intravaginal composition or rectal composition comprising a cannabis extract and concomitantly administering a cannabis extract via oral dosing or the oral mucosa, wherein the combined effect creates an effective amount of CBD for systemic treatment of certain cancers and gynecological disorders. In preferred embodiments, the combined therapy provides both a local administration of CBD and also a systemic administration without undue damage to healthy cells.

The cannabis extracts comprise one or more cannabinoids, and specifically therapeutic amounts of cannabidiol (CBD) and often include one or more additional cannabinoid, terpene, or other molecules within the cannabis extract. In certain embodiments, the methods further include the therapeutic treatment of chemo sensitive and chemo resistant ovarian cancers. Further methods relate to methods for treatment using a combined therapeutic treatment plan comprising a chemotherapeutic agent and a cannabis extract. Further methods relate to certain routes of administration of ovarian cancers, including treatment methods using cannabis extracts comprising CBD for treatment of cancers through a combined protocol comprising intravaginal application and/or oral or oral mucosal formulations to reach therapeutically effective doses for treatment of ovarian cancer.

In an embodiment, the present invention provides a cannabis extract for use in a method of treating ovarian cancer in a patient wherein said cannabis extract comprises cannabidiol (CBD).

In an embodiment, the present invention provides an intravaginal composition for use in a method of treating ovarian cancer in a patient wherein said intravaginal composition comprises a cannabis extract comprising cannabidiol and a pharmaceutically acceptable excipient.

In an embodiment, the present invention provides a cannabis extract for use in a method of treating ovarian cancer in a patient wherein said cannabis extract comprises cannabidiol (CBD) and wherein said method is a method for treating ovarian cancer and the method comprises administering the cannabis extract to the patient concomitantly via an oral formulation and via an intravaginal formulation. As defined herein, the term "concomitantly" means that the oral formulation and the intravaginal formulation are administered to the patient no more than 72 hours apart, preferably no more than 48 hours apart, and more preferably no more than 24 hours apart, for example no more than 12 hours apart, no more than 6 hours apart, no more than 4 hours, apart, no more than 3 hours apart, no more than 2 hours apart, no more than an hour apart, no more than 30 minutes apart, or simultaneously. Thus, in an embodiment, the present invention provides an oral formulation for use in a method for treating ovarian cancer wherein said oral formulation comprises a cannabis extract comprising cannabidiol (CBD) and a pharmaceutically acceptable excipient, and said method comprises administration of the oral formulation concomitantly with an intravaginal formulation comprising a cannabis extract comprising cannabidiol (CBD) and a pharmaceutically acceptable excipient. In a further embodiment, the present invention provides an intravaginal formulation for use in a method for treating ovarian cancer wherein said intravaginal formulation comprises a cannabis extract comprising cannabidiol (CBD) and a pharmaceutically acceptable excipient, and said method comprises administration of the intravaginal formulation concomitantly with an oral formulation comprising a cannabis extract comprising cannabidiol (CBD) and a pharmaceutically acceptable excipient.

In an embodiment, the present invention provides a cannabis extract for use in a method of treating ovarian cancer wherein said cannabis extract comprises cannabidiol (CBD) and wherein said method comprises coadministering to a patient an effective amount of said cannabis extract and an effective amount of a chemotherapeutic agent. As defined herein, the term "coadministering" means that the cannabis extract and the chemotherapeutic agent are administered to the patient no more than 72 hours apart, preferably no more than 48 hours apart, and more preferably no more than 24 hours apart, for example no more than 12 hours apart, no more than 6 hours apart, no more than 4 hours, apart, no more than 3 hours apart, no more than 2 hours apart, no more than an hour apart, no more than 30 minutes apart, or simultaneously.

In an embodiment, the present invention provides a chemotherapeutic agent for use in a method of treating ovarian cancer wherein said method comprises coadministering to a patient an effective amount of said chemotherapeutic agent and an effective amount of a cannabis extract, wherein said cannabis extract comprises cannabidiol (CBD).

In an embodiment, the present invention provides a pharmaceutical composition for use in a method of treating an ovarian cancer wherein said pharmaceutical composition comprises a cannabis extract and an effective amount of CBD.

In an embodiment, the present invention provides the use of a cannabis extract comprising cannabidiol (CBD) in the manufacture of a medicament for use in a method of treating ovarian cancer.

In an embodiment, the present invention provides the use of an intravaginal composition comprising a cannabis extract comprising cannabidiol and a pharmaceutically acceptable excipient in the manufacture of a medicament for use in a method of treating ovarian cancer.

In an embodiment, the present invention provides the use of a cannabis extract comprising cannabidiol (CBD) in the manufacture of a medicament for use in a method of treating ovarian cancer wherein said cannabis extract is coadministered with a chemotherapeutic agent.

In an embodiment, the present invention provides the use of a chemotherapeutic agent in the manufacture of a medicament for use in a method of treating ovarian cancer wherein said chemotherapeutic agent is coadministered with a cannabis extract comprising cannabidiol (CBD).

In an embodiment, the present invention provides the use of a pharmaceutical composition comprising a cannabis extract and an effective amount of CBD in the manufacture of a medicament for use in a method of treating a ovarian cancer.

In a preferred embodiment, a cannabis extract for use in a method of treating ovarian cancer in a patient wherein said cannabis extract comprises cannabidiol (CBD).

In a further embodiment, the cannabis extract for use wherein said cannabis extract is selected from a full spectrum hemp extract (FSHE), a broad spectrum hemp extract (B SHE), a CBD isolate, and cannabidiolic acid (CBDA), optionally wherein the BSHE or FSHE comprises (i) from 50% to 99% by weight of CBD and (ii) at least one other cannabinoid selected from Δ-9-tetrahydrocannabinol (Δ$^9$-THC), tetrahydrocannabinolic acid (THCA), tetrahydrocannabivarin (THCV), Δ-8-tetrahydrocannabinol (Δ$^8$-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof.

In a further embodiment, the cannabis extract for use wherein said cannabis extract comprises between 10 mg and 500 mg CBD per dose.

In a further embodiment, the cannabis extract for use wherein: (a) the method comprises administration of the cannabis extract to the patient via an oral dose, oral mucosal dose, intravaginal dose, or combinations thereof; and/or (b) the method comprises administration of a dose of the cannabis extract to the patient at least once every three days, preferably at least once a day, at least twice a day, or at least three times a day; and/or (c) the method comprises administration of an amount of the cannabis extract sufficient to generate a concentration of at least 10 μg/mL of the cannabis extract at a target tissue in the patient, preferably wherein the target tissue is a cancerous tissue of a female reproductive tract; and/or (d) the method comprises administration of an amount of the cannabis extract sufficient to reach an effective therapeutic level as measured through systemic plasma levels of CBD; and/or (e) the method comprises administration of between 20 mg and 4,250 mg of CBD to the patient per day; and/or (f) the cannabis extract is formulated at an acidic pH, preferably at a pH between 3.5 and 6.

In a further embodiment, the cannabis extract for use wherein: (a) the ovarian cancer has metastasized; and/or (b) the ovarian cancer is a chemoresistant cancer.

In a further embodiment, the cannabis extract for use wherein said cannabis extract comprises between 1% and 99.9% CBD and wherein the method comprises administering the cannabis extract to the patient via intravaginal administration, preferably wherein: (a) the cannabis extract comprises between 60% and 99.9% CBD; and/or (b) the cannabis extract is selected from a full spectrum hemp extract (FSHE), a broad spectrum hemp extract (B SHE), and a CBD isolate; and/or (c) the cannabis extract comprises CBDA.

In a preferred embodiment, a mucosal composition for use in a method of treating ovarian cancer in a patient wherein said mucosal composition comprises a cannabis extract and a pharmaceutically acceptable excipient.

In a further embodiment, the mucosal composition for use wherein the composition comprises (i) an oil or fat as a carrier and/or (ii) at least one terpene, at least one polyphenol, at least one essential fatty acid, at least one phytonutrient, or a combination thereof, optionally wherein the at least one terpene, at least one polyphenol, at least one essential fatty acid, at least one phytonutrient, or combination thereof make up between 1% and 50% by weight of the total weight of the composition, further optionally wherein: the terpene is selected from β-myrcene, β-caryophyllene, linalool, α-pinene, citral, D-limonene, eucalyptol, and combinations thereof; and/or the polyphenol is selected from a catechin, quercetin, cannflavin A/B/C, rutin, chlorogenic acid, and combinations thereof; and/or the essential fatty acid is selected from an omega 3 acid, an omega 6 acid, an omega 9 acid, and combinations thereof; and/or the phytonutrient is selected from a tocopherol, a sterol, carotene, an aliphatic alcohol, a mineral, and combinations thereof.

In a further embodiment, the mucosal composition for use wherein: (a) the mucosal composition comprises a dose of between 25 mg and 4,250 mg CBD and the method comprises administering the composition to the patient via insertion to a mucosal surface selected from oral mucosa, rectum, vagina, or nasal passages; and/or (b) the method comprises administering at least two doses of the mucosal composition to the patient per day, wherein each dose of the mucosal composition comprises between 10 mg and 2,125 mg cannabis extract; and/or (c) the mucosal composition has an acidic pH, preferably a pH between 3.5 and 6.

In a further embodiment, the cannabis extract for use wherein said method is a method for treating ovarian cancer and the method comprises administering the cannabis extract to the patient concomitantly via a mucosal formulation, preferably wherein the cannabis extract is a full spectrum hemp extract (FSHE) or a broad spectrum hemp extract (B SHE).

In a further embodiment, the cannabis extract for use wherein said method comprises coadministering to a patient an effective amount of said cannabis extract and an effective amount of a chemotherapeutic agent.

In a preferred embodiment, a chemotherapeutic agent for use in a method of treating ovarian cancer wherein said method comprises coadministering to a patient an effective amount of said chemotherapeutic agent and an effective amount of a cannabis extract.

In a preferred embodiment, a cannabis extract for use or a chemotherapeutic agent for use wherein: (a) the chemotherapeutic agent is selected from paclitaxel, altretamine, capecitabine, cyclophosphamide, etoposide, gemcitabine, ifosfamide, itinotecan, doxorubicin, melphalan, pemetrexed, topotecan, binorelbine, carboplatin, cisplatin, docetaxel, and combinations thereof; and/or (b) the ovarian cancer is a chemoresistant cancer; and/or (c) the method comprises a first step of determining chemoresistance of a cancerous tissue in a patient and a subsequent step of administering to the patient an effective amount of the cannabis extract and an effective amount of the chemotherapeutic agent upon confirmation of chemoresistance; and/or (d) the effective amount of the chemotherapeutic agent is at least 50% less than an indicated dose of the chemotherapeutic agent when administered in the absence of the cannabis extract; and/or (e) the method comprises administering the cannabis extract to the patient in an amount of between 20 mg and 4,250 mg per day.

In a preferred embodiment, a composition for use in a method of treating ovarian cancer, wherein the composition comprises between 1 and 99% by weight of a CE.

In a preferred embodiment, a composition wherein the CE of the composition comprises (a) a FSHE, a BSHE, a CBD isolate, a CBDA isolate; and/or (b) wherein the composition comprises a carrier at between 1 and 99% by weight of the composition; and/or (c) wherein the composition further comprises one or more excipients at between 1 and 50% by weight of the composition.

In a preferred embodiment, a composition for treatment of ovarian cancer, wherein the composition comprises a cannabis extract (CE), wherein the CE comprises between 1 and 100% by weight of the composition and all percentages therein. In preferred embodiments, the CE comprises between 10 and 90% by weight, or 20 by 90% by weight, and preferably between and 80% by weight of the composition. The CE, as detailed herein, is preferably a BSHE, a FSHE, a CBD isolate, or a CBDA isolate. In each of these different CE, the BSHE, the FSHE, the CBD isolate, or the CBDA isolate, they make up between 50 and 99.9% by weight of the CE, with the remaining being waxes, fats, fatty acids and the like. However, preferred embodiments utilize a carrier at between 1 and 99% by weight of the composition, and preferably, one or more additional excipients depending on the use case of the composition. The composition is typically then administered based upon the dosage in mg of CBD being administered. Wherein the amount of the composition required to meet that mg of CBD depends on the quantity of CBD within each of the CE.

In a further preferred embodiment, a method of treatment of ovarian cancer comprising administering to a patient in need thereof, an effective amount of a composition according to any one of the preceding embodiments. In a preferred embodiment, wherein the effective amount is between 20 and 4250 mg of cannabidiol (CBD).

In a preferred embodiment, a pharmaceutical composition for use in a method of treating an ovarian cancer wherein said pharmaceutical composition comprises a cannabis extract comprising an effective amount of CBD.

In a further embodiment, the pharmaceutical composition for use wherein the composition further comprises: (a) a carrier; and/or (b) at least one additional cannabinoid selected from Δ-9-tetrahydrocannabinol ($Δ^9$-THC), tetrahydrocannabinolic acid (THCA), tetrahydrocannabivarin (THCV), Δ-8-tetrahydrocannabinol (Δ8-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL) and combinations thereof; and/or (c) at least one terpene, preferably wherein the terpene is selected from β-myrcene, β-caryophyllene, linalool, α-pinene, citral, D-limonene, eucalyptol, and combinations thereof; and/or (d) at least one polyphenol, preferably wherein the polyphenol is selected from a catechin, quercetin, cannflavin A/B/C, rutin, chlorogenic acid, and combinations thereof; and/or (e) an essential fatty acid, preferably wherein the essential fatty acid is selected from an omega 3 acid, an omega 6 acid, an omega 9 acid, and combinations thereof; and/or (f) a phytonutrient, preferably wherein the phytonutrient is selected from a tocopherol, a sterol, carotene, an aliphatic alcohol, a mineral, and combinations thereof.

In a preferred embodiment, a method for treating ovarian cancer comprising: administering to a patient and effective amount of a composition comprising a cannabis extract (CE).

In a further embodiment, the method wherein the CE comprises between 50% and 99.9% cannabidiol (CBD).

In a further embodiment, the method wherein the CE is selected from the group consisting of: a full spectrum hemp extract (FSHE), a broad spectrum hemp extract (B SHE), a CBD isolate, and a cannabidiolic acid (CBDA) isolate.

In a further embodiment, the method wherein the CE is administered via an oral form, oral mucosal form, intravaginal form, nasal mucosal form, rectal form, injectable form, or combinations thereof.

In a further embodiment, the method wherein the effective amount of the cannabis extract comprising CBD comprises between 10 mg and 4,250 mg of CBD per day.

In a further embodiment, the method wherein administration of the CE is a dose given at least once a day, at least twice a day, or at least three times a day.

In a further embodiment, the method wherein the ovarian cancer is a grade 1, grade 2, or grade 3 cancer. In a further embodiment, the method wherein the ovarian cancer is a chemoresistant ovarian cancer.

In a further embodiment, the method wherein the CE comprises CBDA at a concentration of between 0.1% and 10%.

In a further embodiment, the method wherein the CE is a BSHE or FSHE and wherein each of the BSHE or FSHE comprises 50% to 99% by weight of CBD and at least one other cannabinoid at a concentration of 0.1% to 10% wherein the at least one other cannabinoid is selected from the group consisting of: $\Delta^9$-THC, THCA, THCV, $\Delta$8-THC, CBC, CBCA, CBG, CBGA, CBDA, CBDV, CBN, CBL, and combinations thereof. In a further embodiment, the method wherein the CE comprises CBD at a concentration of between 60% and 99%, and at least one other cannabinoid at a concentration of 0.1% to 10% wherein the at least one other cannabinoid is selected from the group consisting of: $\Delta^9$-THC, THCA, THCV, $\Delta^8$-THC, CBC, CBCA, CBG, CBGA, CBDA, CBDV, CBN, CBL, and combinations thereof; and wherein the CE comprises a total concentration of cannabinoids of between 65% and 99%.

In a further embodiment, the method wherein the composition comprises at least one additional compound selected from the group consisting of: a terpene, a polyphenol, an essential fatty acid, a phytonutrient, and combinations thereof; and wherein the at least one additional compound makes up between 0.1% and 50% of the total weight of the composition.

In a further embodiment, the method wherein the composition comprises an oil or a fat as a carrier.

In a further embodiment, the method wherein the effective amount of the composition is an amount sufficient to reach an effective therapeutic level of CBD as measured through systemic plasma levels.

In a further embodiment, the method wherein the composition is administered at an acidic pH. In a further embodiment, the method wherein the acidic pH is between 3.5 and 6.

In a preferred embodiment, a method of treatment of ovarian cancer comprising administering to a patient an effective amount of a chemotherapeutic agent and coadministering an effective amount of a cannabis extract (CE).

In a further embodiment, the method wherein the chemotherapeutic agent and the CE are administered as one composition or as two different compositions.

In a further embodiment, the method wherein the chemotherapeutic agent is selected from the group consisting of: paclitaxel, carboplatin, doxorubicin, cisplatin, docetaxel, fluorouracil, methotrexate, cetuximab, and combinations thereof.

In a further embodiment, the method wherein the composition comprising the CE is a composition for oral, rectal, intravaginal, oromucosal, or nasal delivery.

In a further embodiment, the method wherein the effective amount of the composition is sufficient to reach an effective therapeutic level as measured through systemic plasma levels of CBD.

In a further embodiment, the method wherein the ovarian cancer is a chemoresistant cancer.

In a further embodiment, the method wherein the effective amount of a chemotherapeutic agent is at least 50% less than an indicated individual dose and wherein the CE is administered at between 20 mg and 4,250 mg per day.

In a further embodiment, the method wherein the cannabis extract is administered in a composition at an acidic pH. In a further embodiment, the method wherein the acidic pH is between 3.5 and 6.

In a further embodiment, the method comprising a first step of determining chemoresistance of a cancerous tissue from said patient and administering to the patient an effective amount of the CE upon confirmation of chemoresistance.

In a further embodiment, the method wherein the CE comprises a cannabinoid selected from the group consisting of: $\Delta^9$-THC, THCA, THCV, $\Delta^8$-THC, CBC, CBCA, CBG, CBGA, CBDA, CBDV, CBN, CBL, and combinations thereof.

In a further embodiment, the method further comprising at least one terpene. In a further embodiment, the method wherein the terpene is selected from the group consisting of: $\beta$-myrcene, $\beta$-caryophyllene, linalool, $\alpha$-pinene, citral, D-limonene, eucalyptol, and combinations thereof.

In a further embodiment, the method further comprising at least one polyphenol. In a further embodiment, the method wherein the polyphenol is selected from the group consisting of: catechins, quercetin, cannflavin A/B/C, rutin, chlorogenic acid, and combinations thereof.

In a further embodiment, the method further comprising an essential fatty acid selected from the group consisting of: an omega 3, an omega 6, an omega 9, and combinations thereof.

In a further embodiment, the method further comprising a phytonutrient. In a further embodiment, the method wherein the phytonutrient is selected from the group consisting of: a tocopherol, a sterol, carotene, an aliphatic alcohol, a mineral, and combinations thereof.

In a further embodiment, the method wherein the CBD is derived from a phytocannabinoid derived from a cannabis extract.

In a preferred embodiment, a method for treating ovarin cancer comprising: (a) taking a cancerous cell from a patient and forming an organoid from the cancerous cell; (b) performing a screen on the organoid to determine a chemotherapeutic drug capable of reducing the precent of viable organoids by 50% with an IC50 dose of the chemotherapeutic drug; and
  (c) administering to the patient the chemotherapeutic drug with an effective amount of a composition comprising a cannabis extract (CE) having between 50% and 99.9% CBD.

In a preferred embodiment, a method of treating ovarian cancer comprising:
  (a) taking an ovarian cancer cell from a patient and forming at least one organoid from the ovarian cancer cell; (b) performing a screen on the at least one organoid to determine a chemotherapeutic drug responsive to the patient's organoid; and (c) administering to the patient the chemotherapeutic drug with an effective amount of a composition comprising a cannabis extract (CE) having between 50% and 99.9% CBD.

In a further embodiment, the method wherein the CE is administered to the patient as an oral form, oromucosal form, nasal form, rectal form, intravaginal form, injectable form, or combinations thereof. In a further embodiment, the method wherein the CE is administered oromucosally and intravaginally.

In a preferred embodiment, a composition for use in a method of treating ovarian cancer wherein the composition comprises between 1% and 99% by weight of a cannabis extract (CE).

In a further embodiment, the composition wherein the CE of the composition comprises: (a) a full spectrum hemp extract (FSHE), a broad spectrum hemp extract (B SHE), a CBD isolate, a CBDA isolate, or combinations thereof; and/or (b) wherein the composition comprises a carrier at between 1% and 99% by weight of the composition; and/or (c) wherein the composition further comprises one or more excipients at between 1% and 50% by weight of the composition.

In a preferred embodiment, a composition for treatment of ovarian cancer wherein the composition comprises a cannabis extract (CE), wherein the CE comprises between 1% and 100% by weight of the composition and all percentages therein.

In a further embodiment, the composition wherein the CE comprises between 10% and 90% by weight, or between 20% and 90% by weight, and preferably between 40% and 80% by weight of the composition.

In a further embodiment, the composition wherein the CE is preferably a full spectrum hemp extract (FSHE), a broad spectrum hemp extract (BSHE), a CBD isolate, or a CBDA isolate. In a further embodiment, the composition wherein the BSHE and/or the FSHE and/or the CBD isolate and/or the CBDA isolate constitute between 50% and 99.9% by weight of the CE.

In a further embodiment, the composition comprising a carrier at between 1% and 99% by weight of the composition.

In a further embodiment, the composition further comprising at least one or more additional excipients.

In a further embodiment, the composition wherein the composition is a mucosal composition.

In a further embodiment, the composition comprising between 20 mg and 4,250 mg of CBD.

In a preferred embodiment, a method of treatment of ovarian cancer comprising administering to a patient in need thereof a composition in an effective amount. In a further embodiment, the method wherein the effective amount is between 20 mg and 4,250 mg of cannabidiol (CBD).

BRIEF DESCRIPTION OF THE FIGURES

FIG. 1C depicting upregulated and down regulated cells in the vehicle and with a cannabis extract comprising CBD treatment; FIG. 1D depicting the top 20 up and down regulated proteins in ECC treated cells; and FIG. 1E depicting the cannabis extract's effects on signaling and trafficking of various physiological and pathophysiological pathways. FIG. 1F depicts cannabinoid receptor 1 protein expression in an endometrial cancer cell; and FIG. 1G depicts cannabinoid receptor 2 protein expression in an endometrial cancer cell.

FIGS. 4A and 4B depict a graphical overview of the response of high grade ovarian cancer organoids to low doses (FIG. 4A) of 2, 3, 4, and 5 μg/mL of CBD, and FIG. 4B depicting higher doses at 3, 5, 7, and 10 μg/mL doses.

FIGS. 5A, 5B, 5C, and 5D, depict results from chemosensitive and chemoresistant ovarian cancer patient derived organoids, being tested against four different cannabis extracts, namely a broad spectrum hemp extract (BSHE) (FIG. 5A), a full spectrum hemp extract (FSHE) (FIG. 5B), a CBD isolate (FIG. 5C) and CBDA (FIG. 5D).

FIGS. 7A and 7B depict ovarian cancer organoid cells and their response to paclitaxel and a combined treatment of paclitaxel and cannabis extract. FIG. 7A depicts chemosensitive organoids and FIG. 7B depicts chemoresistant organoids.

FIG. 8 depicts a combined therapy treatment tested on patient derived endometrial cancer organoids, wherein the chemotherapy agent is carboplatin and is administered with a cannabis extract.

FIG. 9 depicts tumor volume data for mice administered paclitaxel and a cannabis extract, which depicts the synergy related to the combined impact of chemotherapy being combined with the cannabis extract.

FIGS. 10A and 10B depict images of a histopathology performed on mouse tissues treated with cannabis extract and depicting that therapeutic treatment with the cannabis extracts does not damage the normal reproductive tract cells of the ovary, fallopian tubes, uterus, vagina, or also from the liver.

DETAILED DESCRIPTION OF THE INVENTION

Figure 1C:
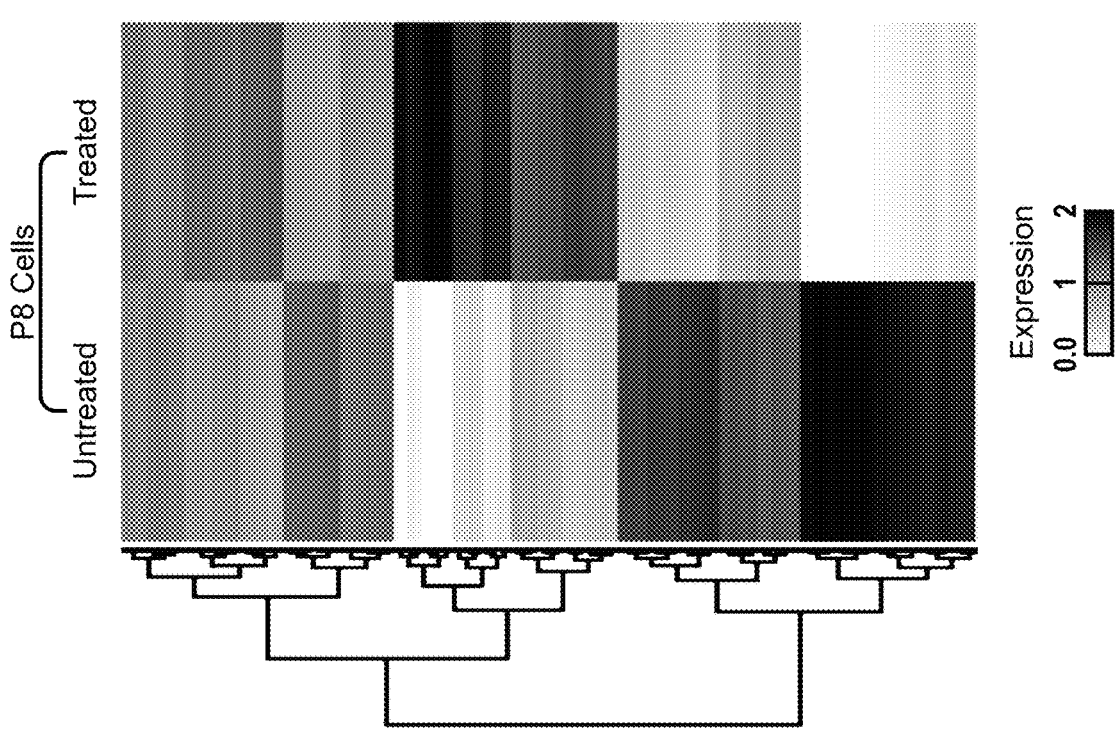
FIGS. 1A, 1B, 1C, 1D, 1E, 1F, and 1G depict endometrial cancer cells being treated with a cannabis extract comprising CBD, with FIG. 1A showing a diagram of the process of capturing the data regarding protein expression, FIG. 1B depicting protein differentiation numbers.

Various embodiments are described more fully hereinafter with reference to the accompanying drawings, which form a part hereof. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be therapeutic products, methods of treatment, use of therapeutics in treating the one or more afflictions of ovarian cancer. The following detailed description is, therefore, not to be taken in a limiting sense.

As used herein, the term "about" means plus or minus 5% of the numerical value of the number with which it is being used. Therefore, about 50% means in the range of 45%-55%. Thus, 20 mg means the range of 19-21, inclusive of the endpoints and all numbers in between.

"Administering" when used in conjunction with a therapeutic means to administer a therapeutic directly to a subject, whereby the agent positively impacts the target. "Administering" the therapeutic drug or compound may be accomplished by, for example, injection, oral administration, topical administration, mucosal administration and/or in combination with other known techniques. The administering techniques may further include heating, radiation, chemotherapy, ultrasound, and the use of delivery agents. Preferably in the present disclosure the administration is through oral, oral mucosal/sublingual, nasal, intramuscular, rectal, and/or intravaginal dosage forms. Such intravaginal forms are intended to be inserted into the vagina, typically with a carrier, wherein the active ingredients pass through the vaginal mucosal membrane. The active ingredients may also be provided in an oral form, to be swallowed. Another oral form is an oral mucosal application, which is often provided as a sublingual application, which, while it is ultimately swallowed to enter the stomach, is intended to be held in the mouth, for example under the tongue, and the active ingredients pass through the oral mucosal membrane before being swallowed or passed into the stomach by salivary action or active swallowing of the materials or both.

By "pharmaceutically acceptable," it is meant that the components including, but not limited to the carrier, diluent, adjuvant, or excipient must be compatible with the other ingredients of the formulation and not deleterious to the recipient thereof.

As used here, the term "composition" is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s) and the inert ingredient(s) that make up the carrier, as well as any product which results, directly or indirectly, from combination, complexation, or aggregation of any two or more of the ingredients or from dissociation of one or more of the ingredients, or from other types of reactions or interactions of one or more of the ingredients. Accordingly, the pharmaceutical compositions of the present invention encompass any composition made by admixing a compound or compounds of the present invention and a pharmaceutically acceptable carrier.

As used herein, the terms "agent," "active agent," "therapeutic agent," or "therapeutic" mean a compound or composition utilized to treat, combat, ameliorate, prevent, or improve an unwanted condition or disease of a patient. Furthermore, the terms "agent," "active agent," "therapeutic agent," or "therapeutic" encompass a cannabis extract and/or additional agents as described in the present disclosure.

A "therapeutically effective amount" or "effective amount" of a composition is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue to achieve the therapeutic response. Specifically, the therapeutic shall be effective in treating cancerous growths related to ovarian cancer, and metastatic disease relating thereto.

The terms "treat," "treated," or "treating" as used herein refer to both therapeutic treatment and prophylactic or preventative measures wherein the object is to prevent or slow down (lessen) an undesired physiological condition, disorder, or disease, or to obtain beneficial or desired clinical results. For the purposes of this disclosure, beneficial or desired results include, but are not limited to, alleviation of symptoms; diminishment of the extent of the condition, disorder, or disease such as a reduction in the size of a tumor; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease.

As used here, the term "cannabis extract" (CE) is a composition derived from the Cannabis genus of plants (including hemp). Typically, a cannabis extract contains cannabidiol, and more typically comprises both cannabidiol (CBD) and at least one additional cannabinoid, selected from the group consisting of $\Delta^9$-THC, THCA, THCV, $\Delta^8$-THC, CBC, CBCA, CBG, CBGA, CBDA, CBDV, CBN, CBL, and combinations thereof at between 0.1 and 40%. Cannabis extracts according to the present invention are typically enriched in cannabidiol, and may comprise between 1 and 99.9% CBD, preferably between 20 and 99.9% CBD, more preferably between 50 and 99.9% CBD, even more preferably between 70 and 99.9% CBD, and most preferably between 90 and 99.9% CBD. Full spectrum hemp extract, broad spectrum hemp extract, CBD isolate, and CBDA isolate are forms of cannabis extract utilized herein, as non-limiting examples of the CE. Throughout the application, the term CBD is often used interchangeably with CE, to mean the CE product containing the particular amount of CBD. while in other instances, which are obvious to the reader, the CBD refers to a CBD isolate, which means the CE was processed to remove and isolate CBD, removing virtually all other components of the CE.

As used herein, the term full spectrum hemp extract (FHSE) is a composition derived from the Cannabis genus of plants which contains CBD, and quantities of THC above 0, preferably, between 0.01 and 5%, most preferably being between 0.01% and 0.3%. The FSHE may comprise additional cannabinoids, yielding a product that comprises at least 50-99% CBD, at least 0.01 to 10% THC ($\Delta^9$-THC, THCA, THCV, $\Delta^8$-THC), and total cannabinoids of between 50% and 99% of the weight of the CE.

As used herein, the term broad spectrum hemp extract (BHSE) is a composition derived from the Cannabis genus of plants which has undergone at least some purification in order to refine the extract. Typically, a BHSE comprises between 60 and 99.9% CBD and least one additional cannabinoid, selected from the group consisting of $\Delta^9$-THC, THCA, THCV, $\Delta^8$-THC, CBC, CBCA, CBG, CBGA, CBDA, CBDV, CBN, CBL, and combinations thereof at between 0.1 and 40%.

Ovarian cancer is a growth of cells that form from the ovaries or in the related areas of the fallopian tubes and the peritoneum. There are three types of ovarian tumors, including epithelial cell tumors, which form from the cells that cover the surface of the ovary and which account for the majority of ovarian tumors, germ cell tumors, which develop from the cells that make the eggs in the ovary, and stroma cell tumors, which are tumors that develop in the cells of the structural tissue of the ovary responsible for producing female hormones.

Ovarian cancer is the second most common gynecological cancer, with an incidence rate of about 20,000 new diagnosis each year in the United States. Furthermore, the unfortunate aspect is that about 13,000 women die each year in the United States from ovarian cancer, making it the leading cause of death of cancer of the female reproductive system. Ovarian cancer, like other cancers, has higher incidence rates based upon certain genetic mutations, including those to BRCA1 and BRCA2, and those associated with Lynch syndrome.

Upon detection of ovarian cancer, most patients elect for surgical removal, including hysterectomy and bilaterial salpingo-oophorectomy. In most cases, this is followed by chemotherapy. Depending on the stage of the cancer, which can vary from stages I, least amount of spread, to stage IV, having widespread metastases, chemotherapy is typically indicated after the surgical removal. In view of the significant side effects of chemotherapy, a small portion of stage I and II patients may omit or reduce chemotherapy use as compared to Stages III and IV patients. Chemotherapy is virtually always given to stage III or stage IV ovarian cancer patients, and often with several rounds of treatment, with the goal of optimizing the risks and the rewards. For Stage III and IV ovarian cancer, accordingly, organ and tumor removal is typically followed by chemotherapy treatment to capture metastatic disease, as the ovarian cancer cells have already migrated from the ovaries, into the uterus and possibly into other body parts within the abdomen and beyond.

However, it is well-known that chemotherapy agents are indiscriminate in their killing, and thus significant secondary impacts occur to the patient leading to impacts on the quality of life. Indeed, even where the chemotherapy is effective in treating the cancer, the toxic effects of the chemotherapy often prove fatal overtime. In a recent study, use of chemotherapy to treat cancer, hastened death in 27% of cases. In a further study, 43% of cancer patients receiving chemotherapy showed significant treatment-related toxicity, despite receiving other parallel treatments to reduce the side effects of the chemotherapy. A total of one-in-four patients died as a direct result of the chemotherapy, instead of the cancer. This is especially troubling as about 20% of patients taking chemotherapy should not have been receiving the chemotherapy at all. Because of the risks associated with chemotherapy, including the toxicity to healthy cells as well as the presence of chemoresistance, there is a significant need for new therapeutic treatments including ways to reduce or replace chemotherapy for ovarian cancers.

In virtually all cases, chemotherapy is given in a cycle, meaning a drug or combination of drugs are given for a period of usually 2-6 weeks, and then a rest period, followed by a second or more treatment period. Some of the chemotherapy agents that are often prescribed include, but are not limited to paclitaxel, altretamine, capecitabine, cyclosphosphamide, etoposide, gemcitabine, ifosfamide, itinotecan, doxorubicin, melphalan, pemetrexed, topotecan, binorelbine, carboplatin, cisplatin, docetaxel, and combinations of these and other agents.

Chemotherapy drugs typically fall into different classes of drugs, an alkylating agent, an antimetabolite, anti-tumor antibiotics, topoisomerase inhibitors, mitotic inhibitors, DNA repair enzyme inhibitors, plant alkaloids, and antineoplastics. Of the most common chemotherapy drugs for ovarian cancer, these fall into the following classes: Paclitaxel is an antineoplastic—plant alkaloid; Docetaxel is an antineoplastic—plant alkaloid; Doxorubicin is an antineoplastic—anthracycline antibiotic; Carboplatin is an antineoplastic—alkylating agent and platinum based; and Cisplatin is an antineoplastic—alkylating agent and platinum based. Frequently, paclitaxel is given in combination with one or more of cisplatin or carboplatin. However, while over 80% of ovarian cancer patients initially respond to platinum-based chemotherapy, the majority relapse, and the term "platinum-resistant" refers to patients with ovarian cancer who progress within six-months of platinum-based therapy. Studies have identified that HIF1α, a heterodimeric transcription factor that regulates multiple cellular pathways, is an important mechanism governing platinum resistance. Of course, when a primary therapy fails, these patients are at the highest risk for disease related mortality. Even with aggressive treatment and especially when not detected until stage III or IV, metastatic tumors lead to low survival rates at 2 and 5 years past initial diagnosis and treatment.

Chemoresistance, of which platinum resistant is one variety, is defined as simply that the cancer cells are resistant to the action of the particular therapeutic agent, such that the disease progresses. Chemoresistant disease may still have some clinical response to the drug, but not at sufficient levels to prevent disease progression, or would require such high doses to make the treatment unsuitable. Chemosensitive, therefore being the opposite, wherein the cancer cells in a patient are sensitive to the chemotherapy agent, so that the disease is managed or reduced. However, cancers may at one point respond to the chemotherapy and become chemoresistant as treatment progresses through a typical on/off cycle. Indeed, presently, where chemoresistant tumors exist, there are few, if any treatment plans other than palliative care, or additional removal upon the identification of tumors. This later step becomes nearly impossible when tumors metastasize.

Indeed, the side effects of chemotherapy are often chronic and include damage to major organs and organ systems, such as the brain, central and peripheral nervous systems, heart, lungs, liver, gastrointestinal tract, and reproductive tract. Chemotherapies can even result in secondary cancer over time. Further, chemotherapy can be fatal, particularly when used in higher doses. A recent inquiry evaluating this effect concluded that chemotherapy or its side effects directly resulted in death in 27% of patients. Additionally, 43% percent of patients in the study suffered significant treatment-related toxicity within just 30 days of receiving chemotherapy.

Accordingly, it is important to both create treatments that improve on the primary treatment, i.e., destruction of ovarian cancer cells and reduction of ovarian cancer cell loads, reducing the chances of metastasis within the body, and to reduce tumor size for any unresected tumors, with the ultimate goal of extending life, through management of tumor or by reaching remission. However, in view of the significant morbidity and mortality directly attributed to use of chemotherapy, methods and treatments to reduce the quantities of chemotherapy, or duration of chemotherapy treatment would dramatically improve cancer treatments. Each of these outcomes may signify a successful treatment in one or more patients. New treatments that provide for an improvement of quality of life as well as new and effective treatments that can reduce the doses of chemotherapy or impact direct lesions or metastatic disease are urgently desired.

Figure 1A:
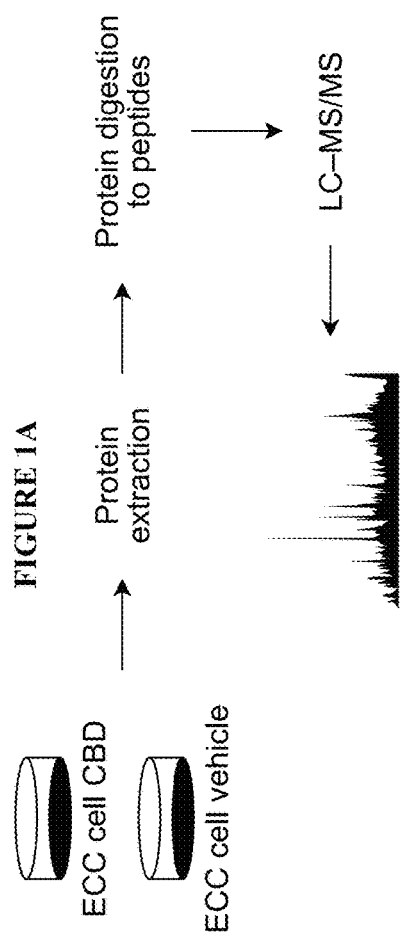
Figure 1B:
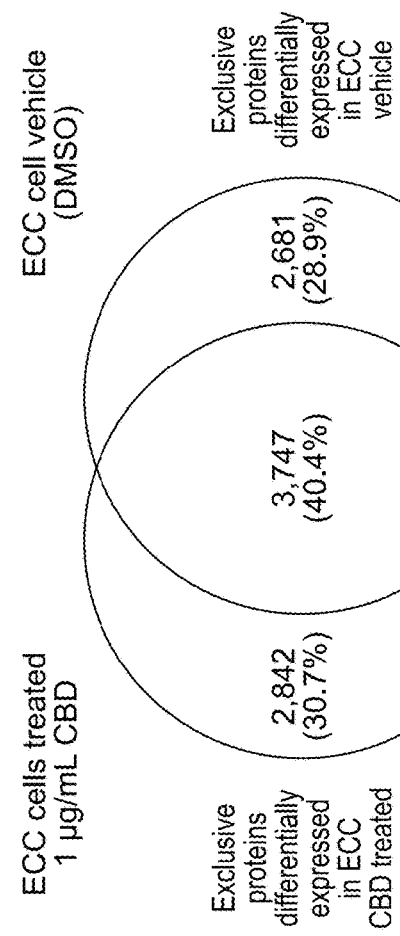

Given the widespread presence of the ECS in the mammalian body, and particularly in the reproductive system, the effects of a cannabis extract (CE) including CBD on gynecological cancer cell protein expression was examined. Proteomics is the large-scale study of proteins, where a proteome is the entire set of proteins produced by the sample under investigation. Proteomes will differ from cell to cell and from time to time. Thus, the comparison of protein expression in untreated cells as compared to treated cells provides insight as to which proteins change expression in the endometrial cancer cells and which proteins remain the same. With this knowledge, additional, targeted research may ensue. Referring to FIG. 1A, endometrial cancer cells (ECC) were either treated with a CE with CBD (1 µg/mL) or left untreated as a control (vehicle—DMSO). After treatment, proteins were extracted from the test cells and the control cells and digested for analysis by liquid chromatography (LC) tandem mass spectrometry (MS/MS). Referring to FIG. 1B, the Venn diagram shows the results of LC-MS/MS analysis which is that treated cells expressed 2,842 different proteins than untreated cells, untreated cells expressed 2,681 different proteins than treated cells, and treated and untreated both expressed 3,747 common proteins. Clearly, based on protein expression differences, treatment with as little as 1 µg/mL CE with CBD had a clear impact on proteins that were exclusively expressed and proteins that were no longer expressed. FIG. 1C compares the degree to which certain proteins were expressed (or not expressed) in untreated cells and treated cells.

Figures 1D, 1E:
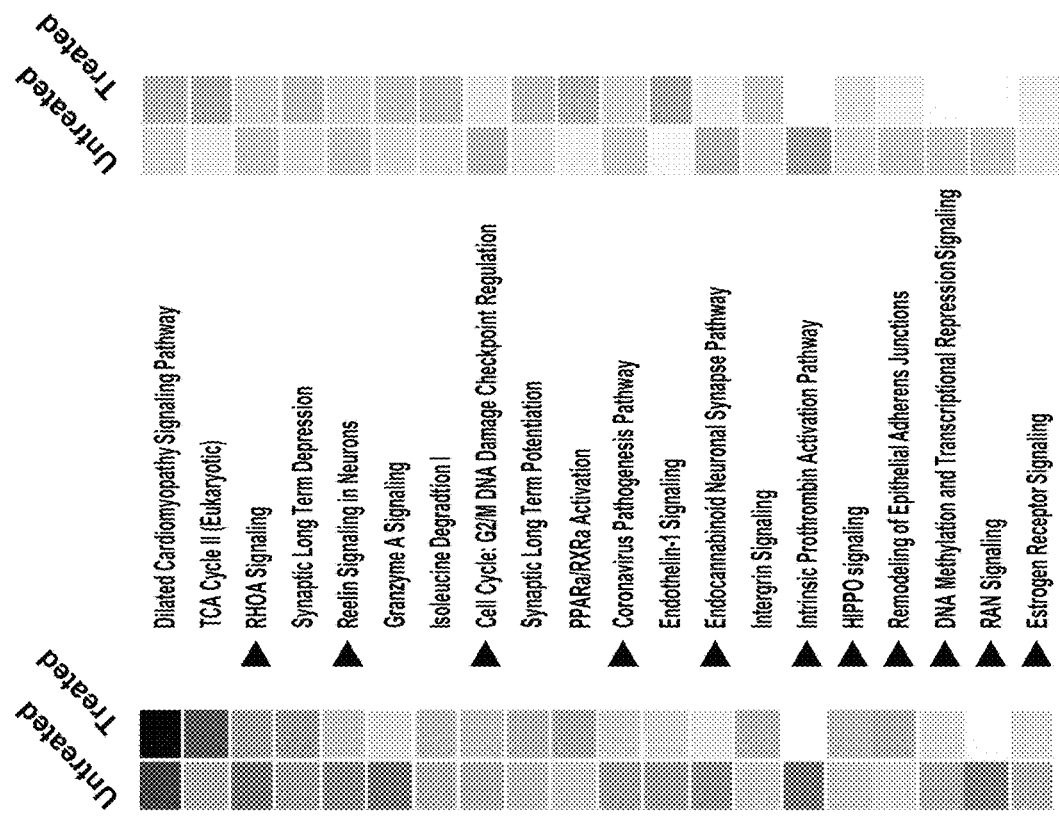
Figure 1G:
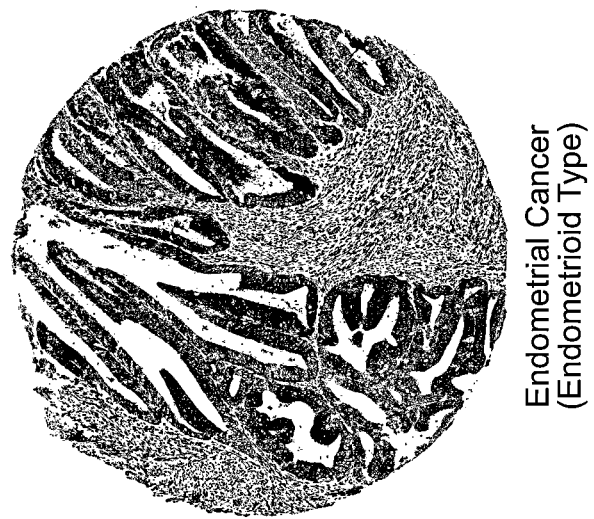

Referring to FIG. 1D, of the thousands of proteins that were differentially expressed with treated and untreated cells, the top 20 upregulated (e.g., in treated cells only) and downregulated (e.g., in untreated cells only), are identified and enumerated. Now referring to FIG. 1E, the effect of treatment with CE with CBD on signaling and trafficking of various physiological and pathophysiological pathways is shown. As one example, proteins associated with Endocannabinoid Neuronal Synapse are shown to be upregulated in untreated cells and downregulated in treated cells. Lastly, referring to FIG. 1F, a tissue sample taken from a patient with endometrial cancer was selectively stained to show CB1 receptor expression. FIG. 1G is a similar tissue sample selectively stained to show CB2 receptor expression.

At about the same time as the above experiments were taking place, the response of organoids derived from ovarian cancers to CE with CBD were also studied. Generally, patients with ovarian cancer were identified and tumor cells were collected. The ovarian cancer tumor cells were used to generate patient derived organoids, the method of which is described below in the Methods section. Calculations for statistical analysis are also provided in the Methods section. As the name suggests, organoids are miniature structures that emulate organs in all their complexity. They are derived from stem cells collected via biopsies and/or resected healthy tissues or tumors. In culture, they self-organized into three-dimensional tissues that mimic the tissues of the individual patient from which they were derived. That is, organoids have the same genetic instructions as the individual from which they were derived and thus demonstrate identical mutations, proliferation, and disease progression as their human counterpart. Organoids can be made to replicate organs with differentiated cell types or to express selected aspects of identified cells of interest. Unlike traditional cell line models associated with high failure rates in clinical trials, organoids' responses precisely and directly translate to human responses. Organoids are well established and have already transformed medical research in providing breakthroughs in treating cystic fibrosis, pancreatic cancer, diabetes, and other diseases. In a simplified example, imagine organoids as clones of an individual's organ. In essence, it is a living, growing avatar of a distinct patient existing outside the body. The avatar will mimic tumor growth and respond to treatment cancer just as it would inside the body. This personalized replica identifies allows for identification of individualized, targeted treatment in a matter of days. It allows a patient to avoid wasting time and risking toxicity with ineffective therapies.

Figure 2A:
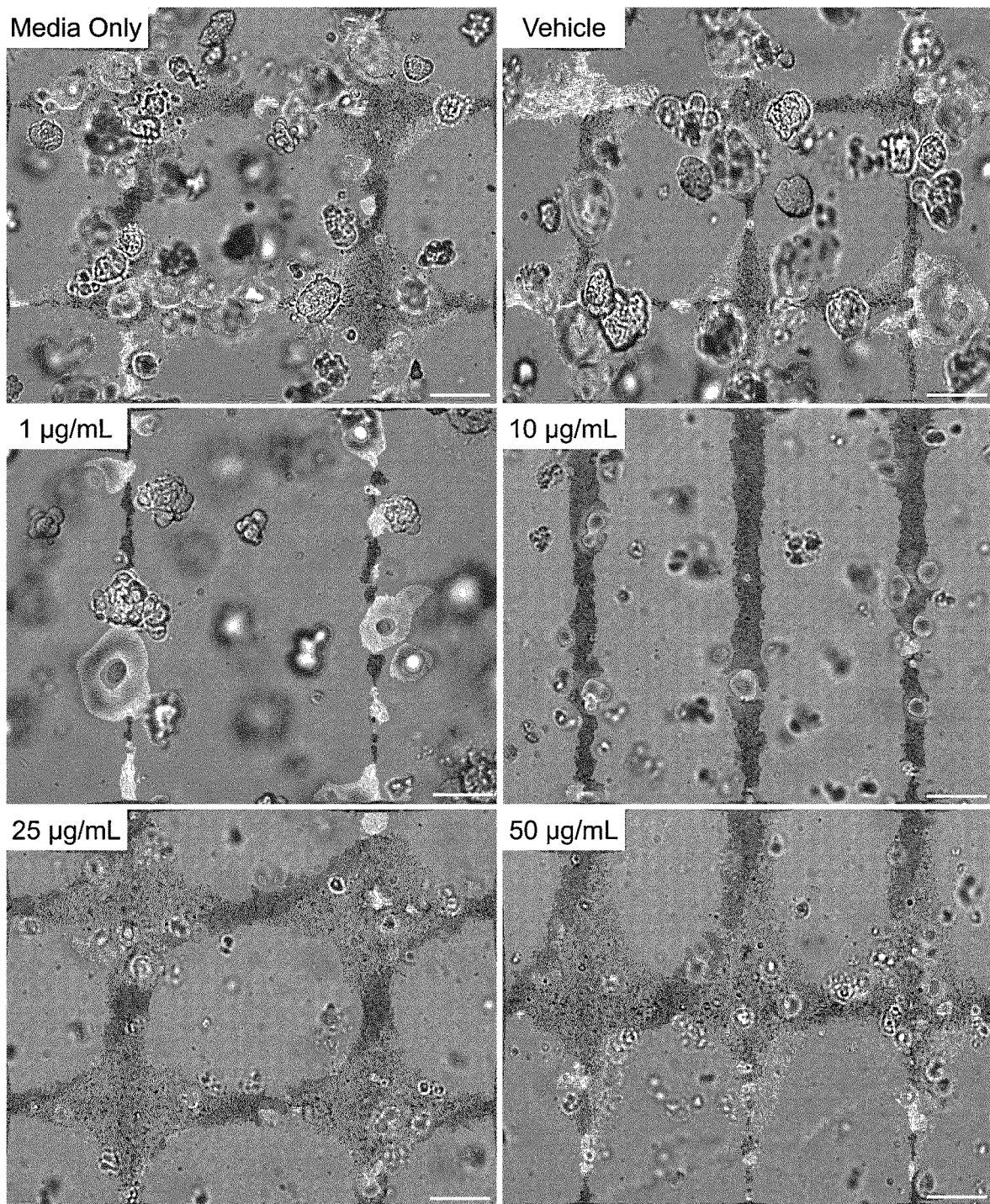
FIGS. 2A and 2B depict chemosensitive ovarian cancer based organoids treated with a cannabis extract, with FIG. 2A depicting cells images treated with varying concentrations of cannabis extract as delivered through a BSHE. Notably, FIG. 2B summarizes the results showing a virtual eradication of the ovarian cancer organoids at as low as 10 μg/mL, and all values above.
Figure 2B:
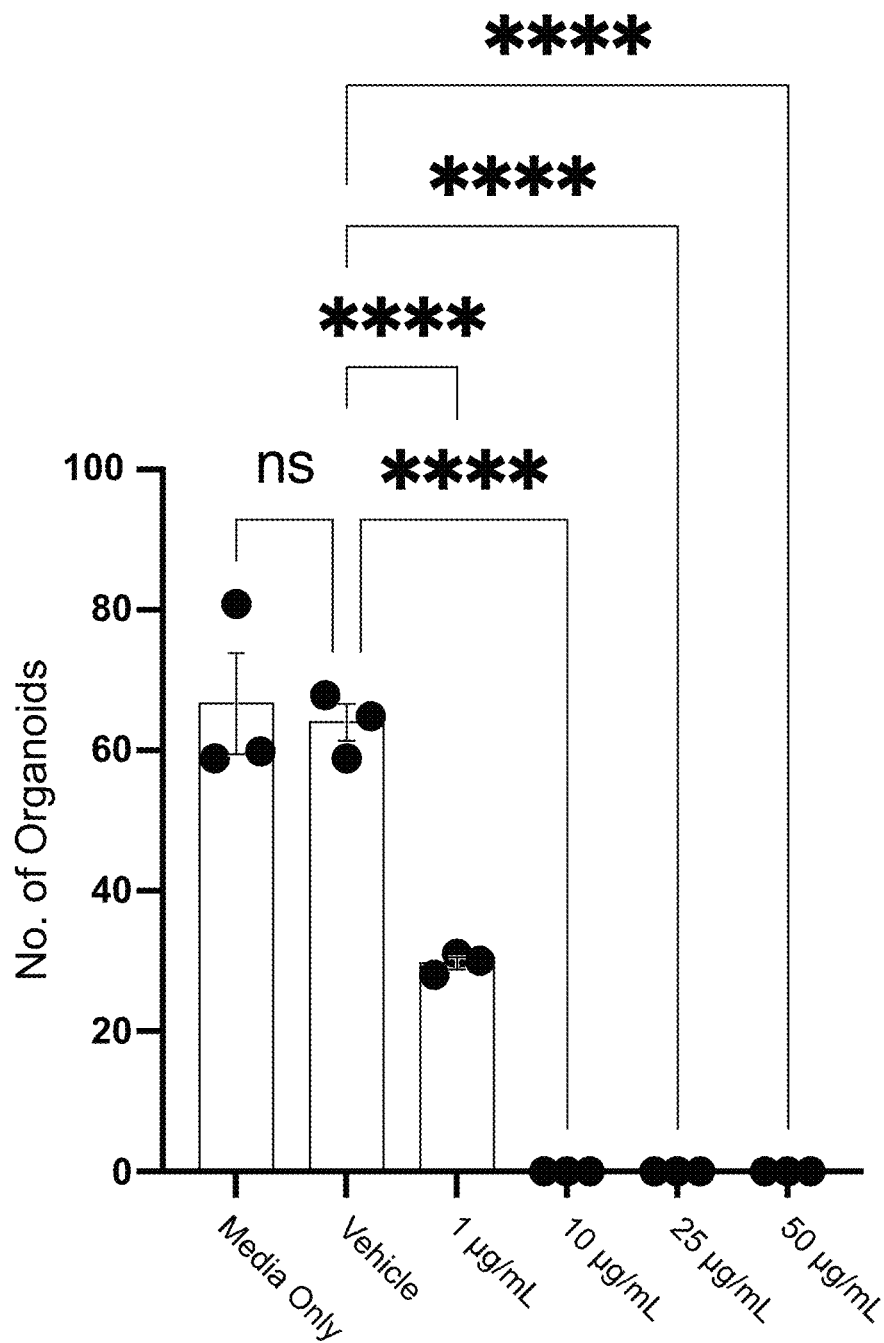

Initial experiments on chemosensitive ovarian cancer organoids used 250 µg/mL of a BSHE comprising CBD as the lowest dose for treatment. This dosage was 100% effective in killing the ovarian cancer organoids, which was certainly unexpected. Subsequent experiments used 100 µg/mL of the BSHE as the lowest dose for treatment. Again, 100 µg/mL was 100% effective in killing the ovarian cancer organoids. Thereafter, the chemosensitive ovarian cancer organoids were treated with lower doses of the BSHE, with 50 µg/mL as the highest dose tested. As can be seen in FIG. 2A, the chemosensitive ovarian cancer organoids were treated with media only, which is the growth media in which the organoids were grown, the vehicle, which is the just the solvent used to deliver the BSHE to the other organoids, and then test dosages of 1 µg/mL, 10 µg/mL, 25 µg/mL, and 50 µg/mL, each concentration being delivered the vehicle. As can be in FIGS. 2B (and 2A) the vehicle and the dosage of 1 µg/mL had nearly the same number of organoids. But at a concentration as low as 10 µg/mL BSHE was able to completely kill the ovarian cancer organoids. The higher doses of BSHE at 25 µg/mL and 50 µg/mL also showed a 100% kill rate of the ovarian cancer organoids. Each of the tests of FIG. 2 were run at least in triplicate, including the vehicle alone, which was dimethyl sulfoxide (DMSO). FIG. 2 thus shows that patient derived organoids, being treated with a vehicle, 1 µg/mL, 10 µg/mL, µg/mL, and 50 µg/mL are effective at treating ovarian cancer.

These doses can then be extrapolated to yield a human equivalent CBD of: 1 µg/mL is a dose of approximately 20 mg a day of CBD, 10 µg/mL is approximately 200 mg a day, 25 µg/mL is approximately 500 mg a day, and 50 µg/mL is approximately 1000 mg a day. Currently, for example, the prescribed CBD isolate is given at a dose of between 5 and 50 mg of CBD/kg and in the United States an average weight of between 65 and 85 kg, yields doses of between 325 to 4250 mg a day of CBD. Applicant's actual tests, therefore, range from well below these doses to about ¼ of the acceptable dose. Applicant believes that the higher end of the human dosing range is fully appropriate in this case as well, which would replicate tests at 100 µg/mL or higher, as the alternative to such CBD dose is almost always chemotherapy, which will have a significantly worse side effect profile at virtually any concentration, than the highest doses of CBD.

Figure 3A:
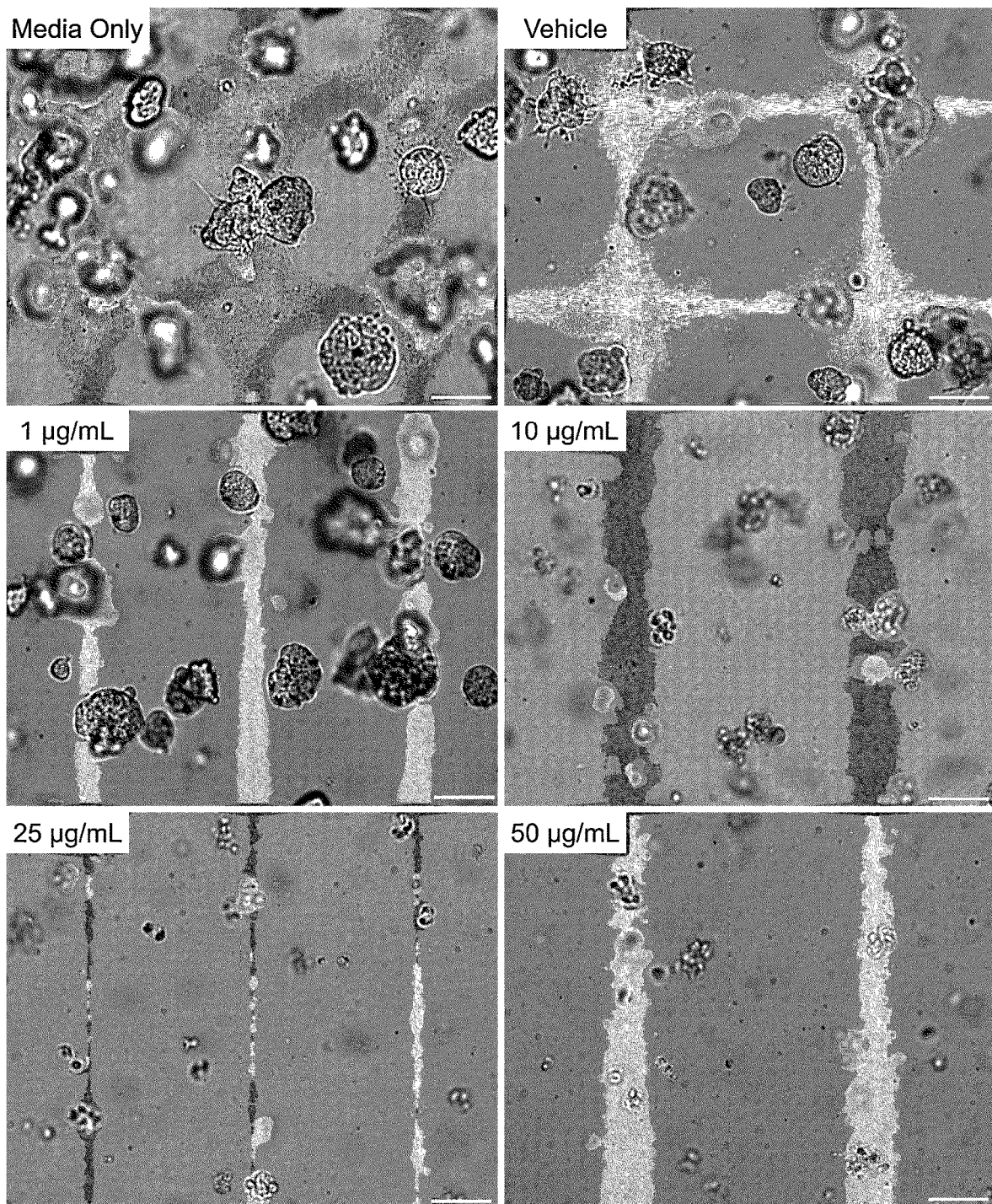
FIGS. 3A and 3B depict a chemoresistant ovarian cancer based organoids treated with a cannabis extract, with FIG. 3A depicting cells images treated with varying concentrations of cannabis extract as delivered through a BSHE. Notably, FIG. 3B summarizes the results showing a virtual eradication of the ovarian cancer organoids at as low as 10 μg/mL, and all values above.
Figure 3B:
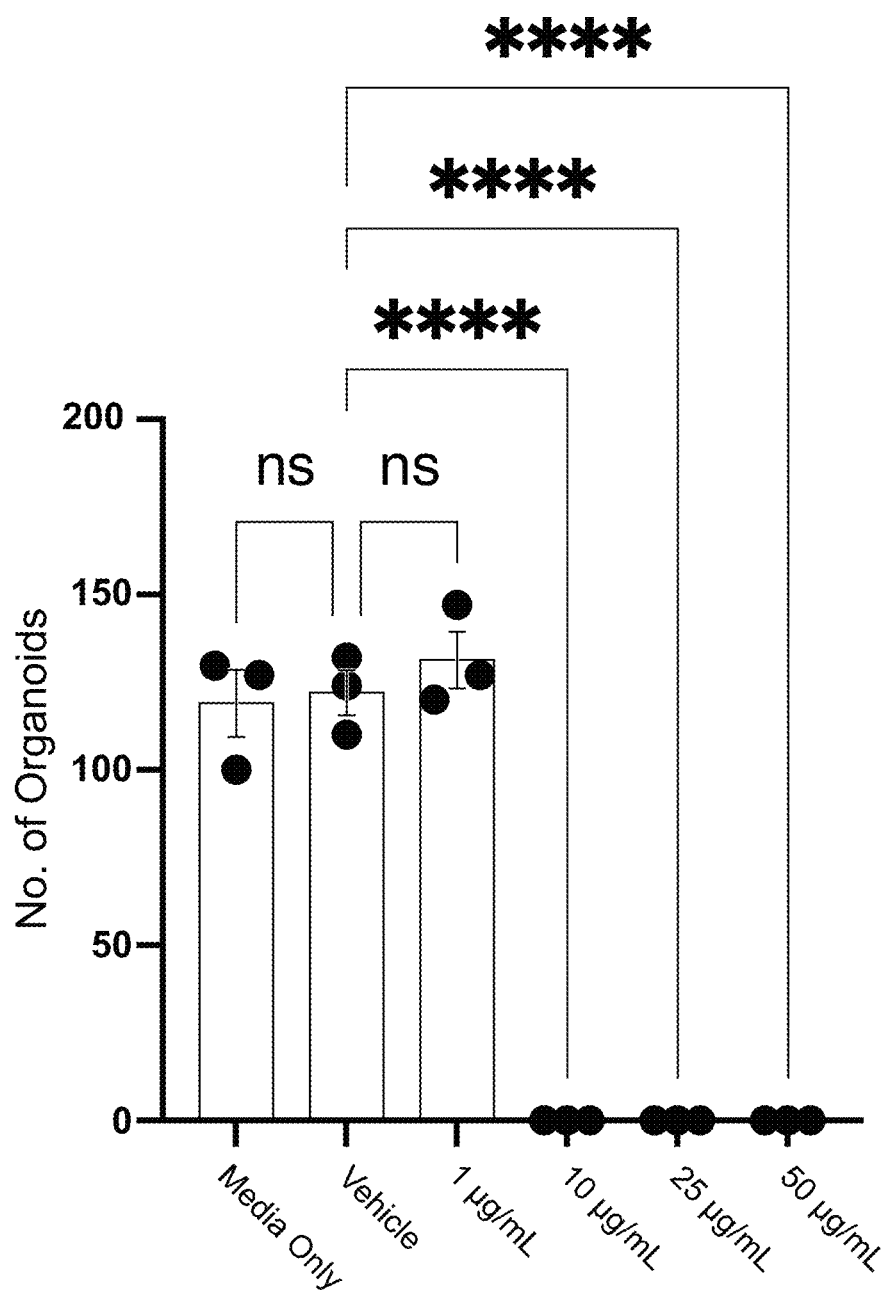

Surprisingly, administering a cannabis extract comprising CBD was effective at all doses at 10 μg/mL and above for killing all organoid (cancerous cells) within the initial study at for the chemosensitive ovarian cancer organoids. However, many forms of ovarian cancer are chemoresistant and thus may respond differently. FIGS. 3A and 3B repeated the same test with chemoresistant ovarian cancer organoids to confirm efficacy. Notably, FIG. 3A details both the media only (showing some of the background material), as well as the DMSO vehicle treatment control. While a concentration at the lowest amount, 1 μg/mL was ineffective as compared to control, upon treatment with 10, 25 or 50 μg/mL concentration of the BSHE comprising CBD in DMSO, the organoids were completely destroyed. The images shown in FIG. 3A and the summary of the data in FIG. 3B paints a complete picture of successful treatment of the organoid removal by treatment of cannabis extract comprising a quantity of CBD of 10 μg/mL or higher.

Figure 4B:
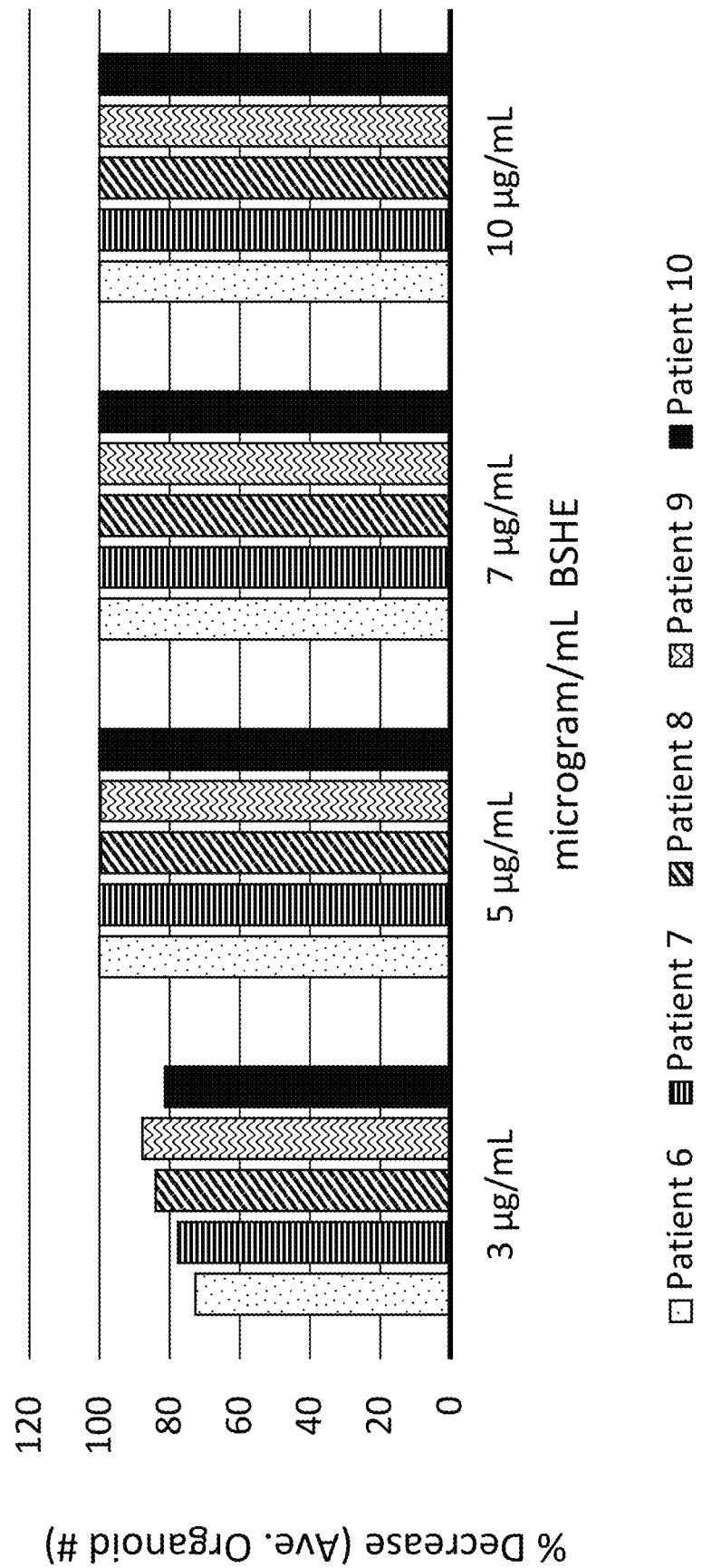

In order to provide for an optimized treatment, drug products seek to identify the lowest dose for providing therapeutic efficacy. Here, therapeutic efficacy is reduction in the number of viable organoids close to or at zero, thus having a 100% decrease in the number of organoids. In view of the surprising results, Applicant then further decreased the dose to determine if a lower dose would also continue to be effective for additional samples. Accordingly, additional ovarian cancer organoids were created from several patients, including those corresponding to high grade ovarian cancer. FIGS. 4A and 4B detail that in the high grade ovarian cancer organoids, dosing as low as 4 μg/mL was effective in reducing the percent of organoids to virtually zero. Indeed, at amounts of 5, 7 and 10 μg/mL doses of BSHE, all of the samples showed a 100% reduction in the number of organoids, while at 4 μg/mL, these numbers averaged nearly 98% reduction in organoids across all samples. Accordingly, for the particular set of patients, therapeutic treatments comprising a cannabis extract comprising CBD was effective in decreasing the number of organoids in high grade ovarian cancer by more than 95% at dose as low as 4 μg/mL and was able to reduce the number of organoids by 100% at a dose of 5 μg/mL.

Thus, CBD as applied through a CE was thus effective in destroying the organoids in ovarian cancers. This response held regardless of the severity or grade of the cancer. Therefore, application of cannabis extracts comprising CBD are effective in reducing the number of viable patient derived organoid cells from ovarian cancer.

The BSHE used in all prior tests, is just one formulation of a cannabis extract. As further detailed in the methods section, processes for manufacturing the BSHE can be modified to yield additional products, including but not limited to a full spectrum hemp extract (FSHE), which contains preferably 0.01 to 0.3% but up to about 5% of $\Delta^9$-THC, and usually less than of $\Delta^9$-THC. Another product is an isolated CBD, and finally an isolated produce of the acid form of CBA, cannabidiolic acid (CBDA).

Figure 5B:
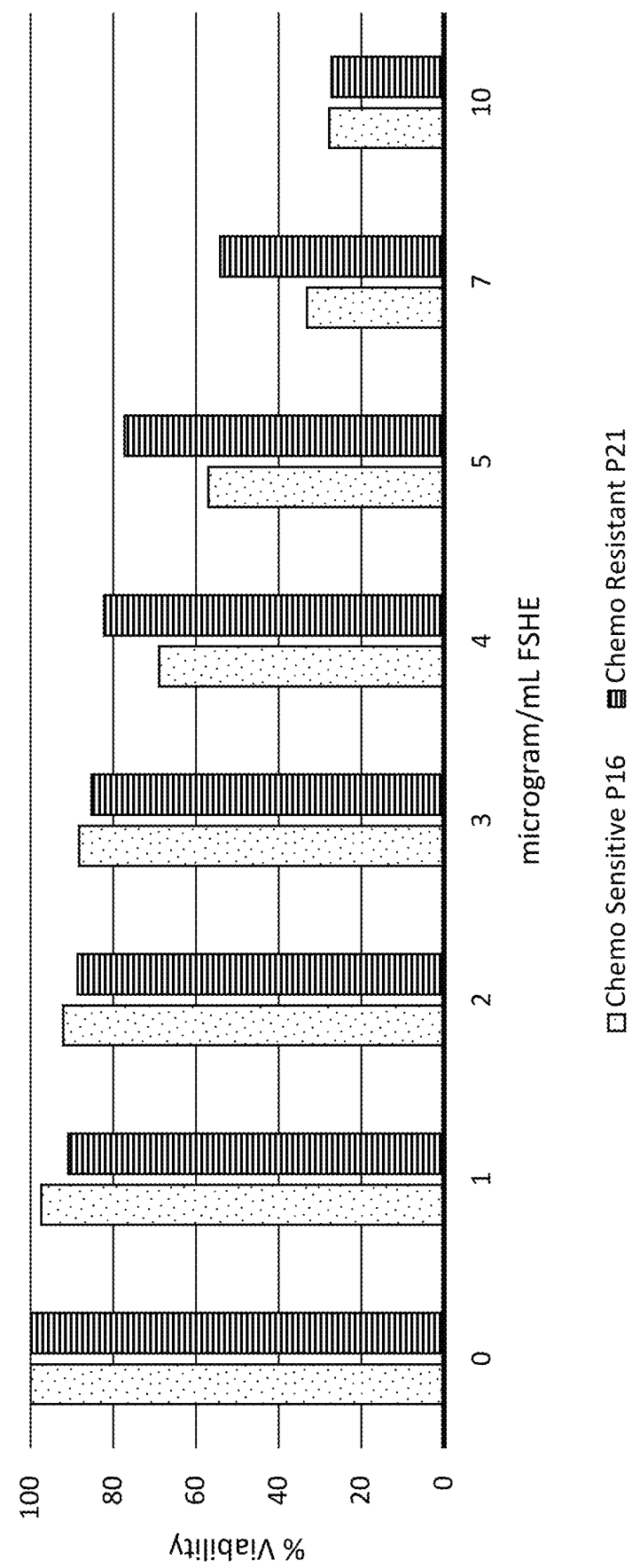
Figure 5D:
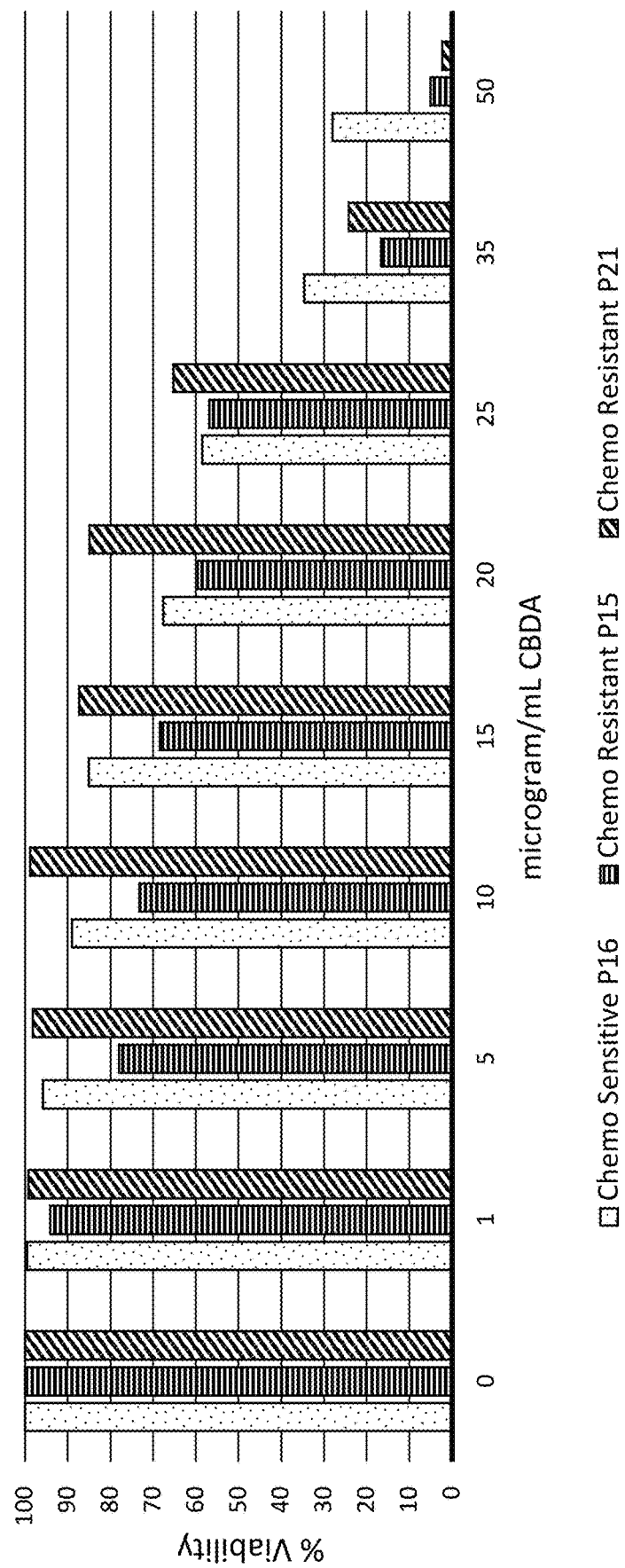

Applicant then tested several different cannabis extracts at varying concentrations on newly obtained patient derived chemosensitive and chemoresistant ovarian cancer organoids. FIG. 5A shows the results related to BSHE, FIG. 5B shows FSHE, FIG. 5C shows CBD isolate, and FIG. 5D shows CBDA. Here, the BSHE continued to work at virtually the same level as prior tests, even though these organoids were generated from different patients than all prior tests. The data simply shows some slight variability in response rates across patients, which is typical for any drug product. However, what remains constant is that at or about 10 μg/mL, virtually all patient derived organoid samples begin to or reach zero viability. However, as not all reached 0% viability, additional tests were performed at 15 and 20 μg/mL for the FSHE and the CBD isolate, which showed that all samples had 0% viability at both 15 and 20 μg/mL, except for those related to CBDA. CBDA was then extended to 15, 20, 25, 35, and 50 μg/mL, with only values at 50 μg/mL nearing zero viability as with the other test products.

The studies, therefore, show that ovarian cancer organoid cells are highly susceptible to the various cannabis extracts and that administering an effective amount of the cannabis extract was effective in reducing the number of organoids and eradicating them in all but a few examples. Accordingly, based upon the successful determination that cannabis extracts comprising a therapeutic amount of CBD are effective in treating organoids from ovarian cancer cells, Applicant wanted to extend this confirmation to mouse models, in patient derived xenograft studies. These xenograft studies confirm that the dosing is consistent between organoids and mouse models, as well as that systemic delivery is successful at treating the cancerous cells.

Figure 6:
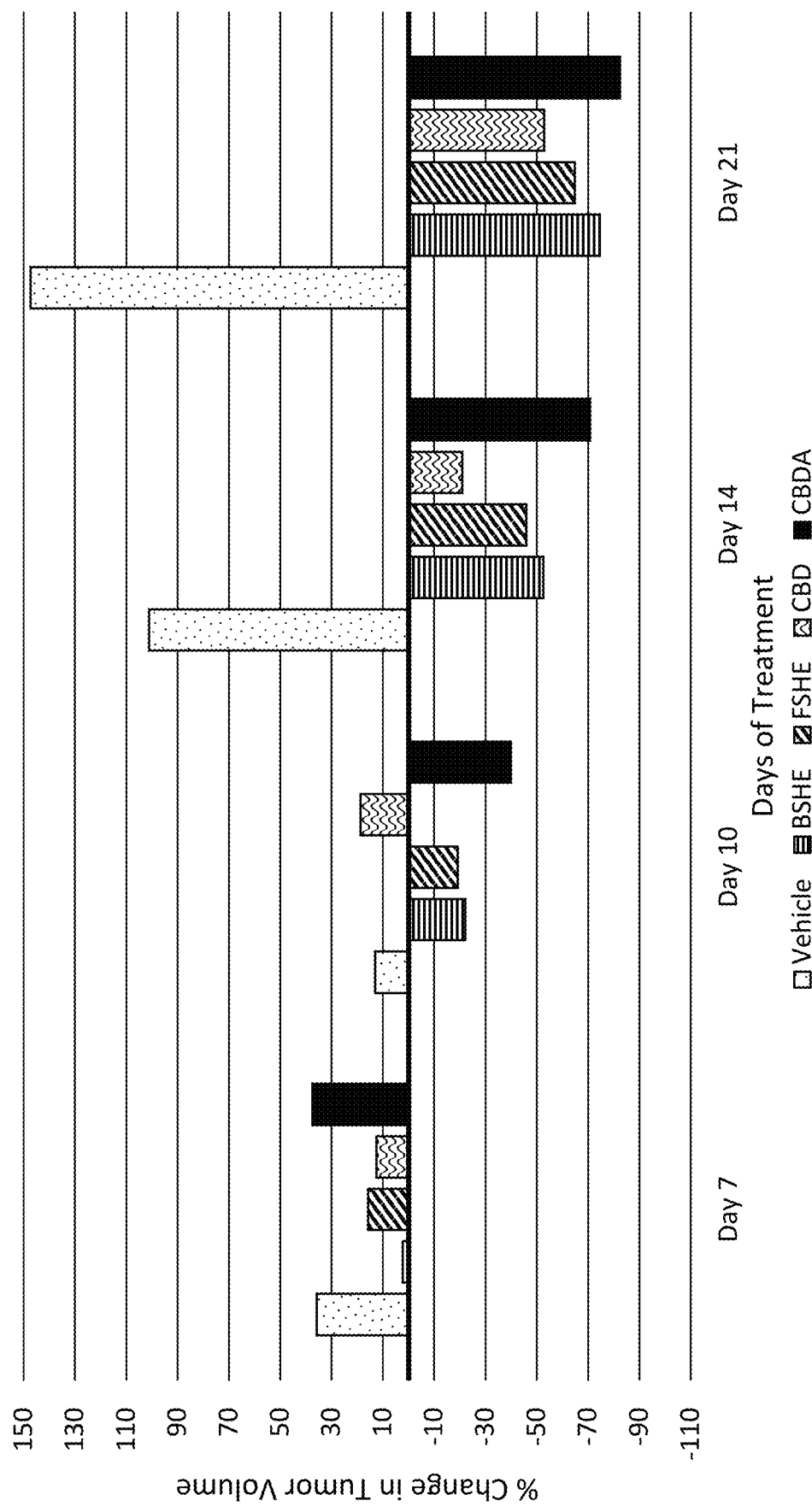
FIG. 6 depicts a graphical chart of endometrial cancer tumor volumes within mice, wherein the mice were injected with patient derived endometrial cancer cells. Endometrial cancer organoids were shown to be analogous in response to the ovarian cancer organoids and used for this particular model. The data shows the change in tumor volume from day 7 to day 21 and depicting the therapeutic efficacy of the various cannabis extracts on the tumor volumes.

Mouse studies are useful to take cell-based applications and confirm their efficacy in a whole animal system. Furthermore, the mice allow for testing of systemic application of the drugs. Mice were generated and tested according to the methods section detailed below. Mice were then injected, via intraperitoneal dosing, with various formulations of cannabis extracts comprising a known quantity of CBD, or a vehicle, with the results being compared to the volume at T=0 for each of the mice. Dosing was 30 mg/kg of each of the cannabis extracts, FIG. 6 depicts the results over the 21-day period using endometrial cancer cells injected into the mice. In each case, the mice models showed that tumor growth ranged between a slight decrease or slight growth over the first 7 to 10 days, before the tumors as a whole begun to decrease in size. By day 14, in comparison to the control, each of the tumor volumes were at or below their day 0 volume, with significant decreases seen in each of the different cannabis extracts as compared to volume at days 7 and 10. Finally, by day 21, tumor sizes for all of the treated samples were dramatically reduced as compared to both of their original volume and also as compared to control.

The data in FIG. 6 is really shocking in its efficacy. The control mice, receiving only the vehicle, show tumor growth of nearly 150%. By contrast, each of the four treated examples, show a decrease in tumor volume of between 53 and 82%. The differences are literally life and death, as the control tumor reaches a size that requires ethical sacrifice of the animals, while the treated animals show virtually no tumor after just 21 days of treatment. This reaffirms the prior organoid studies, which showing that cancer tumors, specifically, those of endometrial cancer and ovarian cancer, are susceptible to treatment with cannabis extracts comprising CBD. Accordingly, Applicant confirms that use of a cannabis extract is suitable to reduce tumor volume, and to reduce viability of tumor cells across several different models.

Notably, the concentration of CBD used in each case remains on the low end of the therapeutic dose suitable for administering to a human patient, or to a mouse. The low doses were utilized in order to show impact of the cannabis extracts, instead of each of the data going to zero, by using double, triple, or higher of the dose as administered to the mice, all of which would be appropriate human equivalent doses. Even with the lower dosing, at time of 21 days, virtually all of the samples are progressing tumor volume toward zero, and in one case, the tumor volume has reached zero at day 21. Therefore, when comparing these quantities to those from the organoid data, we see that each sample retains the efficacy from the organoid data in treating cancerous growths via systemic administration of CE with certain concentrations of CBD. Thus, administering cannabis extracts is effective in greatly slowing the growth of endometrial cancer tumors, which serve as the model for ovarian cancer, in this case, and ultimately reduces the tumor size, which may result in the eradication of tumor cells, by administering the cannabis extracts to the mice.

Combinations with Chemotherapy

Because chemotherapy is often a first-line therapeutic used in treating ovarian cancers, as well as other gynecological cancers detailed herein, the ability to reduce the quantity of chemotherapy, while maintaining its efficacy would lead to a tremendous breakthrough in cancer treatment. We detailed above, that the toxic effects from chemotherapy actually cause death in a significant portion of patients. Furthermore, the acute toxicity of the chemotherapy results in significant damage and morbidity, even when it does not cause immediate death. Thus, we recognize that the ability to obtain effective therapeutic treatments by reducing the amount of chemotherapeutic agents or to reduce the number of chemotherapy cycles, would lead to tremendous improvements in cancer treatment.

Chemotherapy is often given in progressive doses, meaning, it may take more of the chemotherapy drug to obtain the same response, as disease progresses. In many cases, patients progress wherein the ovarian cancer becomes chemoresistant, which requires a change in the chemotherapy agent or a completely new approach toward managing the disease. In view of the successes of the cannabis extract comprising CBD on organoid cells, Applicant questioned whether the combination of CBD with chemotherapeutic agents could lead to a reduction in the quantity of chemotherapeutic agents needed to achieve a reduction in the tumor cells. Therefore, Applicant tested the combination of chemotherapy drugs with a cannabis extract to determine if the combination could reduce the amount of chemotherapy required to obtain therapeutic responses, namely reducing the growth of ovarian cancer cells/tumors and ultimately eliminating the tumors.

Several chemotherapeutic agents were tested for efficacy against both organoids and then on mice models. Because of the toxic nature of the chemotherapeutic agents, a key metric and value is the ability to generate an equivalent clinical response to the chemotherapy, while using a lower total amount of the chemotherapeutic agent. A simplified example would be that if a normal dose of chemotherapy agent X was 200 mg, resulting in a reduction of tumor size by 90%, then the ability to use the same chemotherapy agent X at a dose of 100 mg and obtaining the same reduction of tumor size by 90% would provide significant benefits to the patient with regards to less secondary damage to healthy tissue, and other known impacts from the chemotherapeutic agent. Here, that result is not simply a 50% reduction in the amount of chemotherapy to yield an appropriate therapeutic response, but by using an amount of five or six times less than the normal chemotherapy dose, combined with a therapeutically effective dose of a cannabis extract, yielded a stronger therapeutic response that arrested tumor growth and reduced ovarian cancer organoids, as well as reduced tumor volume in mice models than the chemotherapeutic agent alone.

FIG. 7A details the use of paclitaxel in combination with a cannabis extract in treating chemosensitive ovarian cancer cells, which was derived from ascites cells. FIG. 7 shows a control dose, meaning only the cannabis extract products, given at 50% inhibitory concentration (IC50). IC50 is conventionally used to determine drug potency with cell-based toxicity tests. Here, the amounts are 5.5 μg/mL for the BSHE and 5.8 μg/mL for the FSHE. The paclitaxel is administered at 4 nm/mL and also at 20 nm/mL in combination with the cannabis extracts. Notably, the paclitaxel was also tested at 8, 12, and 16 nm/mL, with only moderate changes in a near linear fashion, and are thus not depicted in the drawing.

What is striking about the results of FIG. 7A, is that taking the first dose of paclitaxel and increasing that dose by 5×, results in a relative reduction in viability from about 89% for the organoids at 4 nm to only about 57% for the 20 nm/mL dose. While significant, the change of 32% still leads to an overall kill rate of less than 50% at the highest dose for paclitaxel alone. However, in view of the significant toxicity, such minimal gains and a large multiplier of the dose, shows the weakness of the paclitaxel alone. The gains pale in comparison to what is evident from using the lowest dose of paclitaxel, with an IC50 dose of any of the cannabis extracts, reducing the viability by nearly 60% with just the 4 nm/mL. Indeed, even paclitaxel at nm/mL alone had a 30% less kill rate the 4 nm/mL paclitaxel dose with a small amount of either of the BSHE or the FSHE. Thus, it would be more advantageous to administer the lowest dose of paclitaxel with a dose of cannabis extract instead of increasing the dose of the paclitaxel. Accordingly, by taking an IC50 dose of any of the cannabis extracts and administering it concurrently with the paclitaxel, a surprising synergy was identified, which could dramatically reduce the amount of paclitaxel needed to achieve low to no viability for the endometrial cancer organoids.

Figure 7B:
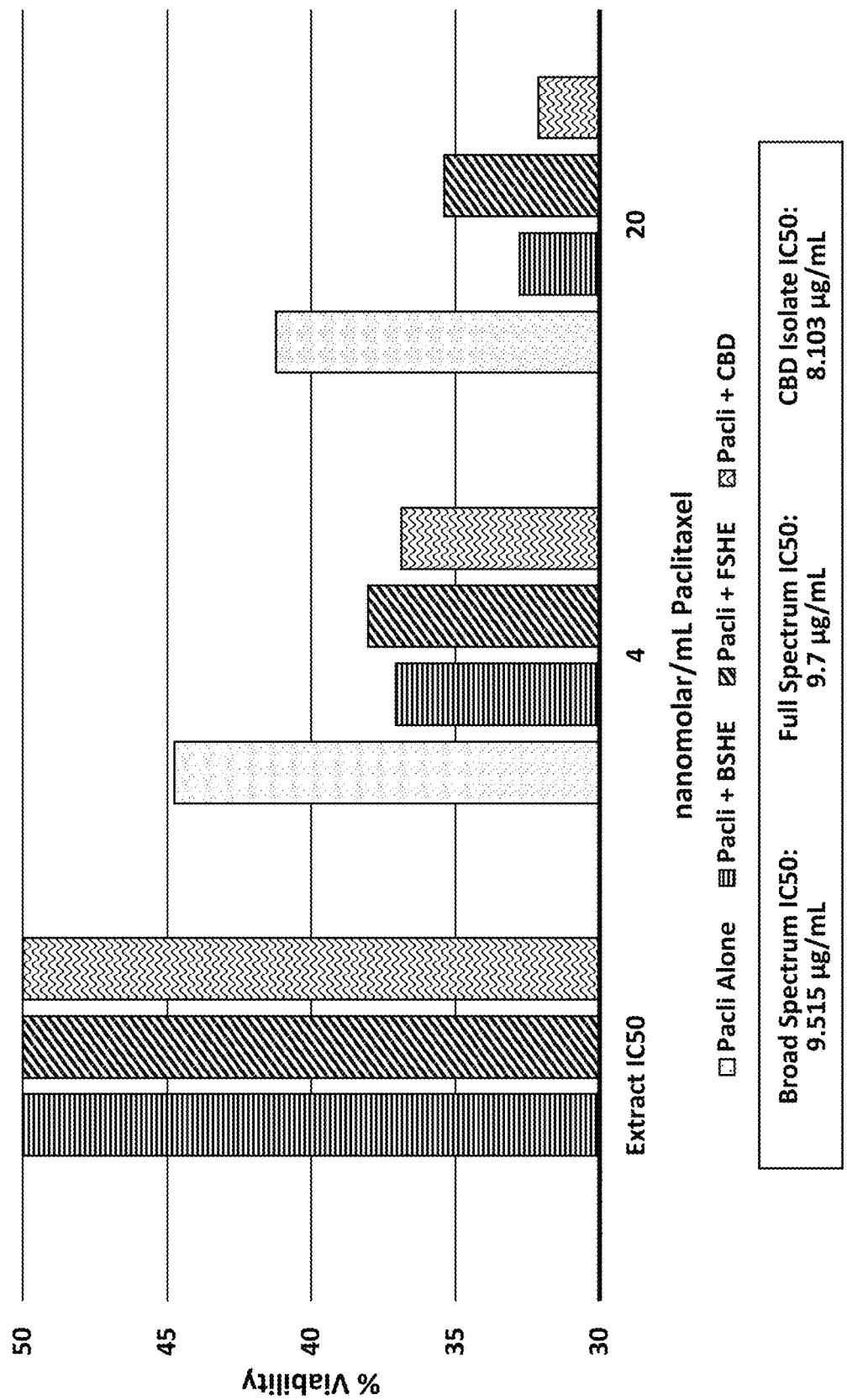

FIG. 7B then repeats the test from FIG. 7A for a chemoresistant ovarian cancer organoid. Here, the paclitaxel has a viability of 45% for 4 nm/mL, but by adding just an IC50 amount of cannabis extract, the numbers drop by almost 10% viability. Compare that to adding more of the paclitaxel alone, which only changes viability by about 3% total to a 42% viability. Thus, use of the lower amount of paclitaxel with a small amount of the cannabis extract shows a surprising synergy, that it kills dramatically more of the chemoresistant organoids than paclitaxel alone at low or high doses. Based on the response from FIGS. 7A and 7B, the combined chemotherapy is vastly superior than the chemotherapeutic drug alone.

To determine if this premise is conserved over different chemotherapeutic agents, Applicant repeated the tests replacing paclitaxel with carboplatin toward a related gynecological cancer cell, endometrial cancer cells. The surprising findings with paclitaxel were further confirmed by testing the impacts of carboplatin alone or carboplatin with a cannabis extract. In FIG. 8, three different cannabis extracts were tested, a BSHE a FSHE, and a CBD isolate each at IC50 concentrations. The story as detailed for paclitaxel is repeated for carboplatin, which is another first line chemotherapeutic agent for ovarian cancers, and leads to dramatic reduction in viability of patient derived organoids, when combined with a cannabis extract comprising CBD.

As depicted in FIG. 8, by administering carboplatin to the organoids at 50 and 100 μg/mL, a reduction in viability remains virtually unchanged at about 50%, while dosing with an IC50 amount of cannabis extract reduces viability to at or below 20% for two of the cannabis extracts, while the dose at 100 inn/mL reduces viability to at or around 20 for one of the cannabis extracts with the others at about 15% and the last at under 10% viability. Here, BSHE was used at 2 µg/mL, FSHE at 4.5 µg/mL and CBD isolate at 3 µg/mL for their IC50 doses. Finally, with a dose of 250 µm/mL carboplatin, a 2.5× in the dose from the 100 µm/mL test, all of the combined therapeutics with carboplatin and cannabis extract are below 10% viability, while the carboplatin alone remains at above 30%. In each case, administering 2.5× less or even less than carboplatin at 250 µm/mL yields a superior result in all but one test, when simply adding to the treatment protocol, an IC50 amount of a cannabis extract.

Said a further way, the impacts of doubling the dose of carboplatin changed the percent viability by about 1%. Further, taking the original 50 µm/mL dose and increasing it by only resulted in a total drop of about 17% in viability. The increase in carboplatin by 5×, as detailed herein, provides for significant risk to morbidity and even increases risk of mortality due to high concentrations of the chemotherapy. By contrast, taking the lowest carboplatin dose and adding an IC50 amount of the BSHE or the FSHE results in a 26% drop in viability with a BSHE and a 37% drop in viability with a FSHE. While the CBD isolate still performed significantly better than the isolate alone, its combination at the lowest level yielded about a total of 37% viability, still a sizeable drop. When doubling the carboplatin then yields only a 2% improvement in viability, adding the CBD to the 100 µm/mL dose, shows a 21% improvement with BSHE, a 39% improvement with the FSHE and a 32% improvement with the CBD isolate. The results at the highest carboplatin dose continue to show the therapeutic efficacy of a combined treatment, with all combinations below 10% viability, and approaching zero, while the carboplatin alone is at 32% viability.

In each of these organoid tests, the results show an unexpected synergy and dramatic improvements in the amount of chemotherapy required to clinically treat cancers. Combining cannabis extracts with chemotherapy allows for at least a 5× reduction in the use of the chemotherapeutic agent to obtain the same efficacy, if simply combined, or coadministered with a cannabis extract at IC50 values.

The impacts of the combination of chemotherapy and the cannabis extract comprising CBD were highly successful, showing that dramatically less chemotherapeutic agent could be utilized when combined with one of the cannabis extracts comprising CBD. To confirm the efficacy of the study within a systemic approach, mice were grown, according to the methods below, and tested for paclitaxel alone and then paclitaxel with the cannabis extracts.

FIG. 9 details the results of mice tumor volume comparing paclitaxel alone to those treated with a combined paclitaxel and a cannabis extract. The control, or no treatment is not shown in FIG. 9, but resulted almost 150% growth over the 21 days, as compared to the initial tumor volume. What is striking is what was seen in the organoid data and then repeated here, by combining a low dose of paclitaxel with an effective dose of any of the cannabis extracts yields dramatically greater reduction in tumor volume as compared to the paclitaxel alone or even the cannabis extracts alone at the given dose. Thus, coadministration of the hemp extract comprising a known amount of CBD with the carboplatin or with the paclitaxel was surprisingly more effective than their administration alone.

FIG. 9 utilized a dose of just 10 mg/kg, which can be adjusted to 30.007 mg/m$^2$ of Paclitaxel, and the clinically recommended human dose of Paclitaxel is 175 mg/m$^2$. The paclitaxel only dose was, in essence ineffective after an initial reduction at day 10, as over the course of the remaining 11 days, the tumor volume in the paclitaxel only mice was not reduced. However, the stasis of the paclitaxel only dose is in stark contrast to the paclitaxel combination with CE. Each of the CE products was administered at a concentration of 30 mg/kg, yielding an effective dose of 170.1 mg/day human equivalent. In each of the treatments combining the paclitaxel dose with any of the different cannabis extracts, by day 21, each of the tumor volumes for these combination treated mice were at least 20% better in the change in tumor volume than the paclitaxel alone mice. Indeed, for three of the cannabis extracts, the results were almost 40% better in the change in the tumor volume, yielding tumor volumes at almost 80% less than their initial treatment volume, and rapidly moving toward complete reduction of the tumor. Thus, administering almost V6 of the normal indicated dose of paclitaxel and administering that with 30 mg/kg body weight amount of CE resulted in unexpected synergy in reducing tumor volume within the mice. The difference shows on one-hand, an ineffective treatment with chemotherapy alone, or resulting in nearly complete eradication of the tumors over the 21-day period, simply by administering the same paclitaxel dose with a cannabis extract. This synergy would allow for paclitaxel to be administered at V6 of its normal effective dose, if combined with the cannabis extract comprising CBD. Such a reduction in the Paclitaxel dose will reduce unnecessary side-effects of chemotherapeutic agents, and with the joint administration, provide dramatically increased efficacy.

Because of the significant toxicity and damage from chemotherapy, the reduction in the amount of chemotherapy that a patient receives significantly reduces short- and long-term morbidity and often reduces mortality rates. The side effects of chemotherapy are often chronic and include damage to major organs and organ systems, such as the brain, central and peripheral nervous systems, heart, lungs, liver, gastrointestinal tract, and reproductive tract. Chemotherapies can even result in secondary cancer over time. Further, chemotherapy is fatal, particularly when used in higher doses. A recent study evaluating this effect concluded that chemotherapy or its side effects directly caused or hastened death in 27% of patients. Additionally, 43% percent of patients in the study suffered significant treatment-related toxicity within just 30 days of receiving chemotherapy and a full 25% of such patients die from the treatment-related toxicity. The data is particular compelling when the study determined that 19% of all deaths were linked to patients who should not have received chemotherapy at all.

Thus, mitigating chemotherapy-related toxicity, and reducing the chemotherapy dosing is critically important, as treatment with high doses of chemotherapy are indiscriminate and damage these cells, when given over time. Thus, reduction in the quantity of chemotherapy drugs, whether at lower doses or none, in combination with the cannabis extract can improve the outcome for patients by decreasing tumor volume at a greater rate, reducing the tumor volume to a greater total percentage than chemotherapy alone, and does not otherwise cause damage to the corresponding, healthy tissues of the reproductive tract and the liver as would occur from chemotherapy use.

Combining cannabis extracts with chemotherapy results in a six-fold dose decrease in the toxic treatment required for effective treatment in mice. When used alone, 30.007 mg/m$^2$ of Paclitaxel was ineffective in reducing tumor growth. However, using exactly the same 30.007 mg/m$^2$ of Paclitaxel dose (instead of 175 mg/m$^2$ as required for paclitaxel alone human dosing) was effective in reducing tumor growth, but only when combined with a cannabis extract comprising CBD. The organoid data, was equally impressive, as adding 2× or 5× of either chemotherapy was less effective than simply adding an IC50 amount of CE with CBD to the lowest chemotherapy dose.

In view of the organoid and mice data, providing an effective amount of a cannabis extract, alone or in combination with a chemotherapeutic agent will provide synergy to the combined therapy, or can provide therapeutic efficacy on its own. And this is immensely valuable, as reducing the dose of chemotherapy will reduce acute and long-term toxicity to patients utilizing chemotherapy as a first-line treatment. The impact on a reduction in toxicity is that healthy cells will show reduced damage, as compared to high levels of chemotherapy treatment.

Figure 10A:
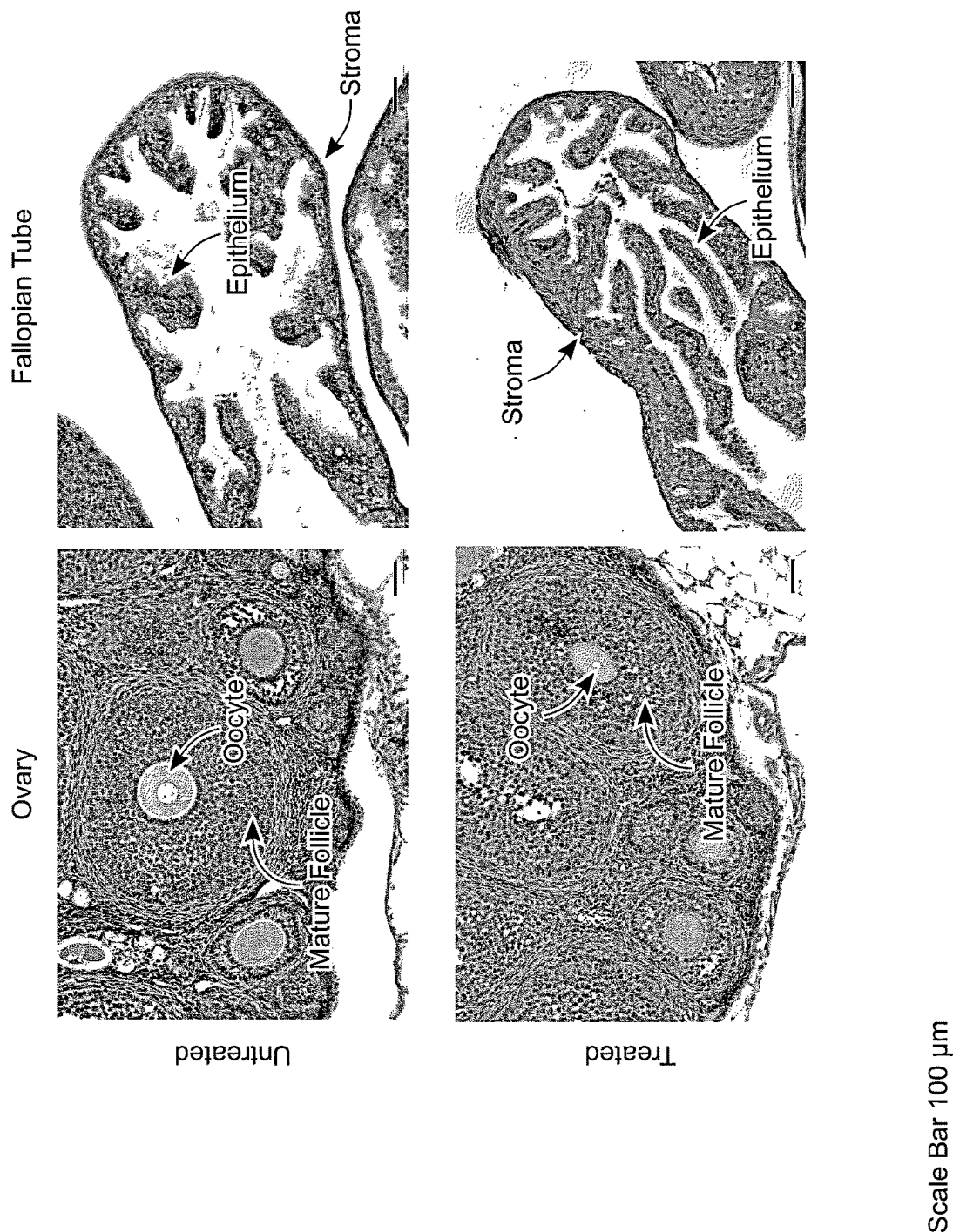

Of primary importance is also the impact of the therapeutic levels of cannabis extract on healthy tissues. While not depicted, even small amounts of chemotherapy cause significant damage to healthy cells. This is widely understood in the literature and is a significant cause of morbidity and mortality from the chemotherapy. FIGS. 10A and 10B show histopathology taken from the mice models of treated and untreated mice, showing that treating the mice with cannabis extracts does not damage the cells of the ovary and fallopian tube in FIG. 10A and the uterus, vagina, or the liver in FIG. 10B. This evidence confirms the absence of toxicity in the cannabis extracts comprising CBD when treating the mice. In each case, a visual comparison between the untreated and treated tissues shows that cannabis extracts comprising CBD do not cause secondary or ancillary damage to health tissues. However, a further comparison to chemotherapy treated tissues would show significant damage. This is critically important, as treatment with high doses of chemotherapy are indiscriminate and damage these cells, when given over time. Thus, a reduction in the quantity of chemotherapy drugs, whether at lower doses or none, in combination with the cannabis extract can improve the outcome for patients by decreasing tumor volume at a greater rate, reducing the tumor volume to a greater total percentage than chemotherapy alone, and does not otherwise cause damage to the corresponding, healthy tissues of the reproductive tract and the liver as would occur from chemotherapy use.

CBD is non-toxic in non-transformed cells and does not affect physiological parameters (heart rate, blood pressure and body temperature), gastrointestinal transit nor psychomotor or psychological functions. Chronic use and doses up to 1,500 mg/day of CBD are established as well tolerated in humans, with some doses even administered at up to 4,250 mg/day in certain applications. CBD dominant cannabis extracts have no potential for abuse or dependence. This was best highlighted during the World Health Organization's 41st Expert Committee on Drug Dependence held in Geneva, Switzerland in November 2018. Annex 1 from the meeting's report states "cannabidiol should not be scheduled within the International Drug Control Conventions. Cannabidiol is found in cannabis and cannabis resin but does not have psychoactive properties and has no potential for abuse and no potential to produce dependence. It does not have significant ill-effects."

Figure 11:
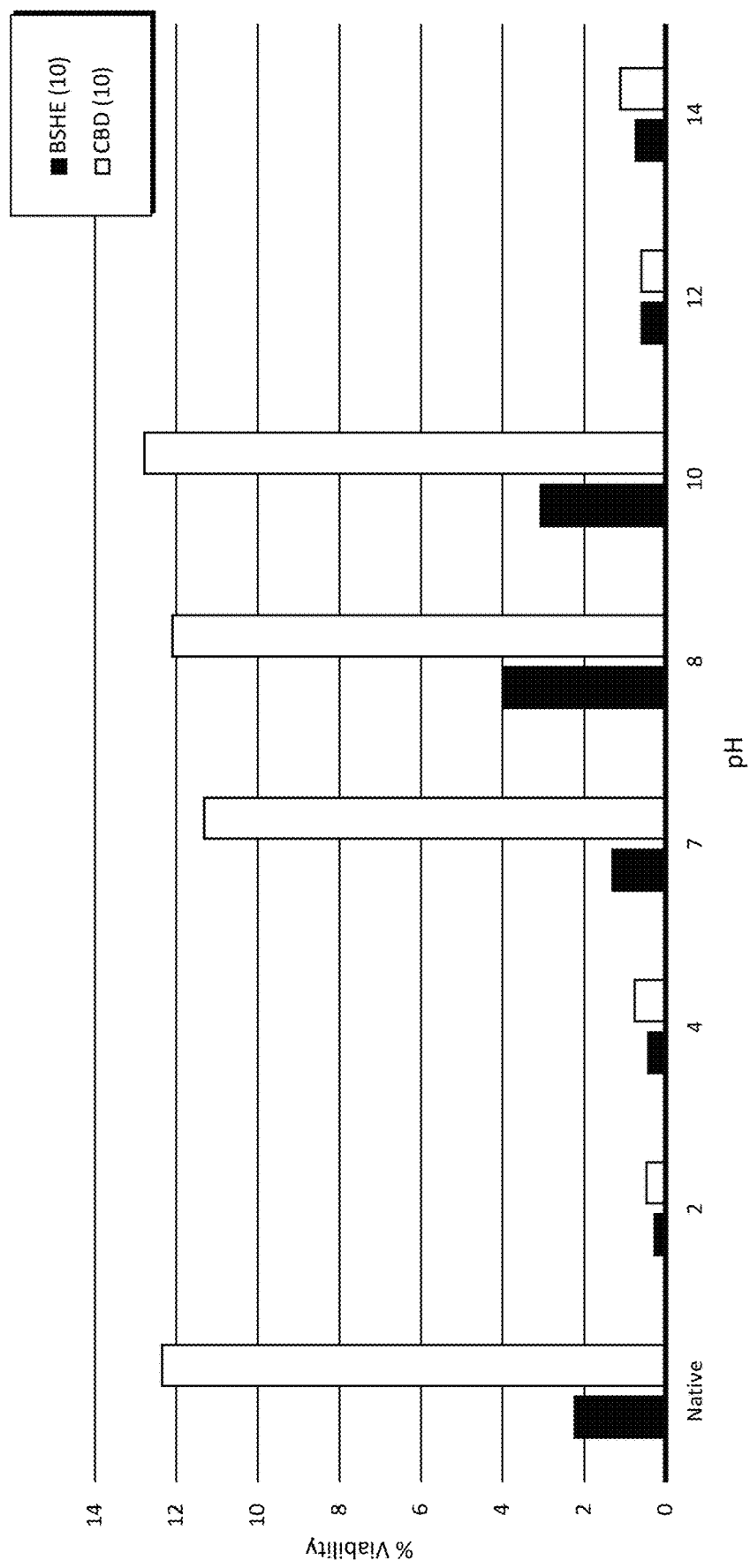
FIG. 11 depicts the effects of pH modification of the cannabis extract when applied at the same concentration to a cancer organoid. Notably, native pH is approximately 10.85 and the ability to reduce viability is worse at pH of 10 and 8, than at native pH, and surprisingly more potent at pH of 4.

A further interesting observation was determined by the impacts of pH on the efficacy of the cannabis extract on organoid data. FIG. 11 shows that the native pH of the cannabis extracts provided for an approximately 2 or 12% viability for the organoids. In each case, the control vehicle, buffered to the same pH was ineffective in killing the cells at all, and thus was not depicted. However, increasing the pH led to substantial improvements in efficacy. However, pH of 12, and certainly of 14 are highly corrosive, alkaline concentrations and are not suitable for therapeutic use. Indeed, such a pH would not be isotonic, nor would it be appropriate for intravaginal application. The vagina has an acidic pH, which is necessary to maintain the balance of bacteria. However, strong modifications of the pH, either alkaline, or highly acidic (below pH of 2, for example) may lead to denaturing of the proteins or other problems. What was immediately evident is that the first attempts to buffer, even slightly, the pH to be more acidic, yielded inferior results. Indeed, each of the two cannabis extract materials reduced its efficacy by decreasing pH from 10.5 to pH of about 10. Furthermore, reducing the pH further to 8, again made the BSHE almost twice as weak at killing the organoids as the native pH, while the CBD isolate shows virtually no change. Even at pH of 7, a neutral pH, the changes are minimal at best.

In such a situation, decreasing the pH further would not likely lead to any further gains for therapeutic efficacy, as the changes were typically worse or showed virtually no change as compared to native pH. Instead, unexpectedly, by further decreasing the pH to 4, a dramatic improvement in the percent viability was seen for each of the BSHE and the CBD isolate, such that each were under a 1% viability, such result was unexpected based on the prior data trending toward a worse response or virtually unchanged response. Accordingly, when providing the cannabis extract for therapeutic administration, decreasing the pH to about 3.5 to 5.5 yields an unexpected increase in efficacy. This is, especially relevant where the cannabis extract is provided intravaginally nasally, or oromucosally, whereby utilizing a buffer to modify pH to between 2 and 6, yields a superior response, than giving the cannabis extract at its native pH. Preferably, the cannabis extract is provided in a carrier with a pH of between 3.5 and 5.5, and more preferably at between a pH of between 4 and 5.

Administration of Cannabis Extracts to Human Patients

Figure 1F:

Whether through oral, oral mucosal, vaginal mucosal, or other routes of administration to treat gynecological cancers, such as ovarian cancer, CBD was shown to be effective in complex cellular structured organoids as well as in mice models. Because of the low bioavailability of CBD as provided through a cannabis extract, initial tests for patients were provided via oromucosal and intravaginal application to reach therapeutic efficacy. Furthermore, because of the targeted approach toward gynecological tissues, those of ordinary skill in the art will recognize that certain therapeutics are able to pass through the vaginal mucosa and contact tissues both on the vaginal wall, but also tissues adjacent to the vaginal wall, including the entirety of the gynecological tract, including the uterus, cervix, ovaries, etc., as non-limiting tissues. Furthermore, there is an abundance of endocannabinoid receptors in the female reproductive tract to allow for possible therapeutic impact of administered cannabinoids to such tissues, as is depicted in FIGS. 1E and 1F. Furthermore, intervaginal delivery of cannabinoids may result in uptake via the inguinal lymph nodes, leading to addition systemic uptake from the reproductive tract.

Intravaginal delivery is well studied and considered safe, effective and well tolerated. Intravaginal delivery avoids gastrointestinal absorption and bypasses first pass metabolism, while facilitating a localized effect and a steady, sustained therapeutic response. Absorption and systemic delivery via vaginal epithelium occurs rapidly with similar lipophilic compounds. Variances in thickness of the vaginal epithelium and vagina fluid characteristics, including pH, presence of cervical mucous, and microbiota, may influence absorption rates and bioavailability.

Mucosal dosing may be easily administered through the oral mucosa. Data on oral-mucosal or sublingual delivery, demonstrates that CBD has a maximum plasma concentration of 1.6 hours, but this can be delayed in some individuals. Orally delivered CBD has a maximum plasma concentration of about 2.5-5 hours but can be delayed up to 6 hours for some individuals. Coadministration with high fat food has been shown to increase Cmax by up to 5-fold concentration. Furthermore, the prevalence of lymph nodes in the back of the mouth then allows for more rapid onset and uptake of the CBD systemically.

In certain situations, administration may be desirable within the sinus cavity, and thus delivery of CBD via highly vascularized nasal mucosa may be desirable. Studies have shown that CBD delivery via the nasal mucosa results in rapid uptake and a Tmax of approximately 10 minutes. Furthermore, as the material passes to the rear of the sinuses, it will pass through the throat and may serve as one of the best ways to reach certain metastases from the cancer, as well as the significant lymph system within the sinus and throat.

Finally, rectal application may also be suitable in certain applications. Rectal suppository delivery results in an increased bioavailability (51-60%) versus oral routes for CBD. Accordingly, mucosal dosing, can allow for targeted administration of cannabis extracts to treat both local and also metastatic tumors. Additional dosing may still be accomplished via traditional dosing routes, including but not limited to oral dosage forms, such as a soft gel comprising a cannabis extract. Furthermore, administration may be injected, intramuscularly, or into other suitable tissues for uptake.

Accordingly, mucosal dosing, particularly intravaginal dosing has a therapeutic efficacy that can allow for targeted treatment of gynecological cancer cells, which will treat both localized tumors as well as metastasized tumors in diseases such as ovarian cancer and endometrial cancer, as well as metastatic disease related to the same. These data were confirmed by further testing within human patients, which showed that treatment with CBD was effective in reducing chemoresistant EC, which had metastasized, in the body.

A 31-year old Caucasian female, presented with significant pain and discomfort, which upon diagnosis was revealed to be endometrial cancer. Patient underwent total hysterectomy bilateral salpingo-oophorectomy followed by five rounds of chemotherapy. Each of the first five rounds of chemotherapy was a combined chemotherapy with Pacli-taxil/Carboplatin. The treatments were ultimately ineffective and she did not proceed with a sixth round due to ineffectiveness of the prior rounds. She then began treatment with Abemaciclib followed by Atezolizumab, which also failed due to chemoresistance and resulted in severe adverse effects. Accordingly, she was deemed her to have chemoresistant endometrial cancer.

The endometrial cancer was stage IV and metastasized into metastatic lymph nodes, pulmonary metastases, peritoneal metastases, which was confirmed by PET scans. Metastatic endometrial cancer was confirmed by the presence of cancer growth in distal organs. An organoid was crafted for the patient to assess her response to CBD and alternative chemotherapies after failing seven chemotherapy rounds due to chemoresistance. The organoid demonstrated a significant response to CBD and a partial response to gemcitabine/capecitabine (GemCap), a combination chemotherapy she had not yet been offered. The patient began using CBD, 30 mg of BSHE via oromucosal delivery twice daily along with 75 mg of FSHE via intravaginal delivery daily, along with standard protocol GemCap. This resulted in a total daily dose of 135 mg of CBD. The patient's progress was monitored and confirmed by PET scans.

The chemoresistance and aggressive nature of the cancer lead to extensive metastatic disease. Previously identified throughout the body, including in the brain, breast, heart, stomach, lungs, and lymphatic system. Measurements of metastatic nodes had previously ranged from 11×7 mm to 29×10 mm. After 12 weeks of treatment, a follow up PET scan reported zero measurable nodes, the results of which are detailed in Tables 1 and 2. Radiology concluded a complete metabolic response to treatment.

Table 1 details metabolic response in the patient's lymph nodes. After treatment, no new enlarged or hyper metabolic nodes within the neck, chest, abdomen, pelvis, or inguinal regions to suggest new sites of metastatic adenopathy.

TABLE 1

| Area | Before Treatment | | After Treatment | |
|---|---|---|---|---|
| | Size | SUV max | Size | SUV |
| Left Supraclavicular: | 25 × 16 mm | 18.1 | 7 × 4 mm | No longer measurable on PET |
| Subcarinal | 21 × 14 mm | 16.1 | 9 × 5 mm | No longer measurable on PET |
| Left Hilar | 18 × 10 mm | 10.5 | 8 × 5 mm | No longer measurable on PET |
| Left External Iliac | 15 × 12 | 17.8 | 8 × 5 mm | No longer measurable on PET |
| Aorticopulmonary | 29 × 10 | 15.1 | | No longer measurable on CT or FDG PET |
| Left internal Mammary | 10 × 8 mm | 9.2 | | No longer measurable on CT or FDG PET |
| Right internal mammary | 11 × 7 mm | 3.9 | 5 × 3 | No longer measurable on PET |
| Left Gastric | 23 × 15 mm | 13.2 | 12 × 7 mm | No longer measurable on PET |
| Left of SMA | 20 × 19 mm | 10.4 | 7 × 4 mm | No longer measurable on PET |

TABLE 2

METABOLIC RESPONSE IN PULMONARY METASTASES WITH TARGET LESIONS

| Area | Before Treatment | | After Treatment | |
|---|---|---|---|---|
| | Size | SUV max | Size | SUV |
| Left Lower lobe Lateral | 18 × 13 mm | 17.9 | 6 × 3 mm | no longer measurable on PET |
| Right Upper lobe Central | 19 × 14 mm | 17.9 | no longer measurable on CT or FDG PET | |
| Peritoneal | 22 × 10 mm | 7.2 | No longer measurable on PET | |

Table 2 details the change in pulmonary metastases. Notably, significant reductions in the size of metastases was documented. Furthermore, no new hypermetabolic pulmonary metastases, no lymphangitis, no pleural or pericardial effusion, no abnormal metabolism in the solid abdominal organs, and no evidence of solid abdominal visceral or metastatic disease on diagnostic CT. Previously demonstrated malignancy ascites in the pelvic region was also documented as near completely resolved. Complete metabolic response in peritoneal deposits. For example, largest deposit inferior to the right lobe of the liver 4 mm. No longer measurable on PET. Previously 22×10 mm, SUV max 7.2). No new hypermetabolic peritoneal deposits. No abnormal metabolism in the brain. No suspicious lesions on the low dose, non-contrast CT. No abnormal metabolism in bone to suggest osseus metastasis.

Furthermore, Table 3 lists agents that were tested on the patient derived organoids, showing that the majority of agents did not impact the patient's cancer.

TABLE 3

| Drug | $C_{max}^2$ | Calculated $IC_{50}$ PD3D Cell Culture |
|---|---|---|
| Cisplatin | 3.62 μM | 5.05 μM |
| Samotolisib | 0.6 μM | 0.87 μM |
| Panobinostat | 0.06 μM | 0.11 μM |
| Niclosamide | 0.31 μM | 0.6 μM |
| Etoposide | 33.8939875 | 87.30551 |
| Temozolomide | 37.6 μM | 105.7 μM |
| Artesunate | 8.58 μM | 38.4 μM |
| Metformin | 10.84 μM | Not Reached |
| Colchicine | 0.006 μM | Not Reached |
| Glutathione | 150 μM | Not Reached |
| Ascorbic Acid | 436.2 μM | Not Reached |
| Hydroxychloroquine | 0.12 μM | Not Reached |
| Pomalidomide | 0.27 μM | Not Reached |
| Sunitnib | 0.09 μM | Not Reached |
| Dichloracetate | 330 μM | Not Reached |
| Bevacizumab | 0.92 μM | Not Reached |
| Kadcyla | 0.53 μM | Not Reached |
| Cetuximab | 1.4 μM | Not Reached |
| Crizotinib | 0.23 μM | Not Reached |
| Propranolol | 0.102 | Not Reached |
| Ruxolitinib | 0.587 | Not Reached |
| Capecitabine (5-FU) | 2.22174388 | Not Reached |
| Cobimetinib | 0.51383399 | Not Reached |
| Ponatinib | 0.13707376 | Not Reached |
| Pemetrexed | 290.623674 | Not Reached |
| Lenvatinib | 0.99987584 | Not Reached |
| Olaparib | 17.4680519 | Not Reached |

The summary from Table 3 shows that many of the agents were unable to reach any IC50, therefore having no impact on the cancerous growths. A few of the materials were slightly effective on organoid samples, but the IC50 number remained below the C, identifying them as poor choices for therapeutic use. However, none were as effective as the cannabis extract treatment for the patient.

A few of the above drug products, as well as additional drugs were tried for response to patient derived organoids. Table 4 lists additional drugs products and their percent of organoid cell death.

TABLE 4

| Drug Name | % Cell Death |
|---|---|
| 5-Fluorouaracil/Capecitabine | 61 |
| Gemcitabine | 56 |
| Bleomycin | 53 |
| Irinotecan | 51 |
| Mitoxantrone | 50 |
| Vinorelbine | 45 |
| Melphalan | 40 |
| Temozolomide | 40 |
| Doxorubicin | 39 |
| Paclitaxel | 39 |
| Vinblastine | 38 |
| Cabazitaxel | 37 |
| Cisplatin | 36 |
| Etoposide | 33 |
| Trabectedine | 32 |
| Dacarbazine | 32 |
| Cyclosphosphamide | 32 |
| Carboplatin | 30 |
| Docetaxel, epirubicin, eribulin, ifosfamide, methotrexate, mitomycin, oxaliplatin, pemetrexed, vincristine | No Response |

Notably, and as expected, paclitaxel was shown to be wholly ineffective, and thus the 39% cell death is indicative of the need to greatly increase the cell death for successful treatment.

CONCLUSION

After the combined treatment with gemCap and cannabis extract with CBD at 130 mg/day, the patient's scan revealed a complete metabolic response to treatment. Previously demonstrated metastatic lymph nodes, pulmonary metastases and peritoneal disease are barely perceptible on CT with complete metabolic response. Malignant ascites has near completely resolved and no new hypermetabolic disease. However, while the patient remained in cancer remission, she had significant damage to her organs from the several rounds of chemotherapy and she died from complications from the organ damage from chemotherapy, with an absence of cancerous growths at the time of death. Accordingly, even though the combined therapy of chemotherapy and cannabis extract proved to be highly effective in reducing tumor growth, the pre-existing damage from the numerous rounds of chemotherapy proved to be fatal. There is no telling of whether she could have achieved earlier remission and thus not been subjected to the several rounds of unsuccessful chemotherapy, had she utilized the cannabis extract with CBD during earlier rounds of chemotherapy. However, we can confirm that her last treatment proved to be effective with a combined therapy of chemotherapy and cannabis extract having CBD.

Therefore, the therapeutic treatment of ovarian cancerous growths was treated, by reduction of the tumor size and selective destruction of the endometrial cancer cells. Can be treated through the application of CBD intravaginally through application of a cannabis extract as an intravaginal application. However, the dose can be repeated several times a day, wherein a total dose may be between 20 and 4250 mg a day. In preferred embodiments, a dose of between and 1250 mg of CBD from a cannabis extract, selected from a FSHE, a BSHE, a CBD isolate, or CBDA is given at least once a day, to meet the therapeutic requirements for the patient. In further preferred doses, the CBD dose is between 25 and 1000 mg, or between 30 and 750 mg, or between 40 and 600 mg, or between 50 and 500 mg a day. Dosing may be performed by administration through a single route or through multiple routes of administration. In a preferred embodiment, the cannabis extract comprises a fat or oil as a carrier for intravaginal application, and further comprises at least one terpene.

In a preferred method, a method of treating a grade 1, 2, or 3 ovarian cancer comprising, administering to a patient in need thereof, an effective amount of a cannabis extract comprising CBD. In preferred embodiments, the cannabis extract comprises total cannabinoids of between 50 and 99.9 of the cannabis extract. When described herein, the percent of the cannabis extract, means that, as in the preceding sentence the total cannabinoids make up between 50 and 99.9% by weight of the cannabis extract. Preferably, of the total cannabinoids, CBD makes up at least 60%, and more preferably, at least 65, 70, 75, 80, 85, 90, 95, and 99% of all cannabinoids within a cannabis extract. In preferred embodiments, the oromucosal dose is administered within a carrier of a fat or an oil. In preferred embodiments, a dose is provided as an oromucosal dose, an intravaginal dose, a nasal mucosal dose, a rectal dose, an oral dose, an intramuscular injection, or an intravenous dose.

The therapeutic methods herein for treatment of ovarian cancers provide for an oral therapy, an oral mucosal therapy, an intravaginal therapy, a nasal mucosal, an injectable, or a rectal therapy, or combinations thereof. Thus, in treating ovarian cancers, an intravaginal therapeutic may be used alone or combined with an oral or oral mucosal therapy, or with a rectal therapy, or an oromucosal dose may be administered alone or in combination with another dosage form.

The oral mucosal therapy seeks to bypasses first pass metabolism through the oral mucosa and allows for higher bioavailability as compared to oral doses that are swallowed. This is due to partial absorption by the buccal tissues followed by metabolism through the amounts swallowed, and entering the systemic systems through the GI tract. While the uptake of CBD in the oral mucosa has a low rate of permeability over a period of 4-12 hours, and accumulates CBD within the oral mucosa, its uptake is significantly greater than oral absorption in the stomach. This provides for an increase in clinically relevant plasma levels for systemic absorption.

However, a further advantage of the oral mucosal administration is accumulation within the oral mucosal tissues of CBD. A benefit of an oral mucosal therapeutic is the release of CBD into the oral mucosal tissues, for sustained release and also of uptake by the lymph system of the mouth and throat. Oral mucosal application will ultimately yield to the salivary glands, and the CBD materials held in the mouth will eventually wash into the GI tract. However, this also allows for tissue accumulation down the esophagus and the rear portions of the mouth and upper throat.

Furthermore, because of the prevalence of endocannabinoid receptors in female reproductive organs and the central nervous system, intravaginal therapy will allow for uptake through the vaginal mucosa and deliver systemic levels of CBD to the body. Similarly, rectal applications are suitable, as rectal administration bypasses the GI tract and has faster rates of action and higher bioavailability. Furthermore, rectal administration results in higher systemic circulation of the drug, here, CBD, than oral GI administration.

Summary of patient samples: The use of organoids to test the therapy is exciting as we can use representative cells to determine response to different therapies, instead of relying on analog models in other species. Accordingly, the results show that upon contact with the BSHE or FSHE comprising CBD, the organoids were destroyed across varying concentrations, but frequently as low as 5, 7, 10, or 20 µg/mL. This was shown in several different patients of varying stages and grades of endometrial cancer as well as ovarian cancer, all with the same success rates. Converting these numbers into mouse models, confirmed the same efficacy, wherein tumor growth was arrested and tumor volume was reduced, across the board. Furthermore, in converting these values to human patients, the doses were again effective in treating the late stage metastatic cancer. Thus, the treatment was not only effective for targeting the cancer cells in the direct gynecological organs, but also systemically throughout the body, as was indicated by the results from the PET scan.

Currently, Applicant has data for no fewer than 21 patients for various gynecological cancers. Of these, ten are receiving treatment for ovarian cancer, both with ascites recurrent chemoresistant cancer, and several with chemonaive solid tumors. At least the following patients were determined for disease type and known mutations, including ovarian cystadenocarcinoma, with one patient have BRCA2, and TP53, with a second patient having BRCA2, NF1, and TP53. Two patients had high grade ovarian serous adenocarcinoma, with one patient having TP53 mutation, and the other with PIK3R1 and TP53 mutation. A further patient had high grade serous ovarian cancer, but no mutations noted. Another patient with Stage Inc, high grade serous ovarian cancer was BRCA Negative. Two addition patients, one with Stage IVc, low grade serous ovarian cancer and one with undefined ovarian cancer did not have mutations noted. Thus, we can see that BRCA2, and TP53 are commonly conserved mutations being susceptible to the ovarian cancer in these patient lines, and whose organoids were then successfully treated with either of the cannabis extract alone or concurrently with one or more chemotherapeutic agent.

In each case, as the data indicates in the figures, a 10 µg/mL therapeutic application was sufficient to show a complete eradication of organoids in numerous samples. This was calculated as approximately 200 mg/day of CBD, which can be provided in any number of different cannabis extracts. Notably, in a few instances, higher dosing was required, and thus administration of 250, 300, 350, 500, 750, 1000, 1500, 2000, 2500, 3000, 3500, 4000, 4500, or more, may be suitable and necessary for therapeutic dosing. In some instances, lower does were also effective. However, in view of the ultimate goal of reducing the growth and proliferation of ovarian cancer cells, it may be prudent to slightly over-reach on the dosing, instead of under dosing. Thus, while even doses as low as 25, 50, or 100 mg a day may be sufficient, especially when combined with chemotherapy agents, a higher dose may be recommended to further reduce the quantity of chemotherapy needed for effective treatment.

This provides a new opportunity for therapeutic treatment of all gynecological cancers, but especially toward chemosensitive and chemoresistant ovarian cancer, as a new form of treatment can be achieved by providing cannabis extract, such as from a BSHE, a FSHE, a CBD isolate or CBDA in an effective amount to treat the cancer. Unexpected success of low concentrations on patients shows that the cannabis extracts comprising CBD was highly effective in destroying cancerous growth.

Application of CBD to patients for gynecological cancers is specifically targeted at intravaginal application of the broad spectrum CBD. Notably, patients after surgery were provided with intravaginal broad spectrum CBD, to both target remaining lesions and growths that were not completely removed by resection, but also to specifically to address metastatic disease by preventing the spread of metastatic cells or re eliminate those which have already spread through the body. The intravaginal application is superior as it specifically targets the gynecological cancers and provides for rapid systemic uptake. This provides for direct application to the gynecological organs as well as for the systemic influence to reach both the localized cancers and metastatic cancers.

In preferred embodiments, a cannabis extract comprising between 50 to 99% CBD. Accordingly, a 10 mg dose of BSHE or FSHE comprises between 5 to 9.9 mg of CBD. The remaining components of the BSHE or FSHE comprise additional cannabinoids, terpenes, polyphenols, essential fatty acids, and phytonutrients. When provided in a pharmaceutical composition, the concentration of CBD is typically between 5 and 50 mg/mL of a pharmaceutical composition. Certain compositions comprise additional excipients and ingredients, including but not limited to a fat, an oil, MCT oil, long chain triglyceride oils, very long chain triglyceride oils. Terpene components including but not limited to β-myrcene, β-caryophyllene, linalool, apinene, citral, D-Limonene, Eucalyptol. Polyphenols may include, but are not limited to catechins, quercetin, cannflavin A/B/C, rutin, and chlorogenic acid. Omega 3, omega 6, and omega 9 fatty acids may be present, as well as additional phytonutrients such as tocopherol, sterols, carotene, aliphatic alcohols, and certain minerals. These components, including the carrier may make up to 90% by weight of the pharmaceutical composition, however, more preferably CBD comprises between 1 and 99.9% of the pharmaceutical composition.

Therefore, a preferred embodiment is related to a method of treatment of gynecological cancers comprising, administering to a patient an effective amount of a pharmaceutically acceptably composition comprising a cannabis extract having between 50 and 99.9% CBD, wherein the composition comprises one of a BSHE, a FSHE, a CBD isolate or CBDA. In preferred embodiments, an effective amount is one effective to generate an equivalent concentration of at least 10 µg/mL of the BSHE or FSHE at the target tissue. In a further preferred embodiment, an effective dose is between 10 and 2500 mg a day of CBD, wherein said CBD is provided in a cannabis extract through an intravaginal application, oral, oral mucosal, or combinations thereof.

In a further preferred embodiment, a method of treatment ovarian cancer comprising, administering to a patient an effective amount of CBD from a cannabis extract.

In a further preferred embodiment, a method of treatment of chemoresistant ovarian cancer, comprising administering to a patient an effective amount of CBD from a BSHE or FSHE. In preferred embodiments, an effective dose is one effective to generate a concentration of at least 10 µg/mL of BSHE or FSHE at the target tissue. In a further preferred embodiment, an effective dose is between 25 and 2500 mg of CBD, wherein said CBD is provided in a cannabis extract, and delivered through an intravaginal application. In certain embodiments, a patient is first tested for chemoresistance to their particular cancer, and upon confirmation of chemoresistance, treating with the effective amount of CBD from a cannabis extract.

In preferred embodiments, the cannabis extract is provided in a pharmaceutically acceptable composition, comprising a suitable carrier and excipients for intravaginal dosing, wherein the active ingredients, specifically the CBD, from the cannabis extract pass through the vaginal membrane to target tissues in the female reproductive system as well as obtaining systemic uptake of the active ingredients for systemic distribution.

In certain other applications, it may be suitable to coadminister the CBD treatment with an ongoing radiation or chemotherapeutic treatment. Therapeutic coadministration may be suitable for increasing efficacy and/or decreasing the dose and thus toxicity related to chemotherapeutic treatment.

In preferred embodiments it is advantageous to modify the osmolality of the composition for therapeutic administration so as to be gentle for intravaginal bacteria by the addition of one or more common salts. In further preferred embodiments, it may be appropriate to modify the PH of the carrier so as to more appropriately match the pH of the vagina, which is typically acidic. A buffer, comprising the appropriate conjugate acid and base pair, can be utilized to select and maintain an appropriate pH. Preferably, oral mucosal administration or intravaginal administration of the compositions are provided at a pH of between 2 and 6.

METHODS

Development of patient derived organoids: The patient derived organoids were created as follows: the patient's tissue sample was collected after surgery and bathed in Hank's Balanced Salt Solution (HBSS) (Hyclone, SH30031.02) with 1% Pencillin/Streptomycin (P/S) (Life Technologies, 15070-063) on ice. Then the sample was washed three times with Dulbecco's phosphate-buffered saline (DPBS) and 1% P/S on a shaker (70 rpm) for 15 minutes each. The tissue was then transferred into a pre-sterilized cell-culture hood to mince it finely with a sterile blade. All minced parts were then digested in an enzyme named Accumax (Innovative Cell Technologies Inc., AM105-500) for 2.5 hours at room temperature. After 2.5-hour incubation, the whole digested tissue mince was transferred in another enzyme, TrypLE express, (Gibco, 12604-021) for another 45 minutes in a 37° C. water bath. During this time the solution was continuously agitated in every 5 minutes interval. After 45 minutes of incubation, the solutions were passed through 70 µm filter on a 50 mL falcon tube. The filter was removed, and the flow-through with the cells was collected in 5% FBS AD+++ medium (comprising 1% ITS, 2% B27, 1% N2, 25% WRN, hegf-50 ng/mL, hfgf-10-100 ng/mL, Nicotinamide-1 mM, N-acetyl cysteine-1.25 mM, Primocin-0.2%, Estrogen-2 nm, A8301-0.5 uM, and Y27632). This cell suspension was centrifuged at 1000 rpm for 5 minutes at room temperature to get the cell pellet for counting. Upon checking under hemocytometer cell number was calculated and processed for organoid culture.

After checking under a microscope if we found RBC contamination in the final cell suspension, then we used Red Blood Cell Lysis Buffer (Roche Diagnostics, 11814389001) to get rid of the excess RBC. Human patient cells from endometrial cancer were grown and maintained in a humidified chamber at 37° C. with 5% CO2.

For the Ascites samples, we centrifuged the ascites fluid at 1000 rpm for 10 minutes at room temperature to get the cell suspension. The cell suspension was then treated with Red Blood Cell Lysis Buffer (Roche Diagnostics, 11814389001) to remove the RBC from the final cell suspension. Once samples were created, they were ready for testing, which included treating the organoids with cannabis extract.

Protocol for all Tests: Patient-Derived Organoid (Pdo) Culture and Drug Treatment To culture patient-derived organoids, 2-3×10^3 cells were plated in a pre-warmed (37° C.) 96-well plate in 10 mL of Matrigel (5% FBS AD+++ medium) per well. Individual patient cell organoid was cultured separately in different plates. Individual patient cells were handled separately to reduce the chance of cross-contamination. After mixing cells with Matrigel, 10 mL droplets were placed in wells and put in a 37° C. incubator with 5% CO2 for 30 minutes. Upon solidification of the Matrigel droplet with cells inside, the plate was placed inside a sterile hood and immersed the Matrigel droplet in 200 μL of organoid growth media. Cells were allowed to grow into mature organoids for 14 days. Treatment with individual CBD agents (Broad Spectrum, Full Spectrum, CBD Isolates, and CBDA) or in combination with chemotherapeutic agents (Paclitaxel, Doxorubicin or Carboplatin) was started from day 1, where the individual drug or drug combinations were added in the growth medium. All treatments were done in triplicate, including vehicle-only controls (Dimethyl sulfoxide in culture medium at the highest concentration used for drug treatments).

Individual patient organoids were treated with all the respective cannabis extracts (Broad Spectrum, Full Spectrum, CBD Isolates, and CBDA) to determine the IC50 by inhibitor vs normalized response-variable slope using least squares regression in Graphpad Prism 9. This IC50 was specific for individual patient and individual CBD agent. Now, the same patient's organoid was further treated with incremental doses of chemotherapeutic agents (Paclitaxel, Doxorubicin or Carboplatin) along with the specific IC50 of individual CBD agents for that specific patient. Notably, these doses all fall under the maximal doses suitable for human administration. This helped us to determine if the presence of specific dose (IC50) of individual CBD agents can reduce the dose of chemotherapeutic agents (Paclitaxel, Doxorubicin or Carboplatin) to get the same amount of cancer cell death as of the standard human dose. Note: IC50 is the 50% inhibitory concentration which is conventionally used to determine drug potency with cell-based cytotoxicity tests.

Cell Viability Assay

To assess the cell viability in organoids after treatments, CellTiter-Glo® Luminescent Assay (Promega #G7572) was used. In brief, on day 14 of organoid culture, the matrigel droplet in each well with organoid inside was immersed in 100 μL of fresh growth media and 100 μL of CellTiter-Glo® reagent following the manufacturer's guideline. Blank wells containing only media and CellTiter Glo® reagent (no cells) were also included in each plate. Then the plates were put on a shaker @110 rpm at room temperature for 5 minutes to induce cell lysis, followed by 25 minutes at room temperature to stabilize the luminescent signal. Each step after adding the CellTiter Glo® reagent was performed in the dark. Luminescence was measured on a FLUOstar OPTIMA plate reader (BMG Lab technologies, Offenburg, Germany). Analysis was performed by normalizing treatment values to the vehicle control and plotting them as a percentage of the vehicle control. Drug IC50 values were determined by inhibitor vs normalized response-variable slope using least squares regression in Graphpad Prism 9.

Mouse Model: Patient-Derived Xenograft (Pdx) Mouse Generation

Human patient cells from endometrial cancer were injected subcutaneously into female NOD/SCID gamma mice after resuspending in 100 μL solution. Once the tumor grows to a visible size all mice were intraperitoneally injected with CBD single agents (all 10-30 mg/kg body wt) and/or CBD+chemotherapeutics (CBD (10-30 mg/kg body wt), Paclitaxel (up to 20 mg/kg body wt)/Carboplatin (up to 60 mg/kg body wt), Doxorubicin (up to 15 mg/kg body wt)) or Vehicle thrice per week for up to 5 weeks. Tumor size measured before treatment, followed by twice a week measurement. All treatment group mice were kept alive for up to 10 weeks after drug injection or until the tumor volume grows bigger than 2500 mm 3.

Tumor size was measured along with body weight at the time of tissue collection. All tumor tissues were removed carefully from the euthanized mouse body. Tumor tissue samples were kept for histology, proteomics, genomics, and other downstream processing. All downstream processing was completed following NCI Patient-Derived Models Repository SOPs. Tumor volume graph will be plotted using GraphPad Prism 9.

Translating the organoid doses to an equivalent human dose was determined by a standard formula. (M=m/MW× 1/V where m=mass in grams, MW=molecular weight of the substance and V=volume of the diluent in liters). Thus, for example, if Drug X has an organoid dosage of 54.35 uM it would be calculated as follows: That means we need 0.0032 mg of DRUG X in 100 μL or 0.0001 L (V) that will be equivalent to 0.00005435 M or 54.35 μM concentration, where MW of DRUG X=588.72 g/mol and m=0.0000032 g.

When performing additional tests, samples tested in 96 well plates can use a different formula for translating to human dosage. When testing with the 96 well plates, the surface area of a single well in 96 well plates is 0.32 cm$^2$. That means the clinical dose equivalent (mg/m$^2$) will be 100 mg/m$^2$ by following the formula below, Clinical Dosage (mg/m$^2$)=(PDO dosage in mg/culture plate surface area cm$^2$)×100$^2$. When comparing the two different methods of translating the organoid dose to the human dose, the two calculations show a very similar human equivalent dose, for example of approximately 200 mg/day for the organoid equivalent of 10 μg/mL.

Mouse Pdx to Human Dose Conversion

The Food and Drug Administration (FDA) has suggested that the extrapolation of animal dose to human dose is correctly performed only through normalization to body surface area (BSA), which often is represented in mg/m$^2$. The human equivalent doses (HEDs) can be more appropriately calculated by using the formula: Human Equivalent Dosage in mg/kg=Mice Dosage (mg/kg)×(Mice Km/Human Km). The correction factor (Km) is estimated by dividing the average body weight (kg) of species to its body surface area (m$^2$). For example, the average human body weight is 60 kg, and the body surface area is 1.62 m$^2$. Therefore, the Km factor for human is calculated by dividing 60 by 1.62, which is 37 and same way the mouse Km factor was calculated, which is 3. Now to interchange of unit (mg/kg to mg/m²) of dose of animals or human is carried out using the Km factor as per BSA: Dosage for mg/m²=Km×dosage in mg/kg.

The mouse studies utilized intraperitoneal dosing of various formulations of cannabis extracts comprising a known quantity of CBD. For each of the various cannabis extracts, BSHE, FSHE, CBD isolate, and CBDA, 2 to 3 mice were tested against each of a vehicle alone (control), with the results being compared to the volume at T=0 for each of the mice. Dosing was 30 mg/kg of each of the cannabis extracts, the results of the CBD only study is defined in FIG. 5.

Notably, the concentration of CBD used in each case remains on the low end of the therapeutic dose suitable for administering to a human patient, or to a mouse. The low doses were utilized in order to show impact of the cannabis extracts, instead of each of the data going to zero, by using double, triple, or higher of the dose as administered to the mice, all of which would be appropriate human equivalent doses. Even with the lower dosing, at time of 21 days, virtually all of the samples are progressing tumor volume toward zero, and in one case, the tumor volume has reached zero at day 21. Therefore, when comparing these quantities to those from the organoid data, we see that each sample retains the efficacy from the organoid data. Thus, administering higher doses of CBD, will yield a greater reduction in tumor volume in the mouse model. Thus, administering cannabis extracts is effective in greatly slowing the growth of endometrial cancer tumors, and ultimately reduces the tumor size, which may result in the eradication of tumor cells, by administering the cannabis extracts to the mice.

Creation of Cbd Samples

Cannabis extracts for therapeutic use in the methods herein, are generated by an extraction process to remove desired materials from the trichomes and other green material from plants within the cannabis genus. In the extraction process, a wide variety of cannabinoids have been isolated from the cannabis plant, and some have reported 483 identifiable chemical constituents known to exist in the cannabis plant, many of which are generated in levels that are below the level of quantitation. However, the cannabis extracts utilized herein, utilize cannabis strains that having high concentrations of CBD, and the products being generated typically are evaluated based on a CBD content in mg. The cannabis extracts further, preferably, comprise certain amounts of array of cannabinoids and other phytonutrients such as essential fatty acids, flavonoids, terpenes and essential vitamins and minerals A representative, nonlimiting sample of the cannabis extract of the present disclosure comprises concentrations of certain compounds within the following ranges:

TABLE 5

| BSHE | | |
|---|---|---|
| Cannabinoid | mg/g | % |
| $\Delta^8$-THC | ND | 0-1 |
| $\Delta^9$-THC | ND | 0-0.3 |
| $\Delta^9$-THCA | ND | 0-0.3 |
| THCV | ND | ND |
| THCVA | ND | ND |
| CBD | 900 | 70-99 |
| CBDA | ND | 0-2.5 |
| CBC | ND | 0-3.5 |
| CBCA | ND | 0-5.0 |
| CBDV | ND | 0-2.5 |
| CBG | 15 | 0.1-3.5 |

TABLE 5-continued

| BSHE | | |
|---|---|---|
| Cannabinoid | mg/g | % |
| CBGA | ND | 0-3.5 |
| CBN | 2.0 | 0.01-0.5 |
| Total THC | ND | 0-1.5 |
| Total CBD | 898.49 | 70-99 |
| Total Cannabinoids | 915.63 | 71-99 |
| Sum of additional Cannabinoids | 0 | 0-10 |

TABLE 6

| FSHE | | |
|---|---|---|
| Cannabinoid | mg/g | % |
| $\Delta^8$-THC | ND | 0-3.0 |
| $\Delta^9$-THC | 25 | 0.01-5.0 |
| $\Delta^9$-THCA | ND | 0-1.0 |
| CBD | 800 | 65-98 |
| CBC | 19 | 0-3.5 |
| CBDV | 8 | 0-2.5 |
| CBG | 17 | 0.1-3.5 |
| CBN | 1.65 | 0-0.5 |
| Total THC | 25.47 | 0.3-5.0 |
| Total CBD | 799.43 | 65-98 |
| Total Cannabinoids | 869.94 | 65-99.9 |
| Sum of additional Cannabinoids | 0 | 0-10.0 |

Terpenes and Other Key Molecules

Preferably, the formulation has the following fingerprint: A simplified approach to the formulations is that the B SHE includes between 60-95% of a CBD, THC of 0-5%, and additional cannabinoids between 0.1 and 20%. Additional elements include between 0.1 and 20% of waxes and fatty acids.

In further preferred embodiments, the additional cannabinoids comprising the 0.1 and 20% are selected from the group comprising: $\Delta^8$-THC, $\Delta^9$-THCA, CBDA, CBC, CBDV, CBG, CBGA, CBN, and combinations thereof. The meaning, therefore, includes one or more of these cannabinoids, but does not exclude additional cannabinoids. In a further preferred embodiment, wherein at least one additional cannabinoid is present in the formulation at between 0.1 and 10%, selected from the group consisting of: $\Delta^8$-THC, $\Delta^9$-THCA, CBDA, CBC, CBDV, CBG, CBGA, CBN, and combinations thereof.

A sample of cannabis extract, using a broad spectrum hemp extract was utilized on endometrial cancer patient derived organoids, to determine efficacy of cannabis extracts on endometrial cancer cells.

Summary of Patient Testing

ENDOMETRIAL CANCER PATIENTS: A total of 11 patients (8 patients with grade 1 and 3 patients with grade 2). These patients are aged between 40 to 75 years of age. The tissue samples were collected at time of surgery (total hysterectomy or total hysterectomy bilateral salpingo-oophorectomy) and disease was confirmed by the pathologist. Patients are consecutively and prospectively included when diagnosed with a pelvic mass of suspected uterine origin and are admitted for surgery for a clinically suspicious malignant endometrial growth. To be eligible for enrolment patients are required to be 18 years of age or older and have a diagnosis of endometrial cancer with a planned surgical intervention. Menopause status, defined as one year of amenorrhea, is checked for women between 47 and 56 years of age. Patients<47 years are considered premenopausal and women>56 years, postmenopausal. The exclusion criteria are: pregnancy, significant concomitant diseases such as chronic heart failure, severe chronic liver or renal disease, a prior bilateral oophorectomy, pelvic endometriosis or adenomyosis or ovarian primary tumors, and serious medical or psychiatric conditions that may prevent compliance with the protocol. Prior to the collection of biological samples and surgery, all patients are required to give full informed written consent. After surgery, the tumors are examined by an experienced gynecology pathologist for diagnosis, histology, grade, and stage (I-IV), according to FIGO standards. Staging is also conducted by obtaining pelvic washings and performing bilateral pelvic and para-aortic lymph node dissection. Lymph node counts are not required. Only patients with complete surgical staging and pathologically confirmed endometrial cancers will be included in the study.

OVARIAN CANCER PATIENTS: A total of 10 patients (4 patients who are ascites recurrent chemoresistant, 1 patient who is solid chemo naive, 5 patients who are solid chemoresistant, all ten patient's metastatic disease). Patients are consecutively and prospectively included when diagnosed with a pelvic mass of suspected ovarian origin and are admitted for surgery for a clinically suspicious malignant pelvic mass of ovarian/tubal origin. To be eligible for enrolment patients are required to be 18 years of age or older and have a diagnosis of an ovarian cyst or a pelvic mass with a planned surgical intervention. Menopause status, defined as one year of amenorrhea, is checked for women between 47 and 56 years of age. Patients<47 years are considered premenopausal and women>56 years, postmenopausal. The exclusion criteria are: pregnancy, significant concomitant diseases such as chronic heart failure, severe chronic liver or renal disease, a prior bilateral oophorectomy, and serious medical or psychiatric conditions that may prevent compliance with the protocol. Prior to collection of biological samples and surgery, all patients are required to give full informed written consent. After surgery, the tumors are examined by an experienced gynecology pathologist for diagnosis, histology, grade, and stage (I-IV), according to FIGO standards.

ENDOMETRIOSIS PATIENTS: A total of 9 patients (2 patients with ovarian endometrioma and 7 patients with deep endometriosis), Patients were those referred by their general practitioners or other clinicians for investigation of pelvic pain or for diagnosis and/or treatment of endometriosis. Those who agreed to undergo laparoscopic surgery for investigation and treatment of endometriosis, pelvic pain or bilateral salpingoophorectomy for strong family history of breast and ovarian cancer were approached and recruited. Inclusion criteria were as follows: 'endometriosis cases' were defined as women diagnosed with endometriosis at laparoscopy and confirmed histologically; 'controls with pain' were defined as symptomatic women with pelvic pain of unknown cause or chronic pelvic inflammatory disease without surgical evidence of endometriosis; 'controls without pain' were regularly cycling women with no known disease undergoing bilateral tubal ligation and/or prophylactic bilateral salpingoophorectomy due to familial risk of breast and ovarian cancer and with no visual evidence of endometriosis at laparoscopy. The following women were excluded from the study; postmenopausal women, women with a positive pregnancy test or unknown pregnancy status on day of surgery, those with other benign conditions or malignancies (particularly patients with fibroids and/or cancer were excluded as these conditions may compromise the integrity of the endometrium), women on any hormonal medication<3 months prior to surgery and those whose surgical findings and pathological reports were inconsistent. Cycle phase was determined by a triple approach to ensure accuracy; chronologically, by histological dating and by sex steroid hormone determination. Women with unconfirmed menstrual cycle stage were excluded. Additional patient data was collected including age, fertility history, treatment history (oral contraceptive and GnRH analogue use), menstrual cycle phase, pain history, histopathology findings and anatomic characteristics of disease lesions.

In preferred embodiments, the BSHE or FSHE comprise between 50 to 99.9% CBD. Accordingly, a 10 mg dose of BSHE or FSHE comprises between 5 to 9.9 mg of CBD. The remaining components of the BSHE or FSHE comprise additional cannabinoids, terpenes, polyphenols, essential fatty acids, and phytonutrients. When provided in a pharmaceutical composition, the concentration of CBD is typically between 5 and 50 mg/mL of a pharmaceutical composition. Certain compositions comprise additional excipients and ingredients, including but not limited to a fat, an oil, MCT oil, long chain triglyceride oils, very long chain triglyceride oils. Terpene components including but not limited to β-myrcene, β-caryophyllene, linalool, a pinene, citral, D-Limonene, Eucalyptol. Polyphenols may include, but are not limited to catechins, quercetin, cannflavin A/B/C, rutin, and chlorogenic acid. Omega 3, omega 6, and omega 9 fatty acids may be present, as well as additional phytonutrients such as tocopherol, sterols, carotene, aliphatic alcohols, and certain minerals. These components, including the carrier may make up to 90% by weight of the pharmaceutical composition, however, more preferably CBD comprises between 1 and 90% of the pharmaceutical composition.

Therefore, a preferred embodiment is related to a method of treatment of ovarian cancer comprising, administering to a patient an effective amount of a pharmaceutically acceptable composition comprising CBD, wherein the composition comprises a BSHE or FSHE. In preferred embodiments, an effective amount is one effective to generate a concentration of at least 10 µg/mL of the BSHE or FSHE at the target tissue, and more preferably at least a target concentration of at least 20 µg/mL. In a further preferred embodiment, an effective dose is between 10 and 4250 mg a day of CBD, wherein said CBD is provided in a BSHE or FSHE through mucosal dosing. The methods for treatment herein are effective in eliminating inappropriate lesions, i.e., cells that have migrated from their intended location in the body.

In preferred embodiments it is advantageous to modify the osmolality of the composition for therapeutic administration so as to be gentle for intravaginal dosing. In further preferred embodiments, it may be appropriate to modify the PH of the carrier so as to more appropriately match the pH of the vagina, which is typically acidic. Therefore, a preferred embodiment is a composition that has an acidic pH, preferably between 3.5 and 6, within a carrier suitable for intravaginal application.

For oral administration, it may be suitable to add or coadminister with a high-fat component to increase bioavailability, or to modify the pH or osmolality to increase the rate of absorption or the uptake of the CBD into the oral mucosa.

Therefore, the therapeutic treatment of ovarian cancer was treated, by reduction of the tumor size and selective destruction of the ovarian cancer cells. Can be treated through administering a CE comprising CBD. Based on the needs of the patient, the administration is preferably through a mucosal dosing route, such as intravaginally, oromucosally, rectally, or within the nasal passage, or two or more of these dosing routes. A dose can be provided once every three days, every second day, every day, daily, or several times a day, such as two, three, four or more times a day. The therapeutic dose is preferably between 20 and 4250 mg a day. In preferred embodiments, a dose of between 25 and 1250 mg of CBD from a FSHE or BSHE is given at least once a day. In a preferred embodiment, the FSHE or BSHE is part of a composition comprising a carrier to aid in administering the CE. Preferably the carrier is a fat or oil as a carrier for mucosal delivery. In a preferred embodiment, the FSHE or BSHE comprises a fat or oil as a carrier for mucosal application. In another preferred embodiment, the FSHE or BSHE comprises at least one terpene. In a more preferred embodiment, the FSHE or BSHE comprises a fat or oil as a carrier for intravaginal application, and further comprises at least one terpene. Additional excipients or delivery matrix may be further added based on the route of administration. The CE preferably comprises CBD from 50-99.9% of the weight of the CE. However, the CE preferably further includes at least one additional cannabinoid such as CBC, CBG, CBN, CBDA, CBDV, $\Delta^9$-THC, wherein the total concentration of the one additional cannabinoid is between 0.1 and 49%. In further embodiments, the CE may also comprise at least one of a terpene, a polyphenol, a fatty acid, or a phytonutrient. Each of these are preferably derived from the cannabis plant and present due to the extraction process.

In a preferred embodiment, treatment of ovarian cancer comprises treatment with both a chemotherapeutic agent and also a CE comprising CBD. The CE is administered as provided above. The chemotherapeutic agent is administered in its normal route of administration. However, the chemotherapeutic agent is preferably administered at a reduced dose as compared to its normal dose. The reduced dose is possible based upon the determined synergy between the chemotherapeutic agent and the CE. Administration of the CE may be by any suitable route, however, it is preferred for oromucosal treatment to allow for high bioavailability of the CBD adjacent to the lymph nodes in the mouth and throat, and adjacent to the cancerous tissues, as well as reducing the first pass metabolism through mucosal dosing. The CE is preferably a FSHE or a BSHE, wherein the concentration of CBD is preferably at least 50%, and more preferably, at least 60, 65, 70, 75, 80, 85, 90, or 95%, with the remaining portion of the FSHE or the BSHE comprising at least one additional cannabinoid at a concentration of between 0.1 to 40% by weight of the CE. Most preferably, the FSHE or the BSHE comprise at least two cannabinoids, each having a concentration of at least 0.1% by weight of the CE. Most preferably the additional cannabinoid is one or more of: CBC, CBG, CBN, CBDA, CBDV, or $\Delta^9$-THC. In a parallel cancer, administration of the chemotherapeutic agent with the CE was effective in reducing the prevalence of endometrial cancer, which had spread throughout the body in the treated patient. Administration via intravaginal and oral mucosal administration showed a complete reduction in the size of the cancer cells via the PET scan, and thus will also be effective for treating ovarian cancer.

In certain embodiments, the treatment is indicated for chemosensitve ovarian cancer. In such an instance, CE with CBD alone may be sufficient, or administered jointly with a chemotherapeutic agent. In certain other embodiments, the treatment is indicated for metastatic chemosensitive ovarian cancer, wherein the ovarian cancer cells have metastasized and spread beyond the ovaries. In certain embodiments the ovarian cancer is a chemoresistant cancer.

In certain embodiments, the CE can be administered without the need for an additional carrier. Thus, the composition may be the CE without any further carrier or excipient.

However, preferred embodiments include a composition for treatment of ovarian cancer, wherein the composition comprises a cannabis extract (CE), wherein the CE comprises between 1 and 100% by weight of the composition and all percentages therein. In preferred embodiments, the CE comprises between 10 and 90% by weight, or 20 by 90% by weight, and preferably between 40 and 80% by weight of the composition. The CE, as detailed herein, is preferably a BSHE, a FSHE, a CBD isolate, or a CBDA isolate. In each of these different CE, the BSHE, the FSHE, the CBD isolate, or the CBDA isolate, they make up between 50 and 99.9% by weight of the CE, with the remaining being waxes, fats, fatty acids and the like. However, preferred embodiments utilize a carrier at between 1 and 99% by weight of the composition, and preferably, one or more additional excipients depending on the use case of the composition. The composition is typically then administered based upon the dosage in mg of CBD being administered. Wherein the amount of the composition required to meet that mg of CBD depends on the quantity of CBD within each of the CE.

In certain embodiments, personalized medicine may play a critical role in providing optimized therapeutic treatments. Thus, a patient having ovarian cancer may obtain a tissue sample for creation of organoids. The tissue sample is typically taken from a biopsy or resected cancerous tissues. The organoids can then be grown and tested against a panel of chemotherapeutic agents to identify an optimized treatment plan. The preferred plan is to utilize as low a dose of chemotherapeutic agent as possible, in combination with a CE, in order to eradicate the organoids. Thereafter, treatment of the patient with the optimized chemotherapeutic agent and the CE will provide an optimized therapeutic treatment plan. As noted herein, chemotherapeutic agents are highly toxic and the ability to reduce the quantity and number of chemotherapy rounds provides a significant improvement to the cancer treatment, as the significant side effects from chemotherapy can be reduced.

In preferred methods, the cannabis extract is a BSHE. In preferred methods, the BSHE comprises from between 50 and 99% of CBD, and at least one additional cannabinoid. In certain embodiments, the BSHE comprises at least two additional cannabinoids. In further embodiments, the CE comprises at least three additional cannabinoids. In preferred embodiments, the additional cannabinoids are selected from the group consisting of CBC, CBG, CBDA, CBDV, THCV, or $\Delta^9$-THC.

In certain embodiments the cannabis extract is a FSHE, comprising at least 0.1 to 10% $\Delta^9$-THC. In preferred embodiments, a FSHE comprises between 50 and 99% CBD, and between 0.1 to 10% of THC. Preferably, the FSHE comprises a total of 51 to 99.9% cannabinoids, with a total of THC, including $\Delta^8$-THC, $\Delta^9$-THC, $\Delta^9$-THCV, THCV, and THCVA comprising 0.1 to 10% by weight of the CE.

In further preferred methods, the CE is an isolate of CBD derived from a cannabis extract. Thus, the CBD isolate seeks to concentrate the CBD, with the CBD being present at between 70 and 99.9% by weight of the CE. In certain preferred embodiments, the isolate of CBD further comprises at least one additional cannabinoid. In preferred embodiments, the isolated CBD further comprises CBN, CBDA or both at a concentration of between 0.1 and 10%.

Cannabis extracts have only recently begun detailed study into therapeutic effects for treatment of disease. Two molecules typically found in cannabis extracts of highest interest are typically cannabidiol (CBD) and $\Delta^9$ tetrahydrocannabidiol (THC). However, the extracts contain numerous other cannabaniods and to date, scientists have identified at least 144 cannabinoids produced by plants of the genus cannabis, including the hemp plant. Hemp is defined in the US as a cannabis plant with a $\Delta^9$-THC content of 0.3% or less by dried weight, so it is a political definition and not a scientific definition. Accordingly, for purposes of this application, "hemp" is defined as a cannabis plant having a $\Delta^9$-THC content of 0.3% or less by dried weight. The byproducts of hemp plants, including cannabinoids, are federally legal as defined in section 7606 of the 2014 Farm Bill and made permanent in the 2018 Farm Bill. Just a few examples of different cannabinoids include Cannabigerol (CBG), Cannabichromene (CBC), cannabidivarin (CBDV), and Cannabinol (CBN).

Cannabis extracts can be derived from one or more cannabis plant strains as a source material. Notably, while different strains may produce green material with different proportions of desirable compounds, different growing conditions can impact the precise amounts of each compound even for the same strains. Cannabis extracts may include isolates of certain compounds, such as isolated CBD, or may include products that contain a wider variety of cannabinoids and other materials, such as those called a Full spectrum hemp extract (FSHE) and Broad spectrum hemp extract (B SHE), each of which may contain an array of cannabinoids and other phytonutrients such as essential fatty acids, flavonoids, terpenes and essential vitamins and minerals. This combination of cannabinoids offer what is known as the 'entourage effect'—a term created by Ralph Mechoulam to describe the inexplicable synergy that manifests when naturally occurring compounds are consumed in tandem. This effect is thought to be the result of multi-pathway activation and signaling from various nutrients in the cannabis extracts.

A cannabinoid is any one of a diverse class of chemical compounds that influence cannabinoid receptors (CB1 or CB2). These receptors, plus the cannabinoids that activate them, comprise the endocannabinoid system (ECS). There are three primary types of cannabinoids-endocannabinoids, phytocannabinoids, and synthetic cannabinoids. Endocannabinoids also known as endogenous cannabinoids are cannabinoids naturally produced within the body. Phytocannabinoids are cannabinoids produced within plants. Plants that produce cannabinoids include, but are not limited to: kava, rosemary, liverwort, electric daisy, echinacea, cacao, helichrysum, pepper trees, black truffles, cannabis, as well as a strain of yeast (*Pichia pastoris*). Additionally, certain cannabinoids can be synthesized. Synthetic cannabinoids, however to date, have shown a greater risk of adverse effects and a lower therapeutic potential, a conclusion shared by multiple systematic reviews comparing safety and tolerability of phytocannabinoids versus synthetic cannabinoids.

While the purpose of cannabinoids in plants remains unclear, the most popular hypothesis suggests they act to protect the plant from insects, bacteria, fungi, ultraviolet radiation, and drying. By contrast, the human body possess an advanced physiological system, known as the endocannabinoid system (ECS). This central regulatory system makes cannabinoids inside the body (endocannabinoids) that foster cellular balance throughout nearly every biological system in the body. The ECS is widely distributed throughout the entirety of human physiology and is comprised of three main parts. These are: (i) cannabinoid receptors (CB1 and CB2); (ii) endogenous cannabinoids (endocannabinoids) and most notably anandamide and 2-AG; and (iii) Enzymes that break down endocannabinoids (FAAH and MAGL). Cannabinoid receptors, found on the surface of cells, are widespread throughout the body and listen to the environment around each cell. They transmit information on current conditions to the cell and thereby jump-start the proper cellular response. Properly functioning cannabinoid receptors have the crucial function of creating homeostasis in the body's cells.

CB1 and CB2 receptors are the predominant receptors in the ECS. CB1 receptors are abundant in the brain and central nervous system, whereas CB2 receptors are sparse in the central nervous system but are common throughout the periphery, primarily on immune cells. Cannabinoid receptors are present in almost every organ and organ system throughout the body. They influence activities in the reproductive system, heart, lungs, brain, blood vessels, GI tract, liver, stomach, and more. Cannabinoids, found in hemp (phytocannabinoids), such as CBD, may influence a wide array of bodily functions. These phytocannabinoids interact with the cannabinoid receptors and modulate their activity—while at the same time boosting levels of endocannabinoids. For example, CBD works with the cannabinoid receptors by inhibiting FAAH (Fatty Acid Amide Hydrolase), an enzyme that breaks down the naturally produced endocannabinoid anandamide, thus prolonging its half-life. Anandamide is partially responsible for regulating human reproduction, among its other implications within the body.

Endocannabinoid receptors are abundant in female reproductive organs and the central nervous system. Their signaling and trafficking influence multiple physiological and pathophysiological functions of female reproduction, including folliculogenesis, oocyte maturation, cytoskeleton rearrangement, endometrial cell motility, endometrial migration & proliferation, decidualization, plasticity, and peripheral innervation. Thus, cannabinoids exert antiproliferative effects on deep infiltrating endometriosis, and increased cannabinoid signaling may reduce proliferation of endometriotic lesions, the etiology of which shares some genetic basis and pathophysiological overlap with ovarian and endometrial cancers. Cannabinoid receptors in the pelvis, ovaries, endometrium, vulva and the central and peripheral nervous systems influence inflammation, nociception, and arousal at these therapeutic targets. Cannabinoids trigger localized vasodilation and relaxation of pathological smooth muscle contraction and/or spasticity.

Cannabinoid receptors belong to a superfamily of G protein-coupled receptors. They are single polypeptides with seven transmembrane α-helices, and have an extracellular, glycosylated N-terminus and intracellular C-terminus. Both CB1 and CB2 cannabinoid receptors are linked to G1/0 proteins. In addition to these receptors, endogenous ligands for these receptors capable of mimicking the pharmacological actions of THC have also been discovered. Such ligands were designated endocannabinoids and included anandamide and 2-arachidonoyl glycerol (2-AG). Anandamide is produced in the brain and peripheral immune tissues such as the spleen.

Unlike THC, which exerts its action by binding to CB1 and CB2, CBD does not readily bind to these receptors and hence has no psychotropic activity. Instead, cannabidiol indirectly stimulates endogenous cannabinoid signaling by suppressing the enzyme that breaks down anandamide (fatty acid amide hydroxylase, "FAAH"). CBD also stimulates the release of 2-AG. Therefore, the mechanisms of action for CBD are complex, varied, and still only partially understood. CBD is an antagonist and a partial allosteric modulator of CB1 receptors. There is evidence that CBD stimulates 5HT1A/2A/3A serotonin receptors, TRPV1-2 vanilloid receptors, and glycine channels. CBD does not bind to either CB1 or CB2 receptors and thus most, if not all, of CBDs mechanisms are not directly CB receptor mediated.

Accordingly, CBD may be implicated in signaling pathways in the body. For example, CBD may play a modulatory role with regard to cytokines. Cytokines are signaling proteins synthesized and secreted by immune cells upon stimulation. Accordingly, one of the possible mechanisms of immune control by CBD is by perturbing the balance between cytokines produced by T helper subsets, $T_h1$ and $T_h2$. In certain prior studies, both anti-inflammatory and proinflammatory effects were shown.

During chronic inflammation, IL-6 suppression can decrease tissue injury. Cannabinoids, including CBD and THC have been shown to decrease IL-6, TNFα, GM-CSF, and IFNγ. Accordingly, one or more of CBD or THC may be a necessary component in certain applications when a combined effect is necessary to reduce inflammation and decrease pain. Low doses of THC may be suitable to provide these therapeutic effects in combination with CBD.

CBD is also known to stimulate vanilloid pain receptors (TRPV-1 receptor), which are known to mediate pain perception, inflammation, and body temperature. CBD may also impact certain adenosine receptors, which play a significant role in cardiovascular function and broadly impact anti-inflammatory effects throughout the body as well as regulate and decrease anxiety and depression and increase the sense of well-being.

Uptake of phytocannabinoids within the body is confounded by its physical property. Phytocannabinoids are nearly insoluble in water but are soluble in lipids, alcohol, and nonpolar organic solvents, and can also be suspended in emulsions. THC and CBD are both highly lipophilic and have poor oral bioavailability when swallowed, at between 6 to 10 percent, amounts which may be increased through specific preparations. Oral THC formulations exhibit variable absorption and undergo extensive hepatic first-pass metabolism, resulting in lower peak plasma THC concentration relative to inhalation and a longer onset (~120 min) to reach peak concentration, Following oral administration of CBD, a similar plasma concentration—time profile to that of oral THC has been observed. Based on this profile, oral formulations may be useful for patients requiring symptomatic relief over a longer period, though higher concentrations may be necessary, in order to reach therapeutic plasma concentrations, as compared to alternative delivery methods, such as inhalation. Furthermore, certain liver toxicities may exist because of the extensive first, pass metabolism when higher dosage amounts are needed for therapeutic levels.

Transdermal administration of cannabinoids, however, avoids first-pass metabolism but the extremely hydrophobic nature and high molecular weights of cannabinoids limits diffusion across the aqueous layer of the dermis. This rate limiting step may only be modified by permeation enhancement, or by enhancement or manipulation of the molecule, such as in delivery tools, or as a pro-drug. Effective dermal transport is typically only obtained by permeation enhancement. However, mucosal transport, either through the oral mucosa, nasal mucosa, vaginal mucosa, or rectal mucosa have different properties as compared to the dermal layer, and thus allow for greater diffusion over these tissues. Even so, in vitro studies with human skin have determined the permeability potential of CBD to be 10-fold higher than that of $\Delta^9$-THC and $\Delta^8$-THC, consistent with CBD being relatively less lipophilic. This leads to opportunities for CBD for topical administration that are relatively unavailable for $\Delta^9$-THC, and which would be further improved for mucosal administration, which does not contain all of the systemic diffusion challenges of overcoming the barrier function of dermal skin layers.

Oral mucosal preparations undergo rapid absorption via the oral mucosa (and hence are useful for symptoms requiring rapid relief), producing plasma drug concentrations higher relative to oral delivery, but reduced relative to inhaled (smoke) consumption of cannabis material. However, even when utilizing oral mucosal preparations, part of the dose will be swallowed and thus ingested via the stomach, thus a portion becoming a standard oral formulation.

Cannabinoids rapidly distribute into well-vascularized organs (e.g., lung, heart, brain, liver), with subsequent equilibration into less vascularized tissue. Distribution may be affected by body size and composition, and disease states influencing the permeability of blood—tissue barriers. Therefore, when targeting less vascularized organs, the distribution and uptake may be reduced, as compared to other organs. This again points to implications for localized administration for EC treatment, instead of simply through the stomach or oral mucosa as with typical applications of therapeutic treatments.

CBD is hepatically metabolized, primarily by isozymes CYP450, CYP2C19 and CYP3A4 and additionally, CYP1A 1, CYP1A2, CYP2C9 and CYP2D6. After hydroxylation to 7-hydroxy cannabidiol (7-OH-CBD), there is further hepatic metabolism and subsequent fecal, and, to a lesser extent, urinary, excretion of those metabolites. CBD, like THC, has also been reported to have a long terminal elimination half-life, with the average half-lite following intravenous dosing observed to be 24±6 hours and post-inhalation to be 31±4 hours. An investigation of repeated daily oral administration of CBD elicited an elimination half-fife ranging from 2 to 5 days. A relatively longer elimination half-life is observed in heavy users, attributable to slow redistribution from deep compartments such as fatty tissues. Indeed, both THC and CBD are known to accumulate in adipose tissues with recurring administration. Consequently, THC and CBD concentrations of 1 µg/L$^{-1}$ may be measurable in the blood of heavy users more than 24 h following the last cannabis use.

Dose—response and drug—drug interaction information is lacking. Potential exists for pharmacokinetic interactions between both THC and CBD and other drugs, via inhibition or induction of enzymes or transporters and additionally, pharmacodynamic drug—drug interactions. There is a potential for CBD to compete with drugs metabolized through CYP 450 pathways, specifically those that interact with enzymes CYP3A4, CYP2C19, and CYP2D6. Dose adjustments may be necessary with substrates of CYP2C8, CYP2C9, CYP2C19, CYP1A2 and CYP2B6. Current literature demonstrates clinically significant drug interactions at doses of 20 mg/kg/day. One published case study concluded meaningful interactions with Warfarin at a dose of 10 mg/kg.

An in vitro study reported that CBD significantly inhibits P-glycoprotein-mediated drug transport, suggesting that CBD could potentially influence the absorption and disposition of other coadministered drugs. Coadministration of rifampicin (a CYP3A41 inducer) significantly reduced peak plasma concentrations of CBD, while coadministration of the CYP3A4 inhibitor ketoconazole nearly doubled peak plasma drug concentrations. Accordingly, it may be useful to coadminister a CYP3A4 inhibitor with CBD in order to reach higher blood plasma concentrations, or to reduce the total amount of CBD administered to reach therapeutic levels. Furthermore, in vitro, CBD was observed to be a potent inhibitor of CYP2C19 enzymes.

It will be appreciated that the embodiments and illustrations described herein are provided by way of example and that the present invention is not limited to what has been particularly disclosed. Rather, the scope of the present invention includes both combinations and sub combinations of the various features described above, as well as variations and modifications thereof that would occur to persons skilled in the art upon reading the forgoing description and that are not disclosed in the prior art. Therefore, the various compositions and methods may include one or all of the limitations of an embodiment, be performed in any order, or may combine limitations from different embodiments, as would be understood by those implementing the various methods and systems detailed herein.

What is claimed is:

1. A method of treatment of ovarian cancer comprising:
   a. forming an organoid from an ovarian cancer cell from a patient;
   b. determining whether the organoid is sensitive to one or more chemotherapeutic agents by applying a test amount of at least one chemotherapeutic agent to the organoid; and
   c. administering to the patient via an oral mucosal formulation, an effective amount of the at least one chemotherapeutic agent and concomitantly administering to the patient an effective amount of a composition comprising a cannabis extract (CE) wherein said cannabis extract comprises between 50% and 99% by weight of Cannabidiol (CBD).

2. The method of claim 1 wherein the CE is a broad spectrum hemp extract (BSHE) or a full spectrum hemp extract (FSHE) and wherein each of the BSHE or FSHE comprises 50% to 99% by weight of CBD and at least one other cannabinoid at a concentration of 0.1% to 10% wherein the at least one other cannabinoid is selected from the group consisting of:
   Δ-9-tetrahydrocannabinol ($\Delta^9$-THC), tetrahydrocannabinolic acid (THCA), tetrahydrocannabivarin (THCV), Δ-8-tetrahydrocannabinol ($\Delta^8$-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof.

3. The method of claim 2 wherein the CE comprises CBD at a concentration of between 60% and 99% and at least one other cannabinoid at a concentration of 0.1% to 10% wherein the at least one other cannabinoid is selected from the group consisting of: $\Delta^9$-tetrahydrocannabinol ($\Delta^9$-THC), tetrahydrocannabinolic acid (THCA), tetrahydrocannabivarin (THCV), Δ-8-tetrahydrocannabinol ($\Delta^8$-THC), cannabichromene (CBC), cannabichromene acid (CBCA), cannabigerol (CBG), cannabigerol acid (CBGA), cannabidiolic acid (CBDA), cannabidivarin (CBDV), cannabinol (CBN), cannabicyclol (CBL), and combinations thereof; and wherein the CE comprises a total concentration of cannabinoids of between 65% and 99%.

4. The method of claim 1 wherein the composition comprises at least one additional compound selected from the group consisting of: a terpene, a polyphenol, an essential fatty acid, a phytonutrient, and combinations thereof; and wherein the at least one additional compound makes up between 0.1% and 50% of the total weight of the composition.

5. The method of claim 1 wherein the composition comprises an oil or a fat as a carrier.

6. The method of claim 1 wherein the composition is administered at a pH of between 3.5 and 6.

7. The method of claim 1 wherein the chemotherapeutic agent and the CE are administered as one composition or as two different compositions.

8. The method of claim 1 wherein the chemotherapeutic agent is selected from the group consisting of: paclitaxel, altretamine, capecitabine, cyclosphosphamide, etoposide, gemcitabine, ifosfamide, itinotecan, doxorubicin, melphalan, pemetrexed, topotecan, binorelbine, carboplatin, cisplatin, docetaxel, fluorouracil, methotrexate, cetuximab, and combinations thereof.

9. The method of claim 1 wherein the ovarian cancer is a chemoresistant cancer.

10. The method of claim 1 wherein the effective amount of a chemotherapeutic agent is at least 50% less than an indicated individual dose and wherein the CE is administered at between 20 mg and 4,250 mg per day.

11. The method of claim 4 wherein the composition further comprises at least one terpene selected from the group consisting of: β-myrcene, β-caryophyllene, linalool, α-pinene, citral, D-limonene, eucalyptol, and combinations thereof.

12. The method of claim 4 wherein the composition further comprises at least one polyphenol selected from the group consisting of: a catechin, quercetin, cannflavin A/B/C, rutin, chlorogenic acid, and combinations thereof.

13. The method of claim 4 wherein the composition further comprises at least one fatty acid selected from the group consisting of: an omega 3 acid, an omega 6 acid, an omega 9 acid, and combinations thereof.

14. The method of claim 4 wherein the composition further comprises at least one phytonutrient wherein the phytonutrient is selected from the group consisting of: a tocopherol, a sterol, carotene, an aliphatic alcohol, a mineral, and combinations thereof.

15. The method of claim 1 further comprising:
   i. at least one terpene selected from the group consisting of: β-myrcene, β-caryophyllene, linalool, α-pinene, citral, D-limonene, eucalyptol, and combinations thereof;
   ii. at least one polyphenol selected from the group consisting of: catechins, quercetin, cannflavin A/B/C, rutin, chlorogenic acid, and combinations thereof;
   iii. at least one essential fatty acid selected from the group consisting of: an omega 3, an omega 6, an omega 9, and combinations thereof; and
   iv. at least one phytonutrient selected from the group consisting of: a tocopherol, a sterol, carotene, an aliphatic alcohol, a mineral, and combinations thereof.

16. A method of treatment of ovarian cancer comprising:
   a. forming an organoid from an ovarian cancer cell from a patient;
   b. determining whether the organoid is sensitive to one or more chemotherapeutic agents by applying a test amount of at least one chemotherapeutic agent to the organoid; and c. administering to the patient via an intravaginal formulation, an effective amount of the at least one chemotherapeutic agent and concomitantly administering to the patient an effective amount of a composition comprising a cannabis extract (CE) wherein said cannabis extract comprises between 50% and 99% by weight of CBD.

\* \* \* \* \*